United States Patent
Dimarchi et al.

(10) Patent No.: US 10,683,334 B2
(45) Date of Patent: Jun. 16, 2020

(54) AQUEOUSLY SOLUBLE AND CHEMICALLY STABLE GLUCAGON PEPTIDES

(71) Applicant: INDIANA UNIVERSITY RESEARCH AND TECHNOLOGY CORPORATION, Indianapolis, IN (US)

(72) Inventors: Richard D. Dimarchi, Carmel, IN (US); John P. Mayer, Indianapolis, IN (US); Piotr Mroz, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/098,236

(22) PCT Filed: May 31, 2017

(86) PCT No.: PCT/US2017/035101
§ 371 (c)(1),
(2) Date: Nov. 1, 2018

(87) PCT Pub. No.: WO2017/210241
PCT Pub. Date: Dec. 7, 2017

(65) Prior Publication Data
US 2019/0218268 A1 Jul. 18, 2019

Related U.S. Application Data

(60) Provisional application No. 62/344,672, filed on Jun. 2, 2016.

(51) Int. Cl.
*A61K 38/26* (2006.01)
*C07K 14/605* (2006.01)
*A61K 38/28* (2006.01)
*A61P 3/10* (2006.01)

(52) U.S. Cl.
CPC .......... *C07K 14/605* (2013.01); *A61K 38/26* (2013.01); *A61K 38/28* (2013.01); *A61P 3/10* (2018.01)

(58) Field of Classification Search
None
See application file for complete search history.

(56) References Cited

U.S. PATENT DOCUMENTS

| | | |
|---|---|---|
| 2002/0090646 A1 | 7/2002 | Liu et al. |
| 2005/0026827 A1 | 2/2005 | Coy et al. |
| 2007/0060512 A1 | 3/2007 | Sadeghi et al. |
| 2008/0045461 A1 | 2/2008 | Ewing et al. |
| 2010/0239554 A1 | 9/2010 | Schellenberger et al. |
| 2013/0122023 A1 | 5/2013 | Woo et al. |

FOREIGN PATENT DOCUMENTS

WO WO2000/34332 6/2000

OTHER PUBLICATIONS

Thomsen et al. "The Amino Acid Sequence of Human Glucagon", FEBS, 1972, 315-319 (Year: 1972).*
Chabenne et al., "A glucagon analog chemically stabilized for immediate treatment of life-threatening hypoglycemia", Molecular Metabolism, 2014, 293-300 (Year: 2014).*
Jackson et al., "Stable Liquid Glucagon Formulations for Rescues Treatment and Bi-Hormonal Closed-Loop Pancreas", Curr Diab Rep, 2012, 705-710 (Year: 2012).*
Castle et al., "Factors Influencing the Effectiveness of Glucagon for Preventing Hypoglycemia", Journals of Diabetes Science and Technology, 2010, 1305-1310 (Year: 2010).*
PCT International Search Report and Written Opinion completed by the ISA/US on Sep. 27, 2017 and issued in connection with PCT/US2017/035101.
Mroz et al, Pyridyl-alanine as a Hydrophylic, Aromatic Element in Peptide Structural Optimization, Journal of Medicinal Chemistry, vol. 59 (17) Aug. 25, 2016 pp. 8061-8067.
Chabenne et al, Structural Refinement of Glucagon for Therapeutic Use, Journal of Medicinal Chemistry, Dec. 18, 2019 XP055667086; 10.1021/acs.jmedchem.9b01493.

* cited by examiner

Primary Examiner — Lianko G Garyu
(74) Attorney, Agent, or Firm — Barnes & Thornburg LLP

(57) ABSTRACT

Modified glucagon peptides are disclosed having improved solubility and/or stability while retaining glucagon agonist activity. The glucagon peptides have been modified by the substitution of pyridyl-alanine for a native amino acid at one or more of positions 6, 10 or 13 and/or substitution with an amino acid in the D-conformation at position 20 or 21 compared to native glucagon.

19 Claims, 13 Drawing Sheets

Specification includes a Sequence Listing.

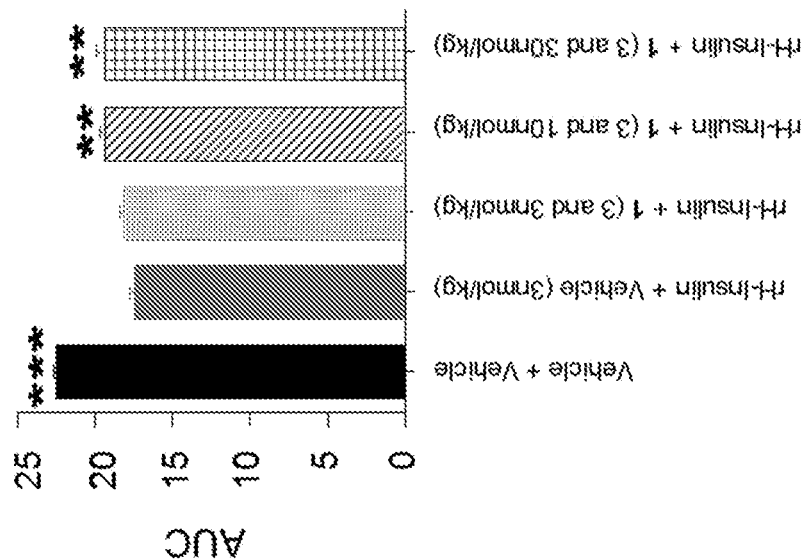
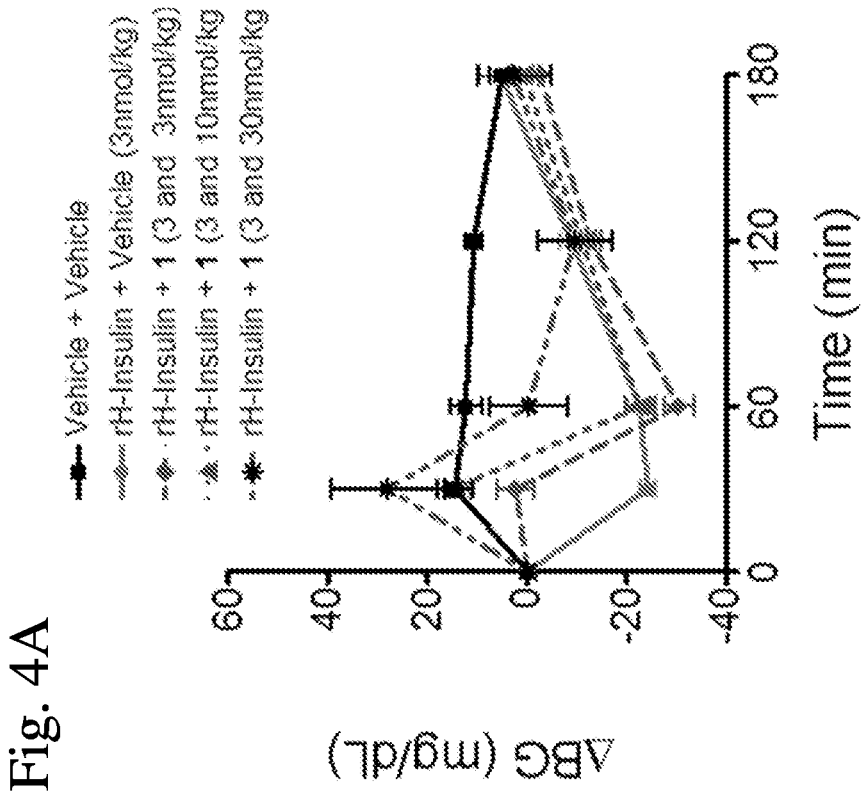
Fig. 4A

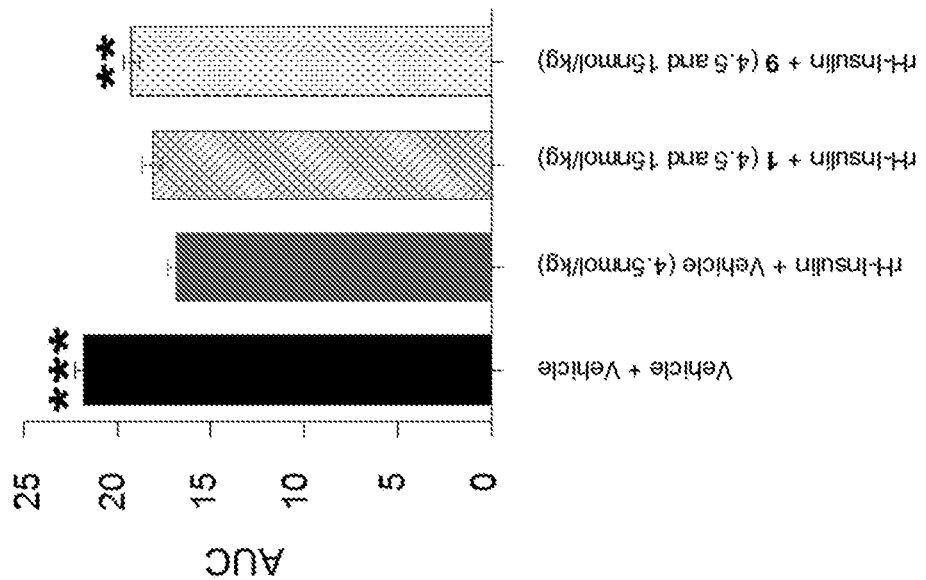
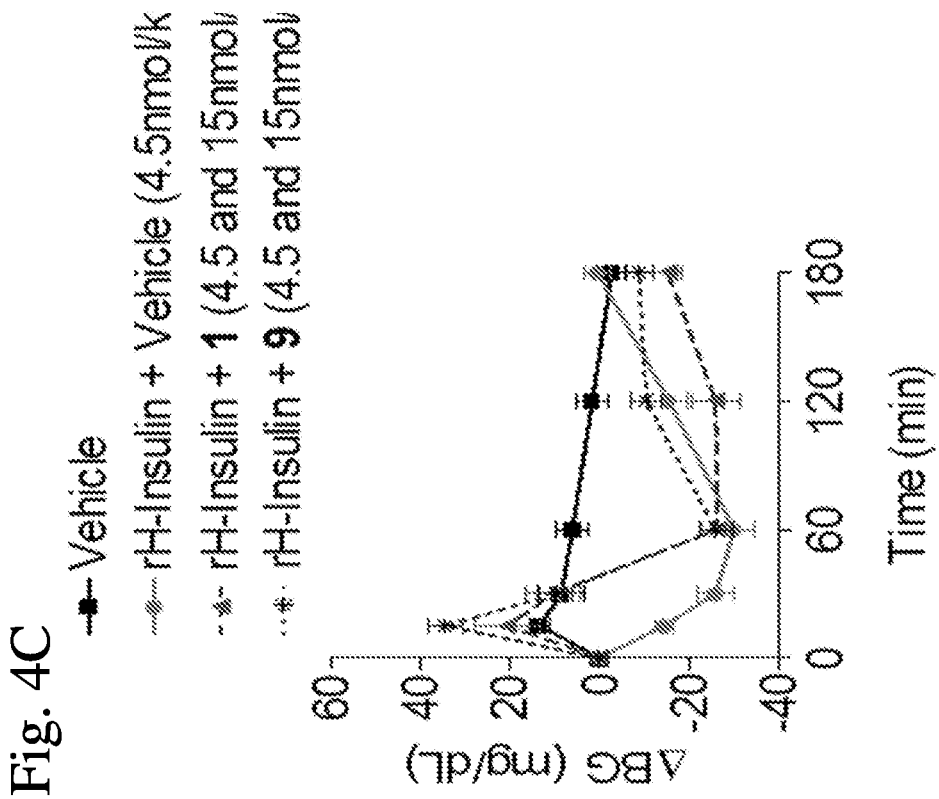
Fig. 4C

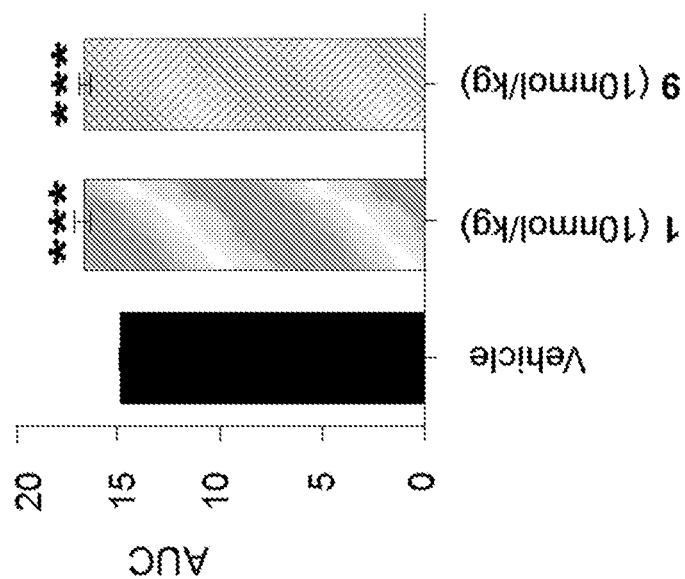
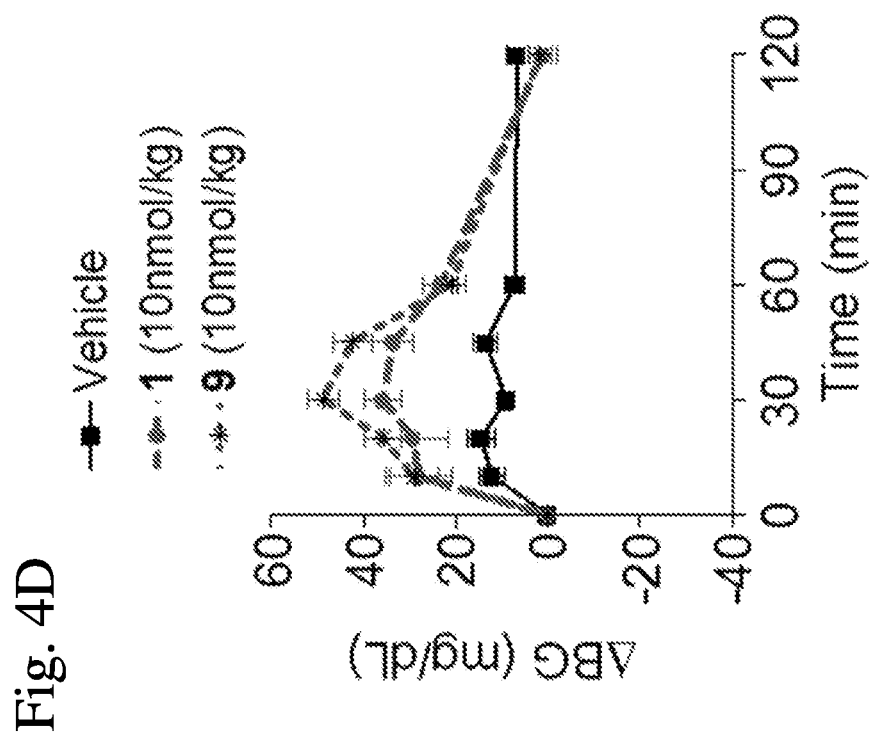
Fig. 4D

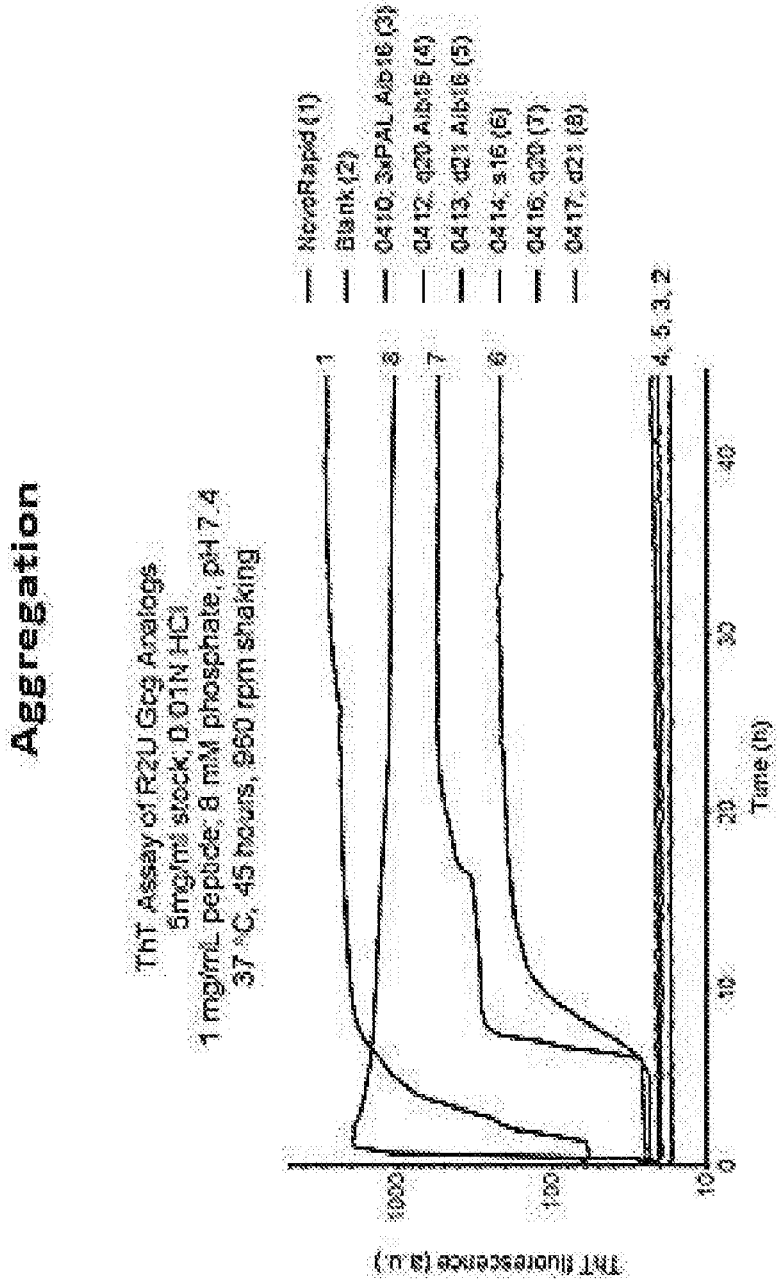

AQUEOUSLY SOLUBLE AND CHEMICALLY STABLE GLUCAGON PEPTIDES

CROSS REFERENCE TO RELATED APPLICATIONS

This application claims priority to U.S. Provisional Patent Application No. 62/344,672 filed on Jun. 2, 2016, the disclosure of which is hereby expressly incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 557 kilobytes acii (text) file named "265440seqlist_st25.txt," created on May 21, 2017.

BACKGROUND

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon.

Hypoglycemia occurs when blood glucose levels drops too low to provide enough energy for the body's activities. In adults or children older than 10 years, hypoglycemia is uncommon except as a side effect of diabetes treatment, but it can result from other medications or diseases, hormone or enzyme deficiencies, or tumors. When blood glucose begins to fall, glucagon, a hormone produced by the pancreas, signals the liver to break down glycogen and release glucose, causing blood glucose levels to rise toward a normal level. Thus, glucagon's most recognized role in glucose regulation is to counteract the action of insulin and maintain blood glucose levels. However for diabetics, this glucagon response to hypoglycemia may be impaired, making it harder for glucose levels to return to the normal range.

Hypoglycemia is a life threatening event that requires immediate medical attention. The administration of glucagon is an established medication for treating acute hypoglycemia and it can restore normal levels of glucose within minutes of administration. When glucagon is used in the acute medical treatment of hypoglycemia, a crystalline form of glucagon is solubilized with a dilute acid buffer and the solution is injected intramuscularly. While this treatment is effective, the methodology is cumbersome and dangerous for someone that is semi-conscious. Accordingly, there is a need for a glucagon analog that maintains the biological performance of the parent molecule but is sufficiently soluble and stable, under relevant physiological conditions, that it can be pre-formulated as a solution, ready for injection.

A number of approaches have been advanced to develop a soluble formulation of native glucagon including the use of aqueous and nonaqueous formulations. In addition modifications to the primary sequence have been reported to reduce aggregation and chemical degradation. These modifications include a reduction in the number of native amide side chains, including the substitution of the acid-sensitive Gln3 with a chemically stable mimetic. Additionally, the substitution of Ser16 with aminoisobutyric acid (Aib) not only improved biophysical properties as reflected by a minimized propensity to physical aggregate but also prevented chemical degradation via isoaspartimide formation between Asp15 and Ser16. Separately from the chemical and physical stabilization of the peptide, two approaches have been taken to enhance its aqueous solubility. These include the C-terminal extension with the exendin-derived nine amino acid sequence and the introduction of anionic charge to the C-terminus to decrease the isoelectric point as a means to increase neutral pH solubility. However, additional improvements in glucagon solubility and stability are desirable.

Diabetics are encouraged to maintain near normal blood glucose levels to delay or prevent microvascular complications. Achievement of this goal usually requires intensive insulin therapy. In striving to achieve this goal, physicians have encountered a substantial increase in the frequency and severity of hypoglycemia in their diabetic patients. Accordingly, improved pharmaceuticals and methodologies are needed for treating diabetes that are less likely to induce hypoglycemia than current insulin therapies.

As described herein, high potency glucagon peptides are provided that exhibit enhanced aqueous solubility.

SUMMARY

One embodiment of the invention provides glucagon peptides that retain glucagon receptor activity and exhibit improved solubility relative to native glucagon (SEQ ID NO: 1), optionally without impacting the isoelectric point of the analog relative to native glucagon. Native glucagon exhibits poor solubility in aqueous solution, particularly at physiological pH, with a tendency to aggregate and precipitate over time. In contrast, in one embodiment the glucagon peptides disclosed herein exhibit at least 2-fold, 5-fold, or even higher solubility compared to native glucagon at a pH between 6 and 7.

As disclosed herein glucagon peptides are provided that have pharmacokinetic and pharmacodynamics profiles comparable to native hormone but with solubility at physiological pH and chemical stability, once commercially formulated, to constitute a ready-to-use medicine. In one embodiment glucagon peptides having enhanced solubility and activity at the GLP-1 or GIP receptors are also provided. The enhanced solubility is derived from the discovery that aromatic amino acid residues within the glucagon amino acid sequence can be replaced with pyridyl-alanine to generate structural analogs having pharmacokinetic and pharmacodynamics profiles comparable to native hormone.

In accordance with one embodiment a glucagon peptide is provided wherein the glucagon peptide has enhanced solubility at physiological pH relative to native glucagon. As disclosed herein, in one embodiment the enhanced solubility results from the substitution of one or more amino acids selected from positions 6, 10 or 13 with pyridyl-alanine.

In accordance with one embodiment the solubility of glucagon peptides is further improved by amino acid substitutions and/or additions that introduce a charged amino acid into the C-terminal portion of the peptide, and in one embodiment at a position C-terminal to position 27 of SEQ ID NO: 1. Optionally, in addition to the introduction of pyridyl-alanine at an amino acid position selected from 6, 10 or 13, one, two or three charged amino acids may be introduced within the C-terminal portion, and in one embodiment C-terminal to position 27. In accordance with one embodiment the native amino acid(s) at positions 28 and/or 29 are substituted with a charged amino acid, and/or one to three charged amino acids are added to the C-terminus of the peptide, after position 29. In exemplary embodiments, one, two or all of the charged amino acids are negatively charged. Additional modifications, e.g. conservative substitutions, may be made to the glucagon peptide that still allow it to retain glucagon activity.

In accordance with one embodiment the solubility of glucagon peptide is further improved by amino acid substitutions and/or additions that introduce an amino acid in the D-isomer conformation. In one embodiment an amino acid in the D-isomer conformation is substituted for the natural amino acid at position 20 or 21. In one embodiment a glucagon peptide is provided comprising dGln at position 20 and/or dAsp at position 21. In one embodiment a glucagon peptide is provided comprising 1, 2 or 3 substitutions at positions selected from positions 6, 10 or 13 with pyridyl-alanine in combination with a substitution of Aib at position 16 and dGln at position 20 and/or dAsp at position 21.

The present invention further encompasses pharmaceutically acceptable salts of said glucagon peptides.

In some embodiments, modifications at position 1 or 2 can increase the peptide's resistance to dipeptidyl peptidase IV (DPP IV) cleavage. For example, the amino acid at position 2 may be substituted with D-serine, D-alanine, valine, glycine, N-methyl serine, N-methyl alanine, or amino isobutyric acid. Alternatively, or in addition, the amino acid at position 1 may be substituted with D-histidine (D-His), desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

It was observed that modifications at position 2 (e.g. Aib at position 2) and in some cases modifications at position 1 (e.g. DMIA at position 1) may reduce glucagon activity, sometimes significantly. This reduction in glucagon activity can be restored by stabilization of the alpha-helix structure in the C-terminal portion of glucagon (around amino acids 12-29). In some embodiments, stabilization is via a covalent bond between amino acids at positions "i" and "i+4", wherein i is any integer from 12 to 25. In some specific embodiments, "i" and "i+4" are 12 and 16, 16 and 20, or 20 and 24, or 24 and 28. In some embodiments, this covalent bond is a lactam bridge between a glutamic acid at position 16 and a lysine at position 20. In exemplary embodiments, the bridge or linker is about 8 (or about 7-9) atoms in length. In other embodiments, stabilization is via a covalent bond between amino acids at positions "j" and "j+3," wherein j is any integer between 12 and 27. In exemplary embodiments, the bridge or linker is about 6 (or about 5-7) atoms in length. In yet other embodiments, stabilization is via a covalent bond between amino acids at positions "k" and "k+7," wherein k is any integer between 12 and 22. In some embodiments, this covalent bond is an intramolecular bridge other than a lactam bridge. For example, suitable covalent bonding methods (i.e., means of forming a covalent intramolecular bridge) include any one or more of olefin metathesis, lanthionine-based cyclization, disulfide bridge or modified sulfur-containing bridge formation, the use of a, w-diaminoalkane tethers, the formation of metal-atom bridges, and other means of peptide cyclization.

In yet other embodiments, the helix is stabilized by non-covalent bonds (i.e., non-covalent intramolecular bridges), including but not limited to hydrogen-bonding, ionic interactions, and salt bridges.

In other embodiments of the invention, stabilization of the alpha-helix structure in the C-terminal portion of the glucagon peptide (around amino acids 12-29) is achieved through purposeful introduction of one or more α, α-disubstituted amino acids at positions that retain the desired activity. In some embodiments, one, two, three, four or more of positions 16, 17, 18, 19, 20, 21, 24 or 29 of a glucagon peptide is substituted with an α, α-disubstituted amino acid. For example, substitution of position 16 of a glucagon peptide with amino iso-butyric acid (Aib) provides a stabilized alpha helix in the absence of a salt bridge or lactam. Such peptides are considered herein as a peptide lacking an intramolecular bridge. In specific aspects, stabilization of the alpha-helix is accomplished by introducing one or more α, α-disubstituted amino acids without introduction of a covalent intramolecular bridge, e.g., a lactam bridge, a disulfide bridge. Such peptides are considered herein as a peptide lacking a covalent intramolecular bridge. In some embodiments, one, two, three or more of positions 16, 20, 21 or 24 are substituted with Aib.

Thus, in some embodiments the present disclosure provides a glucagon peptide comprising the amino acid sequence:

X1-X2-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Z (SEQ ID NO: 839) with 1 to 3 amino acid modifications thereto, wherein one or more amino acids selected from positions 6, 10 or 13 are substituted with pyridyl-alanine and optionally 1 or 2 amino acids selected from positions 20 and 21 are substituted with an amino acid in the D-isomer conformation, optionally the substituted amino acid is a D-isomer of the native amino acid at that position;

X1 and/or X2 is a non-native amino acid that reduces susceptibility of (or increases resistance of) the glucagon peptide to cleavage by dipeptidyl peptidase IV (DPP-IV), optionally X1 is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA) and X2 is selected from the group consisting of Ser, D-Ser, Ala, D-Ala, Gly, N-methyl-Ser, Aib, Val, or alpha-amino-N-butyric acid, wherein Z is selected from the group consisting of —COOH (the naturally occurring C-terminal carboxylate), -Asn-COOH, Asn-Thr-COOH, and Y-COOH, wherein Y is 1 to 2 amino acids, optionally wherein an intramolecular bridge, preferably a covalent bond, connects the side chains of an amino acid at position i and an amino acid at position i+4, wherein i is 12, 16, 20 or 24.

In some embodiments, the intramolecular bridge is a lactam bridge. In some embodiments, the amino acids at positions i and i+4 of SEQ ID NO: 839 are Lys and Glu, e.g., Glu16 and Lys20. In some embodiments, X1 is selected from the group consisting of: D-His, N-methyl-His, alpha-methyl-His, imidazole acetic acid, des-amino-His, hydroxyl-His, acetyl-His, homo-His, and alpha, alpha-dimethyl imidazole acetic acid (DMIA). In other embodiments, X2 is selected from the group consisting of: D-Ser, D-Ala, Gly, N-methyl-Ser, Val, and alpha, amino isobutyric acid (Aib). In some embodiments, the glucagon peptide is covalently linked to a hydrophilic moiety at any of amino acid positions 16, 17, 20, 21, 24, 29, 40, within a C-terminal extension, or at the C-terminal amino acid. In exemplary embodiments, this hydrophilic moiety is covalently linked to a Lys, Cys, Orn, homocysteine, or acetyl-phenylalanine residue at any of these positions. Exemplary hydrophilic moieties include polyethylene glycol (PEG), for example, of a molecular weight of about 1,000 Daltons to about 40,000 Daltons, or about 20,000 Daltons to about 40,000 Daltons.

In other embodiments, the invention provides a glucagon peptide with glucagon agonist activity, comprising the amino acid sequence:

X1-X2-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Z (SEQ ID NO: 839), wherein one or more amino acids selected from positions 6, 10 or 13 are substituted with pyridyl-alanine;

X1 and/or X2 is a non-native amino acid that reduces susceptibility of (or increases resistance of) the glucagon peptide to cleavage by dipeptidyl peptidase IV (DPP-IV), optionally X1 is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA) and X2 is selected from the group consisting of Ser, D-Ser, Ala, D-Ala, Gly, N-methyl-Ser, Aib, Val, or alpha-amino-N-butyric acid, wherein one, two, three, or four of positions 16, 20, 21, and 24 of the glucagon peptide are substituted with an α, α-disubstituted amino acid, and wherein Z is selected from the group consisting of —COOH (the naturally occurring C-terminal carboxylate), -Asn-COOH, Asn-Thr-COOH, and Y-COOH, wherein Y is 1 to 2 amino acids.

Exemplary further amino acid modifications to the foregoing glucagon peptides or analogs include substitution of Thr at position 7 with an amino acid lacking a hydroxyl group, e.g., Abu (aminobutyric acid) or Ile, optionally, in combination with substitution or addition of an amino acid comprising a side chain covalently attached (optionally, through a spacer) to an acyl or alkyl group, which acyl or alkyl group is non-native to a naturally-occurring amino acid, substitution of Lys at position 12 with Arg; substitution of Asp at position 15 with Glu; substitution of Ser at position 16 with Thr or aminoisobutyric acid (Aib); substitution of Gln at position 20 with dGln, Ser, Thr, Ala or Aib; substitution of Asp at position 21 with dAsp or Glu; substitution of Gln at position 24 with Ser, Thr, Ala or Aib; substitution of Met at position 27 with Leu or Nle; substitution of Asn at position 28 with a charged amino acid; substitution of Asn at position 28 with a charged amino acid selected from the group consisting of Lys, Arg, His, Asp, Glu, cysteic acid, and homocysteic acid; substitution at position 28 with Asn, Asp, or Glu; substitution at position 28 with Asp; substitution at position 28 with Glu; substitution of Thr at position 29 with a charged amino acid; substitution of Thr at position 29 with a charged amino acid selected from the group consisting of Lys, Arg, His, Asp, Glu, cysteic acid, and homocysteic acid; substitution at position 29 with Asp, Glu, or Lys; substitution at position 29 with Glu; insertion of 1-3 charged amino acids after position 29; insertion at position 30 (i.e., after position 29) of Glu or Lys; optionally with insertion at position 31 of Lys; addition of SEQ ID NO: 820 to the C-terminus, optionally, wherein the amino acid at position 29 is Thr or Gly; substitution or addition of an amino acid covalently attached to a hydrophilic moiety; or a combination thereof.

In certain embodiments, the glucagon peptide comprises a sequence of SEQ ID NO: 1, or a sequence that differs from SEQ ID NO: 1 by 1, 2, 3, 4, 5, 6, 7, 8, 9, or 10 amino acid modifications, wherein the glucagon peptide is further modified to comprises one or more pyridyl-alanine or histidine amino acid substitution at positions 6, 10 or 13 relative to the native sequence of glucagon. In a further embodiment the glucagon peptide comprises an amino acid with a side chain covalently attached, optionally through a spacer, to an acyl group or an alkyl group, wherein the acyl group or alkyl group is non-native to a naturally-occurring amino acid. In one embodiment the covalently linked acyl or alkyl group has a carboxylate at its free end. The acyl group in some embodiments is a C4 to C30 fatty acyl group, optionally with carboxylate groups at each end. In one embodiment the glucagon peptide comprises a covalently linked C4 to C30 acyl group optionally with a carboxylate at its free end. In specific aspects, the acyl group or alkyl group is covalently attached to the side chain of the amino acid at position 10.

In yet further exemplary embodiments, any of the foregoing peptides can be further modified to improve stability by modifying the amino acid at position 15 of SEQ ID NO: 1 to reduce degradation of the peptide over time, especially in acidic or alkaline buffers. In exemplary embodiments, Asp at position 15 is substituted with a Glu, homo-Glu, cysteic acid, or homo-cysteic acid.

Alternatively, any of the glucagon peptides described herein can be further modified to improve stability by modifying the amino acid at position 16 of SEQ ID NO: 1. In exemplary embodiments, Ser at position 16 is substituted with Thr, or any of the amino acids substitutions described above which enhance potency at the glucagon receptor. Such modifications reduce cleavage of the peptide bond between Asp15-Ser16.

Maintained or enhanced activity at the glucagon receptor may be achieved by modifying the Gln at position 3 with a glutamine analog. For example, a glucagon peptide comprising a glutamine analog at position 3 may exhibit about 5%, about 10%, about 20%, about 50%, or about 85% or greater the activity of native glucagon (e.g. SEQ ID NO: 1) at the glucagon receptor. In some embodiments, the glutamine analog is a naturally occurring or a non-naturally occurring amino acid comprising a side chain of Structure I, II or III:

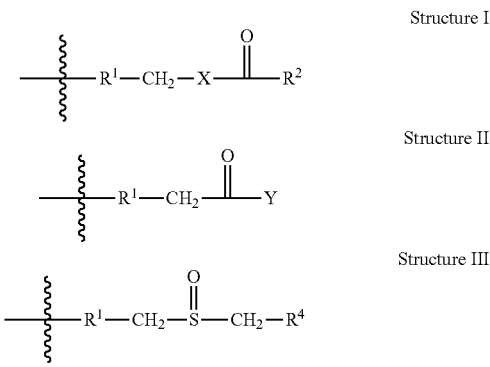

wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R_1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl.

Enhanced activity at the glucagon receptor also may be achieved by covalently attaching an acyl or alkyl group, e.g., an acyl or alkyl group which is non-native to a naturally occurring amino acid (e.g., a C4 to C30 fatty acyl group, a C4 to C30 alkyl group), to the side chain of an amino acid of the glucagon peptide. In some embodiments, the acylated or alkylated glucagon peptides lack an intramolecular bridge, e.g., a covalent intramolecular bridge (e.g., a lactam). In certain aspects, the acyl or alkyl group is attached to the side chain of the amino acid of the glucagon peptide through a spacer, e.g., a spacer which is 3 to 10 atoms in length. In some embodiments, the acyl or alkyl group is attached to the side chain of the amino acid at position 10 of the glucagon peptide through a spacer. In specific embodiments, the acylated or alkylated glucagon peptides further comprise a modification which selectively decreases the activity of the peptide at the GLP-1 receptor. For example, the acylated or alkylated glucagon peptide may comprise a C-terminal alpha carboxylate, a substitution of the Thr at position 7 with an amino acid lacking a hydroxyl group, e.g., Abu or Ile, a deletion of the amino acid(s) C-terminal to the amino acid at position 27 or 28, yielding a 27- or 28-amino acid peptide, or a combination thereof.

In some embodiments, any of the glucagon peptides described herein can be further modified to reduce degradation at various amino acid positions by modifying any one, two, three, or all four of positions 20, 21, 24, or 27. Exemplary embodiments include substitution of Gln at position 20 with Ala or Aib, substitution of Asp at position 21 with Glu, substitution of Gln at position 24 with Ala or Aib, substitution of Met at position 27 with Leu or Nle. Removal or substitution of methionine reduces degradation due to oxidation of the methionine. Removal or substitution of Gln or Asn reduces degradation due to deamidation of Gln or Asn. Removal or substitution of Asp reduces degradation that occurs through dehydration of Asp to form a cyclic succinimide intermediate followed by isomerization to iso-aspartate.

The glucagon peptide may be part of a dimer, trimer or higher order multimer comprising at least two, three, or more peptides bound via a linker, wherein at least one or both peptides is a glucagon peptide. The dimer may be a homodimer or heterodimer. In some embodiments, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects of the invention, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

A conjugate moiety may be covalently linked to any of the glucagon peptides described herein, including a dimer, trimer or higher order multimer. Fusion peptides comprising the amino acid sequence of any of SEQ ID NOs: 820 to 822 are also contemplated.

Any of the modifications described above which increase glucagon receptor activity, retain partial glucagon receptor activity, improve solubility, increase stability, or reduce degradation can be applied to glucagon peptides individually or in combination.

In accordance with one embodiment a pharmaceutical composition is provided comprising any of the novel glucagon peptides disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a glucagon peptide at a concentration of at least A, wherein A is 0.001 mg/ml, 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In other embodiments, such compositions may contain a glucagon peptide at a concentration of at most B, wherein B is 30 mg/ml, 25 mg/ml, 24 mg/ml, 23 mg/ml, 22 mg/ml, 21 mg/ml, 20 mg/ml, 19 mg/ml, 18 mg/ml, 17 mg/ml, 16 mg/ml, 15 mg/ml, 14 mg/ml, 13 mg/ml, 12 mg/ml, 11 mg/ml 10 mg/ml, 9 mg/ml, 8 mg/ml, 7 mg/ml, 6 mg/ml, 5 mg/ml, 4 mg/ml, 3 mg/ml, 2 mg/ml, 1 mg/ml, or 0.1 mg/ml. In some embodiments, the compositions may contain a glucagon peptide at a concentration range of A to B mg/ml, for example, 0.001 to 30.0 mg/ml. In one embodiment the pharmaceutical compositions comprise aqueous solutions that are sterilized and optionally stored within various containers. Such solutions can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. Devices may include a syringe and needle, or a pre-filled syringe. The containers or kits may be labeled for storage at ambient room temperature or at refrigerated temperature.

In accordance with one embodiment a method of rapidly increasing glucose level, normalizing blood glucose level, stabilizing blood glucose level, or preventing or treating hypoglycemia using a pre-formulated aqueous composition of a glucagon peptide of the invention is provided. The method comprises the step of administering an effective amount of an aqueous solution comprising a novel modified glucagon peptide of the present disclosure. In some embodiments, the aqueous composition is pre-packaged in a device that is used to administer the composition to the patient. In another embodiment a method is provided for inducing the temporary paralysis of the intestinal tract. The method comprises the step of administering one or more of the glucagon peptides disclosed herein to a patient in need thereof.

In further embodiments, methods of treating hyperglycemia or diabetes involving co-administering insulin and a glucagon peptide of the present disclosure are provided. Hyperglycemia includes diabetes, diabetes mellitus type I, diabetes mellitus type II, or gestational diabetes, either insulin-dependent or non-insulin-dependent, and reducing complications of diabetes including nephropathy, retinopathy and vascular disease. Co-administration of insulin and a glucagon peptide of the invention can reduce nocturnal hypoglycemia and/or buffer the hypoglycemic effects of insulin, allowing the same or higher doses of short-acting or long-acting insulin to be administered with fewer adverse hypoglycemic effects. Compositions comprising insulin together with a glucagon peptide of the invention are also provided.

In accordance with one embodiment an improved method of regulating blood glucose levels in insulin dependent patients is provided. The method comprises the steps of administering insulin in an amount therapeutically effective for the control of diabetes and administering a novel modified glucagon peptide of the present disclosure in an amount therapeutically effective for the prevention of hypoglycemia, wherein said administering steps are conducted within twelve hours of each other. In one embodiment the glucagon peptide and the insulin are co-administered as a single composition.

All therapeutic methods, pharmaceutical compositions, kits and other similar embodiments described herein contemplate that the use of the term glucagon peptides, glucagon agonists, or glucagon analogs includes all pharmaceutically acceptable salts or esters thereof.

The foregoing summary is not intended to define every aspect of the invention, and additional embodiments are described in other sections, such as the Detailed Description. The entire document is intended to be related as a unified disclosure, and it should be understood that all possible combinations of features described herein may be contemplated, even if the combination of features are not found together in the same sentence, or paragraph, or section of this document.

Moreover, the invention includes any one or all embodiments of the invention that are narrower in scope in any way than the variations defined by specific paragraphs herein. For example, where certain aspects of the invention are described as a genus, it should be understood that every member of a genus is, individually, an embodiment of the invention, and that combinations of two or more members of the genus are embodiments of the invention.

BRIEF DESCRIPTION OF THE DRAWINGS

FIG. 3 shows the percent change in $EC_{50}$ at time 0, 1 week and at 4 weeks.

FIGS. 4A-4D are graphs of the change in blood glucose levels over time in lean rats which were administered escalating doses of native glucagon (FIG. 4A) or analog 9 (FIG. 4B) with a fixed dose of insulin. FIG. 4C is a graph of the change in blood glucose levels over time directly comparing the effect of administering native glucagon vs analog 9 in lean rats when co-administering a fixed dose of insulin. FIG. 4D is a graph of the change in blood glucose levels over time directly comparing the effect of administering native glucagon vs analog 9 in lean rats in the absence of a fixed dose of insulin.

FIG. 6A demonstrates the solubility, in PBS at pH 7 and room temperature, of each glucagon peptide; FIG. 6B provides data regarding the aggregation of each glucagon peptide (as measured by the thioflavin-T fluorescence assay as disclosed in Example 6); and FIG. 6C provides data regarding the activity of each glucagon peptide using the cAMP assay as disclosed in Example 3.

(FIG. 7B). Tested glucagon peptides include Aib16, q20 (SEQ ID NO: 970), 3-Pal10, Aib16, q20 (SEQ ID NO: 971), 3-Pal13, Aib16, q20 (SEQ ID NO: 972), 3-Pal10&13, Aib16, q20 (SEQ ID NO: 973).

FIG. 8 is a graph demonstrating the stability of glucagon analogs based on the thioflavin-T fluorescence (ThT) assay as described in Example 6. The following numbering is used for the graphs: 1: NovoRapid (insulin aspart); 2: blank; 3: compound 9 (3-Pal at positions 6, 10 and 13, Aib at position 16; SEQ ID NO: 950); 4: Peptide having dGln at position 20, Aib at position 16 (SEQ ID NO: 974); 5: Peptide having dAsp at position 21, Aib at position 16 (SEQ ID NO: 975); 6: Peptide having dSer at position 16 (SEQ ID NO: 976); 7: Peptide having dGln at position 20 (SEQ ID NO: 977) and 8: Peptide having dAsp at position 21 (SEQ ID NO: 978). Peptides represented by graph lines numbered 3, 4 and 5 (i.e. SEQ ID NO's: 950, 974 and 975) showed stability over 45 hours at 37° C., pH 7.0 in phosphate buffer.

DETAILED DESCRIPTION

Definitions

Figure 1:
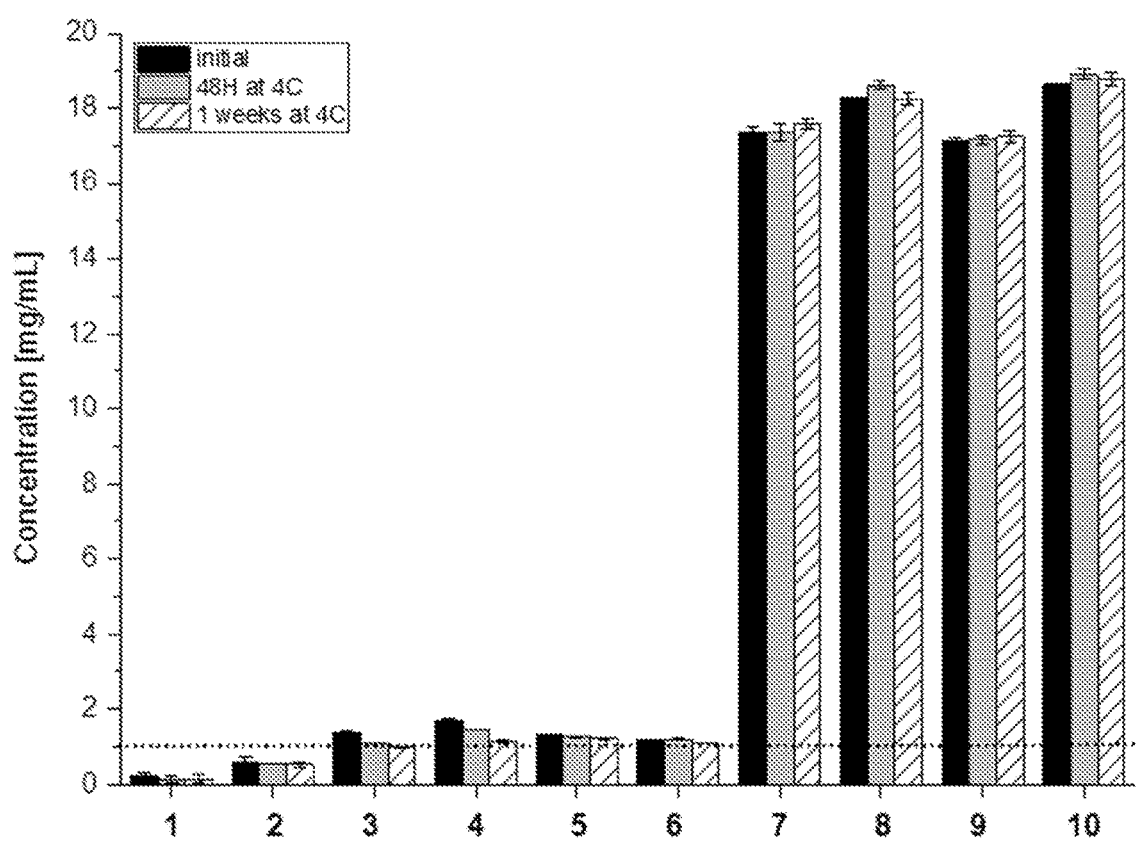
FIG. 1 is a bar graph showing the change in solubility of Pyridyl-alanine-modified glucagon (Table 1) after incubation in PBS i) initially at room temperature, ii) at 4° C. for 48 hours or iii) at 4° C. for 7 days. The black marked line represents pharmaceutically relevant concentration for injectable emergency glucagon formulation.

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia, as measured, for example, by an increase in blood glucose level. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein the term "native glucagon" refers to a peptide consisting of the sequence of SEQ ID NO: 1, and the term "native GLP-1" is a generic term that designates GLP-1(7-36)amide (consisting of the sequence of SEQ ID NO: 858), GLP-1(7-37)acid (consisting of the sequence of SEQ ID NO: 857) or a mixture of those two compounds. As used herein, a general reference to "glucagon" or "GLP-1" in the absence of any further designation is intended to mean native glucagon or native GLP-1, respectively.

A "glucagon peptide" as used herein includes any peptide comprising, either the amino acid sequence of SEQ ID NO: 1, or any analog of the amino acid sequence of SEQ ID NO: 1, including amino acid substitutions, additions, or deletions, or post translational modifications (e.g. methylation, acylation, ubiquitination and the like) of the peptide, wherein the analog stimulates glucagon or GLP-1 receptor activity, e.g., as measured by cAMP production using the assay described in Example 3.

The term "glucagon agonist" refers to a complex comprising a glucagon peptide that stimulates glucagon receptor activity, e.g., as measured by cAMP production using the assay described in Example 3.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. Designation of an amino acid without specifying its stereochemistry is intended to encompass either the L or D form of the amino acid or a racemic mixture. The D form of the amino acid is specified by inclusion of a lower case d before the three letter code (e.g., dLys).

As used herein an amino acid "modification" refers to a substitution, addition or deletion of an amino acid, and includes substitution with, or addition of, any of the 20 amino acids commonly found in human proteins, as well as atypical or non-naturally occurring amino acids. Throughout the application, all references to a particular amino acid position by number (e.g. position 28) refer to the amino acid at that position in native glucagon (SEQ ID NO:1) or the corresponding amino acid position in any analogs thereof. For example, a reference herein to "position 28" would mean the corresponding position 27 for a glucagon analog in which the first amino acid of SEQ ID NO: 1 has been deleted. Similarly, a reference herein to "position 28" would mean the corresponding position 29 for a glucagon analog in which one amino acid has been added before the N-terminus of SEQ ID NO: 1.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
  Ala, Ser, Thr, Pro, Gly;
II. Polar, negatively charged residues and their amides:
  Asp, Asn, Glu, Gln, cysteic acid and homocysteic acid;
III. Polar, positively charged residues:
  His, Arg, Lys; Ornithine (Orn)
IV. Large, aliphatic, nonpolar residues:
  Met, Leu, Ile, Val, Cys, Norleucine (Nle), homocysteine
V. Large, aromatic residues:
  Phe, Tyr, Trp, acetyl phenylalanine As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "pegylated" and like terms refers to a compound that has been modified from its native state by linking a polyethylene glycol polymer to the compound. A "pegylated glucagon peptide" is a glucagon peptide that has a PEG chain covalently bound to the glucagon peptide.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

As used herein the term "pH stabilized glucagon peptide" refers to a glucagon analog that exhibits superior stability and solubility, relative to native glucagon, in aqueous buffers in the broadest pH range used for pharmacological purposes.

As used herein the term "charged amino acid" refers to an amino acid that comprises a side chain that is negatively charged (i.e., de-protonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

Non-naturally occurring amino acids refer to amino acids that do not naturally occur in vivo but which, nevertheless, can be incorporated into the peptide structures described herein. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from other amino acids.

As used herein the term "acidic amino acid" refers to an amino acid that comprises a second acidic moiety, including for example, a carboxylic acid or sulfonic acid group.

The term "alkyl" refers to a linear or branched hydrocarbon containing the indicated number of carbon atoms. Exemplary alkyls include methyl, ethyl, and linear propyl groups.

The term "heteroalkyl" refers to a linear or branched hydrocarbon containing the indicated number of carbon atoms and at least one heteroatom in the backbone of the structure. Suitable heteroatoms for purposes herein include but are not limited to N, S, and O.

As used herein a pyridyl-alanine is a generic term that encompasses 3-(2-Pyridyl)-L-alanine (2-Pal), 3-(3-Pyridyl)-L-alanine (3-Pal) and 3-(4-Pyridyl)-L-alanine (4-Pal). In one embodiment the pyridyl-alanine used in accordance with the present disclosure has the following structure:

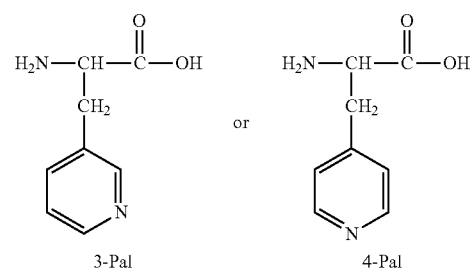

Embodiments

As disclosed herein glucagon peptides are provided that have pharmacokinetic and pharmacodynamics profiles comparable to native hormone but with solubility at physiological pH and chemical stability, once commercially formulated, to constitute a ready-to-use medicine. In one embodiment glucagon peptides having enhanced solubility and activity at the GLP-1 or GIP receptors are also provided. The enhanced solubility is derived from the discovery that aromatic amino acids present in the glucagon amino acid sequence can be substituted with pyridyl-alanine, or amino acids in the carboxy terminus can be substituted with amino acids in the D isomer conformation, to enhance solubility at physiological pH, while retaining the activity of the parent peptide.

In accordance with one embodiment an enhanced soluble analog of glucagon is provided wherein the analog comprises one or more amino acid substitutions with pyridyl-alanine at positions selected from 6, 10 or 13. In one embodiment a single amino acid selected from amino acids at positions 6, 10 or 13 is substituted with pyridyl-alanine. In one embodiment an amino acid selected from amino acids at positions 6 and/or 10 is substituted with pyridyl-alanine. In one embodiment an amino acid selected from amino acids at positions 10 and/or 13 is substituted with pyridyl-alanine.

In accordance with one embodiment a glucagon analog of SEQ ID NO: 1 is provided that differs from SEQ ID NO: 1 by 1, 2, or 3 amino acid substitutions of pyridyl-alanine at position 6, 10 or 13 relative to the native sequence of glucagon. In one embodiment a glucagon peptide having improved solubility relative to native glucagon while retaining activity at the glucagon receptor is provided, wherein the glucagon peptide comprises the sequence (SEQ ID NO: 934)
$X_1X_2X_3GTX_6TSDX_{10}SX_{12}X_{13}LX_{15}X_{16}X_{17}X_{18}AX_{20}X_{21}FVX_{24}WLX_{27}-Z$ wherein $X_1$ is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_3$ is an amino acid comprising a side chain of Structure I, II, or III:

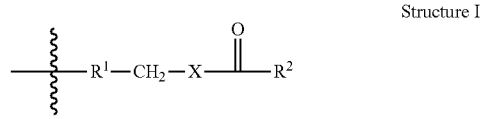

Structure I

Structure II

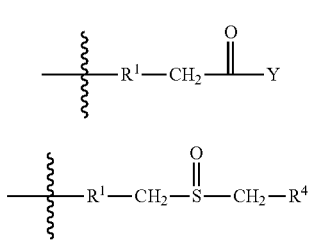

Structure III wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$;

$X_6$ is Phe or pyridyl-alanine;

$X_{10}$ is selected from the group consisting of Tyr, Lys and pyridyl-alanine;

$X_{12}$ is Lys, Ile or Arg;

$X_{13}$ is Tyr or pyridyl-alanine;

$X_{15}$ is Asp, Glu, cysteic acid, homoglutamic acid or homocysteic acid;

$X_{16}$ is Glu, Lys, Asp, Ser, glutamine, homoglutamic acid, homocysteic acid, Thr or Aib;

$X_{17}$ is Arg or Gln;

$X_{18}$ is Ala or Arg;

$X_{20}$ is Gln, Glu, Ser, Thr, Ala, Lys, Citrulline, Arg, Orn, or Aib;

$X_{21}$ is Glu, Aib, Asp, Lys, Cys, Orn, homocysteine or acetyl phenylalanine;

$X_{24}$ is Asn, Aib, Gln, Glu or Lys;

$X_{27}$ is Met, Leu or Nle;

$X_{28}$ is Asn or Ala;

$X_{29}$ is Thr or Gly; and

Z is selected from the group consisting of —COOH, —$X_{28}$—COOH, $X_{28}$—$X_{29}$—COOH, and $X_{28}$—$X_{29}$-GPSS-GAPPPS (SEQ ID NO: 953, with the proviso that at least one of $X_6$, $X_{10}$ or $X_{13}$ is pyridyl-alanine. In one embodiment the pyridyl-alanine is 3-(3-Pyridyl)-L-alanine. In one embodiment the pyridyl-alanine is 3-(4-Pyridyl)-L-alanine. In one embodiment X3 is glutamine. In a further embodiment the glucagon peptide has the sequence of SEQ ID NO: 934 and further comprises (i) a lactam bridge between the side chains of amino acids at positions i and i+4, wherein i is 12, 16, 20 or 24, or (ii) one, two, three, or all of the amino acids at positions 16, 20, 21, and 24 of the glucagon peptide is substituted with an α, α-disubstituted amino acid.

In one embodiment the glucagon peptide comprises the sequence (SEQ ID NO: 979)
$X_1X_2QGTX_6TSDX_{10}SX_{12}X_{13}LDX_{16}RRAQDFVQWLX_{27}NT$ wherein $X_1$ is selected from the group consisting of His, D-His, N-methyl-His, alpha-methyl-His, imidazole acetic acid, desamino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe or pyridyl-alanine;

$X_{10}$ is selected from the group consisting of Tyr, Lys and pyridyl-alanine;

$X_{12}$ is Lys, Ile or Arg;

$X_{13}$ is Tyr or pyridyl-alanine;

$X_{16}$ is Aib; and $X_{27}$ is Met, Leu or Nle, with the proviso that at least one of $X_6$, $X_{10}$ or $X_{13}$ is pyridyl-alanine. In one embodiment the pyridyl-alanine is 3-(3-Pyridyl)-L-alanine. In one embodiment the pyridyl-alanine is 3-(4-Pyridyl)-L-alanine. In one embodiment $X_3$ is glutamine. In one embodiment a glucagon peptide comprising SEQ ID NO: 979 is provided wherein $X_1$ is His, $X_2$ is Ser, D-Ser or Aib, $X_6$ is Phe or pyridyl-alanine, $X_{10}$ is pyridyl-alanine, $X_{12}$ is Lys, $X_{13}$ is Tyr or pyridyl-alanine, $X_{16}$ is Aib, and $X_{27}$ is Met, Leu or Nle.

The solubility of the pyridyl-alanine substituted glucagon peptides disclosed herein can be further modified by introducing charge at its carboxy terminus to additionally enhance the solubility of the peptide while retaining the agonist properties of the peptide. The enhanced solubility of the present analogs allows for the preparation and storage of glucagon solutions at near neutral pH. Formulating glucagon solutions at relatively neutral pHs (e.g. pH of about 6.0 to about 8.0) improves the long term stability of the glucagon peptides.

Accordingly, one embodiment of the present invention is directed to a glucagon peptide that has been modified relative to the wild type peptide of His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1) to improve the peptide's solubility in aqueous solutions, particularly at a pH ranging from about 5.5 to about 8.0, while retaining the native peptide's biological activity. In one embodiment an aromatic amino acid at position 6, 10 or 13 is substituted with pyridyl-alanine, and optionally charge is added to the peptide by the substitution of native non-charged amino acids with charged amino acids selected from the group consisting of lysine, arginine, histidine, aspartic acid and glutamic acid, or by the addition of charged amino acids to the amino or carboxy terminus of the peptide. Surprisingly, applicants have discovered that substituting the normally occurring amino acid at position 6, 10 or 13 with pyridyl-alanine, and optionally substitution of position 28 and/or 29 with charged amino acids, and/or the addition of one to two charged amino acids at the carboxy terminus of the glucagon peptide, enhances the solubility and stability of the glucagon peptides in aqueous solutions at physiologically relevant pHs (i.e., a pH of about 6.5 to about 7.5) by at least 5-fold and by as much as 30-fold.

Accordingly, glucagon peptides of one embodiment of the invention retain glucagon activity and exhibit at least 2-fold, 5-fold, 10-fold, 15-fold, 25-fold, 30-fold or greater solubility relative to native glucagon at a given pH between about 5.5 and 8, e.g., pH 7, when measured after 24 hours at 25° C. Any of the glucagon peptides disclosed herein may additionally exhibit improved stability at a pH within the range of 5.5 to 8, for example, retaining at least 75%, 80%, 90%, 95%, 96%, 97%, 98% or 99% of the original peptide after 24 hours at 25° C. In some embodiments, the glucagon peptides of the invention exhibit improved stability, such that at least 75% (e.g., at least 80%, at least 85%, at least 90%, at least 95%, more than 95%, up to 100%) of a concentration of the peptide or less than about 25% (e.g., less than 20%, less than 15%, less than 10%, less than 5%, 4%, 3%, 2%, 1%, down to 0%) of degraded peptide is detectable at 280 nm by an ultraviolet (UV) detector after about 1 or more weeks (e.g., about 2 weeks, about 4 weeks, about 1 month, about two months, about four months, about six months, about eight months, about ten months, about twelve months) in solution at a temperature of at least 20° C. (e.g., 21° C., 22° C., 23° C., 24° C., 25° C., 26° C., at least 27.5° C., at least 30° C., at least 35° C., at least 40° C., at least 50° C.) and less than 100° C., less than 85° C., less than 75° C., or less than 70° C. The glucagon peptides may include additional modifications that alter its pharmaceutical properties, e.g. increased potency, prolonged half-life in circulation, increased shelf-life, reduced precipitation or aggregation, and/or reduced degradation, e.g., reduced occurrence of cleavage or chemical modification after storage.

In a further embodiment an analog of SEQ ID NO: 935 is provided wherein the amino acid at position 28 and/or 29 is substituted with a charged amino acid and/or one to two charged amino acids are added at the carboxy terminus of the glucagon peptide. In one embodiment the charged amino acid is selected from the group consisting of Asp, Glu, and Lys. In accordance with one embodiment the analog of SEQ ID NO: 935 further comprises a C-terminal extension of SEQ ID NO: 820 (GPSSGAPPPS), SEQ ID NO: 821 (KRNRNNIA) or SEQ ID NO: 822 (KRNR) linked to amino acid 29 of the glucagon peptide.

In one embodiment a glucagon peptide having improved solubility relative to native glucagon while retaining activity at the glucagon receptor is provided, wherein the glucagon peptide comprises the sequence (SEQ ID NO: 954)
$X_1X_2QGTX_6TSDX_{10}SX_{12}X_{13}LDX_{16}RRAX_{20}X_{21}FVQWLX_{27}$-Z wherein $X_1$ is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe or pyridyl-alanine;

$X_{10}$ is selected from the group consisting of His, Tyr, Lys and pyridyl-alanine;

$X_{12}$ is Lys, Ile or Arg;

$X_{13}$ is His, Tyr or pyridyl-alanine;

$X_{16}$ is Aib;

$X_{20}$ is dGln, Gln, Glu or Aib;

$X_{21}$ is dAsp, Glu, Aib, or Asp;

$X_{27}$ is Met, Leu or Nle;

$X_{28}$ is Asp, Asn or Ala;

$X_{29}$ is Glu, Thr or Gly; and

Z is selected from the group consisting of —COOH, —$X_{28}$—COOH, $X_{28}$—$X_{29}$—COOH, and $X_{28}$—$X_{29}$-GPSSGAPPPS (SEQ ID NO: 953), with the proviso that at least one of $X_6$, $X_{10}$ or $X_{13}$ is pyridyl-alanine. In one embodiment the pyridyl-alanine is 3-(3-Pyridyl)-L-alanine. In one embodiment the pyridyl-alanine is 3-(4-Pyridyl)-L-alanine. In one embodiment the peptide of SEQ ID NO: 954 is provided wherein $X_1$ is His;

$X_2$ is Aib or Ser;

$X_6$ is Phe, 3-(3-Pyridyl)-L-alanine or 3-(4-Pyridyl)-L-alanine;

$X_{10}$ is selected from the group consisting of Tyr, 3-(3-Pyridyl)-L-alanine and 3-(4-Pyridyl)-L-alanine;

$X_{12}$ is Lys;

$X_{13}$ is Tyr, 3-(3-Pyridyl)-L-alanine or 3-(4-Pyridyl)-L-alanine;

$X_{16}$ is Aib;

$X_{20}$ is dGln, or Gln;

$X_{21}$ is dAsp or Asp;

$X_{27}$ is Met, Leu or Nle;

$X_{28}$ is Asp, Asn or Ala;

$X_{29}$ is Glu, Thr or Gly; and

Z is selected from the group consisting of $X_{28}$—$X_{29}$—COOH, and $X_{28}$—$X_{29}$-GPSSGAPPPS (SEQ ID NO: 953), with the proviso that at least one of $X_{10}$ or $X_{13}$ is 3-(3-Pyridyl)-L-alanine or 3-(4-Pyridyl)-L-alanine. In one embodiment at least one of $X_{10}$ or $X_{13}$ is 3-(3-Pyridyl)-L-alanine.

In one embodiment the glucagon peptide comprises the sequence (SEQ ID NO: 955)
$X_1X_2QGTX_6TSDX_{10}SKX_{13}LDX_{16}RRAX_{20}DFVQWLX_{27}NT$ wherein $X_1$ is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe or pyridyl-alanine;

$X_{10}$ is selected from the group consisting of Tyr and pyridyl-alanine;

$X_{13}$ is Tyr or pyridyl-alanine;

$X_{16}$ is Aib;

$X_{20}$ is dGln or Gln; and $X_{27}$ is Met, Leu or Nle, with the proviso that at least one of $X_6$, $X_{10}$ or $X_{13}$ is pyridyl-alanine. In one embodiment the pyridyl-alanine is 3-(3-Pyridyl)-L-alanine. In one embodiment the pyridyl-alanine is 3-(4-Pyridyl)-L-alanine. In a further embodiment an analog of SEQ ID NO: 955 is provided wherein the amino acid at position 28 and/or 29 is substituted with a charged amino acid and/or one to two charged amino acids are added at the carboxy terminus of the glucagon peptide. In one embodiment the charged amino acid is selected from the group consisting of Asp, Glu, and Lys. In accordance with one embodiment the analog of SEQ ID NO: 955 further comprises a C-terminal extension of SEQ ID NO: 820 (GPSSGAPPPS), SEQ ID NO: 821 (KRNRNNIA) or SEQ ID NO: 822 (KRNR) linked to amino acid 29 of the glucagon peptide.

In one embodiment the glucagon peptide comprises the sequence (SEQ ID NO: 955)
$X_1X_2QGTX_6TSDX_{10}SKX_{13}LDX_{16}RRAX_{20}DFVQWLX_{27}NT$ wherein $X_1$ is selected from the group consisting of His, D-His, N-methyl-His, alpha-methyl-His, imidazole acetic acid, des-amino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe;

$X_{10}$ is selected from the group consisting of Tyr and pyridyl-alanine;

$X_{13}$ is Tyr or pyridyl-alanine;

$X_{16}$ is Aib;

$X_{20}$ is dGln; and $X_{27}$ is Met, Leu or Nle, optionally with the proviso that at least one of $X_{10}$ or $X_{13}$ is pyridyl-alanine. In one embodiment $X_1$ is His and $X_2$ is Aib. In one embodiment $X_1$ is His and $X_2$ is Ser.

In one embodiment a glucagon peptide having improved solubility relative to native glucagon is provided wherein the analog comprises the sequence $X_1X_2QGTX_6TSDX_{10}SKX_{13}LX_{15}X_{16}RRAX_{20}DFVX_{24}WLMX_{28}T$ (SEQ ID NO: 936)

wherein $X_1$ is selected from the group consisting of His, D-His, N-methyl-His, alpha-methyl-His, imidazole acetic acid, desamino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe or pyridyl-alanine;

$X_{10}$ is selected from the group consisting of Tyr, Lys and pyridyl-alanine;

$X_{13}$ is Tyr or pyridyl-alanine;

$X_{15}$ is Asp, Glu, cysteic acid, homoglutamic acid or homocysteic acid;

$X_{16}$ is Glu, Lys, Asp, Ser, glutamine, homoglutamic acid, homocysteic acid, Thr or Aib;

$X_{20}$ is Gln or Lys;

$X_{24}$ is Gln or Glu;

$X_{28}$ is Asn, Asp or Lys, with the proviso that at least one of $X_6$, $X_{10}$ or $X_{13}$ is pyridyl-alanine. In one embodiment an analog of SEQ ID NO: 936 is provided that differs from SEQ ID NO: 936 by 1 to 2 amino acid modifications, selected from positions 7, 11, 14, 17, 18, 19, 21, and 27, with the proviso that at least one of $X_6$, $X_{10}$ or $X_{13}$ is pyridyl-alanine. In one embodiment $X_1$ is His and $X_2$ is Aib. In one embodiment the side chains of the amino acids at positions 12 and 16, positions 16 and 20, positions 20 and 24, or positions 24 and 28 of the glucagon peptide are linked by covalent bonds. In another embodiment, one, two, three or all of positions 16, 20, 21, and 24 are substituted with Aib.

In one embodiment a glucagon peptide having improved solubility relative to native glucagon is provided wherein the analog comprises the sequence $X_1X_2X_3GTX_6TSDX_{10}SKX_{13}LDX_{16}RRAX_{20}DFVX_{24}WLMX_{28}X_{29}$ (SEQ ID NO: 937)

wherein $X_1$ is selected from the group consisting of His, D-His, N-methyl-His, alpha-methyl-His, imidazole acetic acid, desamino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_3$ is an amino acid comprising a side chain of Structure I:

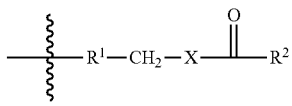

Structure I
wherein $R^1$ is $C_{0-3}$ alkyl or $C_{0-3}$ heteroalkyl; $R^2$ is $NHR^4$ or $C_{1-3}$ alkyl; $R^4$ is H or $C_{1-3}$ alkyl; and X is NH, O, or S;

$X_6$ is Phe or pyridyl-alanine;

$X_{10}$ is selected from the group consisting of Tyr, Lys and pyridyl-alanine;

$X_{13}$ is Tyr or pyridyl-alanine;

$X_{16}$ is amino isobutyric acid (Aib);

$X_{20}$ is Gln or Lys;

$X_{24}$ is Gln or Glu;

$X_{28}$ is Asn, Asp or Lys; and $X_{29}$ is Thr, Glu or Gly, optionally, Glu, with the proviso that at least one of $X_6$, $X_{10}$ or $X_{13}$ is pyridyl-alanine; or an analog thereof that comprises up to 10 amino acid modifications relative to the sequence of SEQ ID NO: 937, said modifications selected from the group consisting of a. substitution of Thr at position 7 with an amino acid lacking a hydroxyl group, optionally, Abu or Ile;
b. substitution of Tyr at position 10 with Phe or Val;
c. substitution of Lys at position 12 with Arg;
d. substitution of Asp at position 15 with Glu,
e. substitution of Gln at position 20 with Ala or Aib;
f. substitution of Asp at position 21 with Glu;
g. substitution of Gln at position 24 with Ala or Aib;
h. substitution of Met at position 27 with Leu or Nle;
i. addition of the amino acid sequence of GPSSGAPPPS (SEQ ID NO: 820) to the C-terminus, wherein the amino acid at position 29 is Thr or Gly,
j. substitution or addition of an amino acid comprising a side chain covalently attached to an acyl or alkyl group which is non-native to a naturally-occurring amino acid;
k. an insertion of 1-3 charged amino acids after position 29;

optionally, wherein the insertion comprises Glu or Lys; or a combination thereof, with the proviso that at least one of $X_6$, $X_{10}$ or $X_{13}$ is pyridyl-alanine. In one embodiment the pyridyl-alanine is 3-(3-Pyridyl)-L-alanine. In one embodiment the pyridyl-alanine is 3-(4-Pyridyl)-L-alanine. In one embodiment $X_3$ is glutamine. In one embodiment the sequence of SEQ ID NO: 936 or 937 is provided wherein the pyridyl-alanine is 3-(3-Pyridyl)-L-alanine. In one embodiment the sequence of SEQ ID NO: 936 or 937 is provided wherein the pyridyl-alanine is 3-(4-Pyridyl)-L-alanine. In one embodiment $X_3$ is glutamine In accordance with one embodiment a glucagon peptide with improved solubility relative to native glucagon and having activity at the glucagon receptor is provided wherein the analog comprises the sequence $X_1X_2QGTX_6TSDX_{10}SKX_{13}LDX_{16}RRAQDFVQWLMNT$ (SEQ ID NO: 935) wherein $X_1$ is selected from the group consisting of His, D-His, N-methyl-His, alpha-methyl-His, imidazole acetic acid, desamino-His, hydroxyl-His, acetyl-His, homo-His, or alpha, alpha-dimethyl imidiazole acetic acid (DMIA);

$X_2$ is selected from the group consisting of Ser, D-Ser, Ala, D-Ala, Gly, N-methyl-Ser, Aib, Val, or α-amino-N-butyric acid;

$X_6$ is Phe or pyridyl-alanine;

$X_{10}$ is selected from the group consisting of Tyr, Lys and pyridyl-alanine;

$X_{13}$ is Tyr or pyridyl-alanine;

$X_{16}$ is Aib, with the proviso that at least one of $X_6$, $X_{10}$ or $X_{13}$ is pyridyl-alanine. In one embodiment $X_1$ is DMIA and $X_2$ is serine. In one embodiment $X_1$ is His and $X_2$ is D-serine or Aib. In one embodiment $X_1$ is His and $X_2$ is Aib. In a further embodiment the glucagon peptide further comprises a C-terminal extension of SEQ ID NO: 820 (GPSSGAP-PPS), SEQ ID NO: 821 (KRNRNNIA) or SEQ ID NO: 822 (KRNR) linked to amino acid 29 of the glucagon peptide. In one embodiment the glucagon peptide further comprises a C-terminal extension of SEQ ID NO: 820 (GPSSGAPPPS).

In accordance with one embodiment a glucagon peptide with improved solubility relative to native glucagon and having activity at the glucagon receptor is provided wherein the analog comprises the sequence HX$_2$QGTX$_6$TSDYSKX$_{13}$LDSRRAQDFVQWLMNT (SEQ ID NO: 938) wherein X$_2$ is selected from the group consisting of Ser, D-Ser, Ala, D-Ala, Gly, N-methyl-Ser, Aib, Val, or α-amino-N-butyric acid;

X$_6$ is Phe or pyridyl-alanine; and

X$_{13}$ is Tyr or pyridyl-alanine.

In one embodiment a glucagon peptide having improved solubility is provided where the glucagon analog comprises the sequence (SEQ ID NO: 957)
HSQGTX$_6$TSDX$_{10}$SKX$_{13}$LDX$_{16}$RRAX$_{20}$X$_{21}$FVQWLMX$_{28}$X$_{29}$ wherein X$_6$ is selected from the group consisting of Phe, 3-Pal and 4-Pal;

X$_{10}$ is selected from the group consisting of Tyr, His, 3-Pal and 4-Pal;

X$_{13}$ is selected from the group consisting of Tyr, His, 3-Pal and 4-Pal;

X$_{16}$ is Aib;

X$_{20}$ is selected from the group consisting of dGln and Gln;

X$_{21}$ is selected from the group consisting of dAsp and Asp;

X$_{28}$ is Asn, Asp or Lys; and

X$_{29}$ is Thr, Gly, Asp, or Glu. In one embodiment, the glucagon peptide has the sequence of SEQ ID NO: 957 further comprises a C-terminal extension of SEQ ID NO: 820 (GPSSGAPPPS) linked to an amino acid at position 29 of the peptide. In one embodiment, the glucagon peptide has the sequence of SEQ ID NO: 957 wherein X$_6$ is Phe; X$_{10}$ is 3-Pal or 4-Pal; X$_{13}$ is Tyr, 3-Pal or 4-Pal; X$_{16}$ is Aib; X$_{20}$ is dGln; X$_{21}$ is Asp; X$_{28}$ is Asn and X$_{29}$ is Thr. In one embodiment, the glucagon peptide has the sequence of SEQ ID NO: 957 wherein X$_6$ is Phe; X$_{10}$ is 3-Pal or 4-Pal; X$_{13}$ is Tyr, 3-Pal or 4-Pal; X$_{16}$ is Aib; X$_{20}$ is Gln; X$_{21}$ is dAsp; X$_{28}$ is Asn and X$_{29}$ is Thr.

In one embodiment the glucagon peptide has the sequence of (SEQ ID NO: 959)
HSQGTFTSDX$_{10}$SKYLDX$_{16}$RRAX$_{20}$DFVQWLMNT wherein X$_{10}$ is 3-Pal or 4-Pal;

X$_{16}$ is Aib; and

X$_{20}$ is dGln.

In one embodiment the glucagon peptide has the sequence of (SEQ ID NO: 969)
HSQGTFTSDX$_{10}$SKX$_{13}$LDX$_{16}$RRAX$_{20}$DFVQWLMNT wherein X$_{10}$ is selected from the group consisting of 3-Pal and 4-Pal;

X$_{13}$ is selected from the group consisting of 3-Pal and 4-Pal;

X$_{16}$ is Aib; and

X$_{20}$ is dGln, optionally wherein X$_{10}$ and X$_{11}$ are both 3-Pal, optionally wherein X$_{10}$ and X$_{11}$ are both 4-Pal.

In one embodiment the glucagon peptide has the sequence of (SEQ ID NO: 959)
HSQGTFTSDX$_{10}$SKYLDX$_{16}$RRAX$_{20}$DFVQWLMNT wherein X$_{10}$ is selected from the group consisting of 3-Pal and 4-Pal;

X$_{16}$ is Aib; and

X$_{20}$ is dGln, optionally wherein X$_{10}$ is 3-Pal, optionally wherein X$_{10}$ is 4-Pal.

In one embodiment the glucagon peptide has the sequence of (SEQ ID NO: 960)
HSQGTX$_6$TSDX$_{10}$SKX$_{13}$LDX$_{16}$RRAX$_{20}$DFVQWLMX$_{28}$X$_{29}$ wherein X$_6$ is selected from the group consisting of 3-Pal and 4-Pal;

X$_{10}$ is selected from the group consisting of His, 3-Pal and 4-Pal;

X$_{13}$ is selected from the group consisting of His, 3-Pal and 4-Pal;

X$_{16}$ is Aib;

X$_{20}$ is dGln;

X$_{28}$ is Asn, Asp or Lys; and

X$_{29}$ is Gly, Asp, or Glu.

In accordance with one embodiment a glucagon peptide with improved solubility relative to native glucagon and having activity at the glucagon receptor is provided wherein the analog comprises a sequence selected from the group consisting of (SEQ ID NO: 961)
X$_1$X$_2$QGTX$_6$TSDYSKYLDSRRAQDFVQWLMNT;

(SEQ ID NO: 940)
X$_1$X$_2$QGTFTSDX$_{10}$SKYLDSRRAQDFVQWLMNT;

(SEQ ID NO: 941)
X$_1$X$_2$QGTFTSDYSKX$_{13}$LDSRRAQDFVQWLMNT;

(SEQ ID NO: 962)
X$_1$X$_2$QGTFTSDX$_{10}$SKX$_{13}$LDSRRAQDFVQWLMNT;
or (SEQ ID NO: 963)
X$_1$X$_2$QGTX$_6$TSDX$_{10}$SKX$_{13}$LDSRRAQDFVQWLMNT;

wherein

X$_1$ is selected from the group consisting of His, D-His, N-methyl-His, alpha-methyl-His, imidazole acetic acid, des-amino-His, hydroxyl-His, acetyl-His, homo-His, and alpha, alpha-dimethyl imidiazole acetic acid (DMIA);

X$_2$ is selected from the group consisting of Ser, D-Ser, Ala, D-Ala, Gly, N-methyl-Ser, Aib, Val, or α-amino-N-butyric acid;

X$_6$ is Phe or pyridyl-alanine;

X$_{10}$ is selected from the group consisting of Tyr, Lys and pyridyl-alanine;

X$_{13}$ is Tyr or pyridyl-alanine. In one embodiment X$_1$ is DMIA and X$_2$ is serine.

In one embodiment X₁ is His and X₂ is D-serine or Aib. In one embodiment X₁ is His and X₂ is Aib. In a further embodiment the glucagon peptide further comprises a C-terminal extension of SEQ ID NO: 820 (GPSSGAPPPS), SEQ ID NO: 821 (KRNRNNIA) or SEQ ID NO: 822 (KRNR) linked to amino acid 29 of the glucagon peptide. In one embodiment the glucagon peptide further comprises a C-terminal extension of SEQ ID NO: 820 (GPSSGAPPPS). In one embodiment the sequence of SEQ ID NO: 938, 939 or 940 is provided wherein the pyridyl-alanine is 3-(3-Pyridyl)-L-alanine. In one embodiment the sequence of SEQ ID NO: 936 or 937 is provided wherein the pyridyl-alanine is 3-(4-Pyridyl)-L-alanine. In one embodiment X₃ is glutamine Further Modifications and Combinations Additional modifications may be made to the glucagon peptide which may further increase solubility and/or stability and/or glucagon activity. The glucagon peptide may alternatively comprise other modifications that do not substantially affect solubility or stability, and that do not substantially decrease glucagon activity. In exemplary embodiments, the glucagon peptide may comprise a total of 1, up to 2, up to 3, up to 4, up to 5, up to 6, up to 7, up to 8, up to 9, or up to 10, or up to 11, or up to 12, or up to 13, or up to 14 amino acid modifications relative to the native glucagon sequence. In some embodiments, such glucagon analogs retain at least 22, 23, 24, 25, 26, 27 or 28 of the naturally occurring amino acids at the corresponding positions in native glucagon (e.g. have 1-7, 1-5 or 1-3 modifications relative to naturally occurring glucagon).

In some embodiments 1, 2, 3, 4 or 5 non-conservative substitutions are carried out at any of positions 2, 5, 7, 11, 12, 14, 17, 18, 19, 20, 21, 24, 27, 28 or 29 and up to 5 further conservative substitutions are carried out at any of these positions relative to native glucagon. In some embodiments 1, 2, or 3 amino acid modifications are carried out within amino acids at positions 1-16, and 1, 2 or 3 amino acid modifications are carried out within amino acids at positions 17-26.

Exemplary modifications include but are not limited to:

(a) non-conservative substitutions, conservative substitutions, additions or deletions while retaining at least partial glucagon agonist activity, for example, conservative substitutions at one or more of positions 2, 5, 7, 11, 12, 14, 16, 17, 18, 19, 20, 21, 24, 27, 28 or 29, substitution of Tyr at position 10 with Val or Phe, substitution of Lys at position 12 with Arg, substitution of one or more of these positions with Ala;

(b) deletion of amino acids at positions 29 and/or 28, and optionally position 27, while retaining at least partial glucagon agonist activity;

(c) modification of the aspartic acid at position 15, for example, by substitution with glutamic acid, homoglutamic acid, cysteic acid or homocysteic acid, which may reduce degradation; or modification of the serine at position 16, for example, by substitution of threonine, Aib, glutamic acid or with another negatively charged amino acid having a side chain with a length of 4 atoms, or alternatively with any one of glutamine, homoglutamic acid, or homocysteic acid, which likewise may reduce degradation due to cleavage of the Asp15-Ser16 bond;

(d) addition of a hydrophilic moiety such as the water soluble polymer polyethylene glycol, as described herein, e.g. at position 16, 17, 20, 21, 24, 29, 40 or at the C-terminal amino acid, which may increase solubility and/or half-life;

(e) modification of the methionine at position 27, for example, by substitution with leucine or norleucine, to reduce oxidative degradation;

(f) modification of the Gln at position 20 or 24, e.g. by substitution with Ser, Thr, Ala or Aib, to reduce degradation that occurs through deamidation of Gln (g) modification of Asp at position 21, e.g. by substitution with Glu, to reduce degradation that occurs through dehydration of Asp to form a cyclic succinimide intermediate followed by isomerization to iso-aspartate;

(h) modifications at position 1 or 2 as described herein that improve resistance to DPP-IV cleavage, optionally in combination with an intramolecular bridge such as a lactam bridge between positions "i" and "i+4", wherein i is an integer from 12 to 25, e.g., 12, 16, 20, 24;

(i) acylating or alkylating the glucagon peptide as described herein, which may increase the activity at the glucagon and GLP-1 receptors, increase half-life in circulation and/or extending the duration of action and/or delaying the onset of action, optionally combined with addition of a hydrophilic moiety, additionally or alternatively, optionally combined with a modification which selectively reduces activity at the GLP-1 peptide, e.g., a modification of the Thr at position 7, such as a substitution of the Thr at position 7 with an amino acid lacking a hydroxyl group, e.g., Abu or Ile; deleting amino acids C-terminal to the amino acid at position 27 (e.g., deleting one or both of the amino acids at positions 28 and 29, yielding a peptide 27 or 28 amino acids in length); or a combination thereof.

(j) C-terminal extensions as described herein;

(k) homodimerization or heterodimerization as described herein; and combinations of the above.

Exemplary modifications include at least one amino acid modification selected from Group A and one or more amino acid modifications selected from Group B and/or Group C, wherein Group A is:

substitution of Asn at position 28 with a charged amino acid;

substitution of Asn at position 28 with a charged amino acid selected from the group consisting of Lys, Arg, His, Asp, Glu, cysteic acid, and homocysteic acid;

substitution at position 28 with Asn, Asp, or Glu;

substitution at position 28 with Asp;

substitution at position 28 with Glu;

substitution of Thr at position 29 with a charged amino acid;

substitution of Thr at position 29 with a charged amino acid selected from the group consisting of Lys, Arg, His, Asp, Glu, cysteic acid, and homocysteic acid;

substitution at position 29 with Asp, Glu, or Lys;

substitution at position 29 with Glu;

insertion of 1-3 charged amino acids after position 29;

insertion after position 29 of Glu or Lys;

insertion after position 29 of Gly-Lys or Lys-Lys;

or combinations thereof;

wherein Group B is:

substitution of Asp at position 15 with Glu;

substitution of Ser at position 16 with Thr or Aib; and wherein Group C is:

substitution of His at position 1 with a non-native amino acid that reduces susceptibility of the glucagon peptide to cleavage by dipeptidyl peptidase IV (DPP-IV), substitution of Ser at position 2 with a non-native amino acid that reduces susceptibility of the glucagon peptide to cleavage by dipeptidyl peptidase IV (DPP-IV), substitution of Lys at position 12 with Arg;

substitution of Gln at position 20 with Ala or Aib;

substitution of Asp at position 21 with Glu;
substitution of Gln at position 24 with Ala or Aib;
substitution of Met at position 27 with Leu or Nle;
deletion of amino acids at positions 27-29;
deletion of amino acids at positions 28-29;
deletion of the amino acid at positions 29;
or combinations thereof.

Modifications at Position 3

Glucagon receptor activity can be reduced by an amino acid modification at position 3, e.g. substitution of the naturally occurring glutamine at position 3, with an acidic, basic, or a hydrophobic amino acid. For example substitution at position 3 with glutamic acid, ornithine, or norleucine substantially reduces or destroys glucagon receptor activity.

Maintained or enhanced activity at the glucagon receptor may be achieved by modifying the Gln at position 3 with a glutamine analog. For example, a glucagon peptide comprising a glutamine analog at position 3 may exhibit about 5%, about 10%, about 20%, about 50%, or about 85% or greater the activity of native glucagon (SEQ ID NO: 1) at the glucagon receptor. In some embodiments a glucagon peptide comprising a glutamine analog at position 3 may exhibit about 20%, about 50%, about 75%, about 100%, about 200% or about 500% or greater the activity, of a corresponding glucagon peptide having the same amino acid sequence as the peptide comprising the glutamine analog, except for the modified amino acid at position 3 (e.g. SEQ ID NO: 877). In some embodiments, a glucagon peptide comprising a glutamine analog at position 3 exhibits enhanced activity at the glucagon receptor, but the enhanced activity is no more than 1000%, 10,000%, 100,000%, or 1,000,000% of the activity of native glucagon or of a corresponding glucagon peptide having the same amino acid sequence as the peptide comprising the glutamine analog, except for the modified amino acid at position 3.

In some embodiments, the glutamine analog is a naturally occurring or a non-naturally occurring amino acid comprising a side chain of Structure I, II or III:

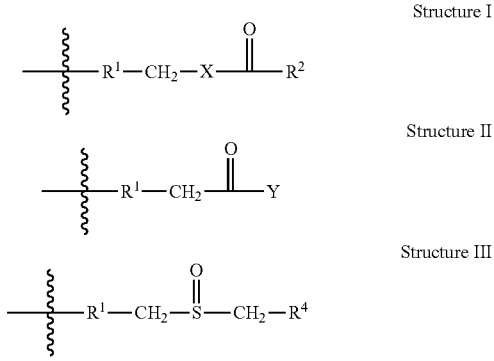

Structure I

Structure II

Structure III wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R^1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl. In exemplary embodiments, an amino acid comprising a side chain of Structure I is provided where, $R_1$ is $CH_2$—S, X is NH, and $R^2$ is $CH_3$ (acetamidomethyl-cysteine, C(Acm)); $R^1$ is $CH_2$, X is NH, and $R^2$ is $CH_3$ (acetyldiaminobutanoic acid, Dab(Ac)); $R^1$ is $C_0$ alkyl, X is NH, $R^2$ is $NHR_4$, and $R^4$ is H (carbamoyldiaminopropanoic acid, Dap(urea)); or $R_1$ is $CH_2$—$CH_2$, X is NH, and $R^2$ is $CH_3$ (acetylornithine, Orn (Ac)). In exemplary embodiments, an amino acid comprising a side chain of Structure II is provided where, $R^1$ is $CH_2$, Y is $NHR^4$, and $R^4$ is $CH_3$ (methylglutamine, Q(Me)); In exemplary embodiments, an amino acid comprising a side chain of Structure III is provided where, $R_1$ is $CH_2$ and $R^4$ is H (methionine-sulfoxide, M(O)); In specific embodiments, the amino acid at position 3 is substituted with Dab(Ac). For example, glucagon peptides comprising a modified amino acid at position 3 (relative to native glucagon) can comprise the amino acid sequence of SEQ ID NO: 594, SEQ ID NO: 595, SEQ ID NO: 596, SEQ ID NO: 597, SEQ ID NO: 598, and SEQ ID NO: 599.

Enhanced activity at the GLP-1 receptor is provided by replacing the carboxylic acid of the C-terminal amino acid with a charge-neutral group, such as an amide or ester. Conversely, retaining the native carboxylic acid at the C-terminus of the peptide maintains the relatively greater selectivity of the glucagon peptide for glucagon receptor vs. GLP-1 receptor (e.g., greater than about 5, 6, 7, 8, 9, 10, 11, 12, 13, 14, 15, 16, 17, 18, 19, or 20-fold).

DPP-IV Resistance

In some embodiments the glucagon peptides disclosed herein are further modified at position 1 or 2 to reduce susceptibility to cleavage by dipeptidyl peptidase IV. More particularly, in some embodiments, position 1 of the analog peptide is substituted with an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine.

More particularly, in some embodiments, position 2 of the analog peptide is substituted with an amino acid selected from the group consisting of D-serine, D-alanine, valine, amino N-butyric acid, glycine, N-methyl serine and aminoisobutyric acid. In one embodiment position 2 of the analog peptide is substituted with an amino acid selected from the group consisting of D-serine, D-alanine, glycine, N-methyl serine and aminoisobutyric acid. In another embodiment position 2 of the analog peptide is substituted with an amino acid selected from the group consisting of D-serine, glycine, and aminoisobutyric acid.

Where substitutions or modifications or derivatization at positions 1 or 2 reduce activity at the glucagon receptor, an intramolecular bridge in the C-terminal portion (amino acids 12-29) of the peptide (e.g., a lactam bridge between side chains of amino acids at positions "i" and "i+4", wherein i is an integer from 12 to 25), can improve glucagon activity at the glucagon receptor.

Addition of Hydrophilic Moieties

Hydrophilic moieties such as PEG groups can be attached to the glucagon peptides under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In a specific aspect of the invention, an amino acid residue on the glucagon peptide having a thiol is modified with a hydrophilic moiety such as PEG. In some embodiments, the thiol is modified with maleimide-activated PEG in a Michael addition reaction to result in a PEGylated peptide comprising the thioether linkage shown below:

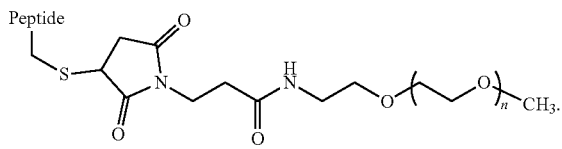

In some embodiments, the thiol is modified with a haloacetyl-activated PEG in a nucleophilic substitution reaction to result in a PEGylated peptide comprising the thioether linkage shown below:

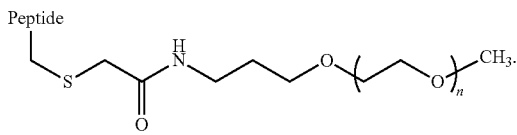

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly ((β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The polyethylene glycol chain in accordance with some embodiments has a molecular weight selected from the range of about 500 to about 40,000 Daltons. In one embodiment the polyethylene glycol chain has a molecular weight selected from the range of about 500 to about 5,000 Daltons, or about 1,000 to about 5,000 Daltons. In another embodiment the polyethylene glycol chain has a molecular weight of about 10,000 to about 20,000 Daltons. In yet other exemplary embodiments the polyethylene glycol chain has a molecular weight of about 20,000 to about 40,000 Daltons.

Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

Acylation

In accordance with one embodiment, the glucagon peptide is modified to comprise an acyl group, e.g., an acyl group which is not naturally-occurring on an amino acid (e.g., an acyl group which is non-native to a naturally-occurring amino acid). The addition of an acyl group causes the peptide to have one or more of a prolonged half-life in circulation, a delayed onset of action, an extended duration of action, an improved resistance to proteases, such as DPP-IV, and increased potency at the GLP-1 and glucagon receptors. As shown herein, acylation of the glucagon peptide does not lead to decreased activity at the glucagon and GLP-1 receptors. Rather, in some instances, acylation actually increases the activity at the GLP-1 and glucagon receptors. Accordingly, the potency of the acylated analogs is comparable to the unacylated versions of the glucagon co-agonist analogs, if not enhanced.

In accordance with one embodiment, the glucagon peptide is modified to comprise an acyl group which is attached to the glucagon peptide via an ester, thioester, or amide linkage for purposes of prolonging half-life in circulation and/or delaying the onset of and/or extending the duration of action and/or improving resistance to proteases such as DPP-IV.

Acylation can be carried out at any position within the glucagon peptide, including any of positions 1-29, a position within a C-terminal extension, or the C-terminal amino acid, provided that glucagon and/or GLP-1 activity is retained, if not enhanced. Nonlimiting examples include positions 5, 7, 10, 11, 12, 13, 14, 16, 17, 18, 19, 20, 21, 24, 27, 28, or 29. In specific embodiments, acylation occurs at position 10 of the glucagon peptide and the glucagon peptide lacks an intramolecular bridge, e.g., a covalent intramolecular bridge (e.g., a lactam bridge). Such acylated peptides lacking an intramolecular bridge demonstrate enhanced activity at the GLP-1 and glucagon receptors as compared to the corresponding non-acylated peptides lacking a covalent intramolecular bridge and in comparison to the corresponding peptides lacking an intramolecular bridge acylated at a position other than position 10. As shown herein, acylation at position 10 can even transform a glucagon peptide having little activity at the glucagon receptor to a glucagon peptide having activity at both the glucagon and GLP-1 receptors. Accordingly, the position at which acylation occurs can alter the overall activity profile of the glucagon peptide.

Glucagon peptides may be acylated at the same amino acid position where a hydrophilic moiety is linked, or at a different amino acid position. Nonlimiting examples include acylation at position 10 and pegylation at one or more positions in the C-terminal portion of the glucagon peptide, e.g., position 24, 28 or 29, within a C-terminal extension, or at the C-terminus (e.g., through adding a C-terminal Cys).

The acyl group can be covalently linked directly to an amino acid of the glucagon peptide, or indirectly to an amino acid of the glucagon peptide via a spacer, wherein the spacer is positioned between the amino acid of the glucagon peptide and the acyl group.

In a specific aspect of the invention, the glucagon peptide is modified to comprise an acyl group by direct acylation of an amine, hydroxyl, or thiol of a side chain of an amino acid of the glucagon peptide. In some embodiments, the glucagon peptide is directly acylated through the side chain amine, hydroxyl, or thiol of an amino acid. In some embodiments, acylation is at position 10, 20, 24, or 29. In this regard, the acylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments of the invention, the direct acylation of the glucagon peptide occurs through the side chain amine, hydroxyl, or thiol of the amino acid at position 10.

In some embodiments, the amino acid comprising a side chain amine is an amino acid of Formula I:

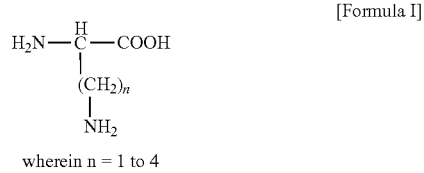

[Formula I]

wherein n = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

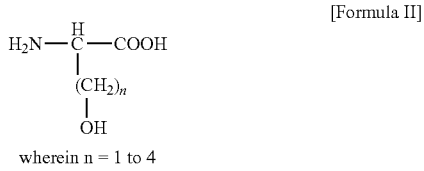

[Formula II]

wherein n = 1 to 4

In some exemplary embodiments, the amino acid of Formula II is the amino acid wherein n is 1 (Ser).

In yet other embodiments, the amino acid comprising a side chain thiol is an amino acid of Formula III:

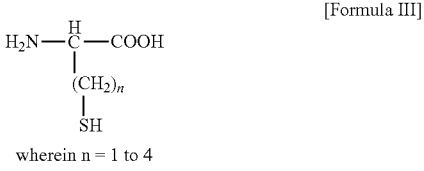

[Formula III]

wherein n = 1 to 4

In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In one embodiment of the invention, the acylated glucagon peptide comprises a spacer between the peptide and the acyl group. In some embodiments, the glucagon peptide is covalently bound to the spacer, which is covalently bound to the acyl group.

The amino acid to which the spacer is attached can be any amino acid (e.g., a singly α-substituted amino acid or an α,α-disubstituted amino acid) comprising a moiety which permits linkage to the spacer. For example, an amino acid comprising a side chain $NH_2$, —OH, or —COOH (e.g., Lys, Orn, Ser, Asp, or Glu) is suitable. In this respect, the acylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the amino acid of the spacer can be an acidic residue, e.g., Asp and Glu.

In the instance in which the side chain amine of the amino acid of the spacer is acylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be acylated, such that the glucagon peptide is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In specific embodiments, the spacer comprises an amino poly (alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Kans.).

In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate, and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C12 to C18 fatty acyl group, e.g., C14 fatty acyl group, C16 fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms.

In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine ((β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (MeVal), and alkylated 3-mercaptopropionic acid.

In some embodiments, the spacer comprises an overall negative charge, e.g., comprises one or two negatively charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

In some exemplary embodiments, the glucagon peptide is modified to comprise an acyl group by acylation of an amine, hydroxyl, or thiol of a spacer, which spacer is attached to a side chain of an amino acid at position 10, 20, 24, or 29, or at the C-terminal amino acid of the glucagon peptide.

In yet more specific embodiments, the acyl group is attached to the amino acid at position 10 of the glucagon peptide and the length of the spacer and acyl group is 14 to 28 atoms. The amino acid at position 10, in some aspects, is an amino acid of Formula I, e.g., Lys, or a disubstituted amino acid related to Formula I. In more specific embodiments, the glucagon peptide lacks an intramolecular bridge, e.g., a covalent intramolecular bridge. The glucagon peptide, for example, can be a peptide comprising one or more alpha, alpha-disubstituted amino acids, e.g., Aib, for stabilizing the alpha helix of the peptide. As shown herein, such peptides comprising an acylated spacer covalently attached to the side chain of the amino acid at position 10 exhibit enhanced potency at both the GLP-1 and glucagon receptors.

Suitable methods of peptide acylation via amines, hydroxyls, and thiols are known in the art. See, for example, (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem.* "Chemical Modifications of Proteins: History and Applications" pages 1, 2-12 (1990); Hashimoto et al., *Pharmacuetical Res.* "Synthesis of Palmitoyl Derivatives of Insulin and their Biological Activity" Vol. 6, No: 2 pp. 171-176 (1989).

The acyl group of the acylated glucagon peptide can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In some embodiments of the invention, the glucagon peptide is modified to comprise an acyl group by acylation of a long chain alkane by the glucagon peptide. In specific aspects, the long chain alkane comprises an amine, hydroxyl, or thiol group (e.g. octadecylamine, tetradecanol, and hexadecanethiol) which reacts with a carboxyl group, or activated form thereof, of the glucagon peptide. The carboxyl group, or activated form thereof, of the glucagon peptide can be part of a side chain of an amino acid (e.g., glutamic acid, aspartic acid) of the glucagon peptide or can be part of the peptide backbone.

In certain embodiments, the glucagon peptide is modified to comprise an acyl group by acylation of the long chain alkane by a spacer which is attached to the glucagon peptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, amino acids, dipeptides, tripeptides, hydrophilic bifunctional spacers and hydrophobic bifunctional spacers.

As used herein, the term "activated form of a carboxyl group" refers to a carboxyl group with the general formula R(C=O)X, wherein X is a leaving group and R is the glucagon peptide or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects of the invention, in which a long chain alkane is acylated by the glucagon peptide or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, an amine, hydroxyl, or thiol group of the glucagon peptide is acylated with a cholesterol acid. In a specific embodiment, the glucagon peptide is linked to the cholesterol acid through an alkylated desamino Cys spacer, i.e., an alkylated 3-mercaptopropionic acid spacer.

The acylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon peptide can comprise SEQ ID NO: 1, including any of the modifications described herein, in which at least one of the amino acids at position 10, 20, 24, and 29 comprise an acyl group and at least one of the amino acids at position 16, 17, 21, 24, or 29, a position within a C-terminal extension, or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the acyl group is attached to position 10, optionally via a spacer comprising Cys, Lys, Orn, homo-Cys, or Ac-Phe, and the hydrophilic moiety is incorporated at a Cys residue at position 24.

Alternatively, the acylated glucagon peptide can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation

In accordance with some embodiments, the glucagon peptide is modified to comprise an alkyl group, e.g., an alkyl group which is not naturally-occurring on an amino acid (e.g., an alkyl group which is non-native to a naturally-occurring amino acid). Without being held to any particular theory, it is believed that alkylation of glucagon peptides will achieve similar, if not the same, effects as acylation of the glucagon peptides, e.g., a prolonged half-life in circulation, a delayed onset of action, an extended duration of action, an improved resistance to proteases, such as DPP-IV, and increased potency at the GLP-1 and glucagon receptors.

Alkylation can be carried out at any position within the glucagon peptide, including any of positions 1-29, a position within a C-terminal extension, or the C-terminal amino acid, provided that the glucagon activity is retained. Nonlimiting examples include positions 5, 7, 10, 11, 12, 13, 14, 16, 17, 18, 19, 20, 21, 24, 27, 28, or 29. The alkyl group can be covalently linked directly to an amino acid of the glucagon peptide, or indirectly to an amino acid of the glucagon peptide via a spacer, wherein the spacer is positioned between the amino acid of the glucagon peptide and the alkyl group. Glucagon peptides may be alkylated at the same amino acid position where a hydrophilic moiety is linked, or at a different amino acid position. Nonlimiting examples include alkylation at position 10 and pegylation at one or more positions in the C-terminal portion of the glucagon peptide, e.g., position 24, 28 or 29, within a C-terminal extension, or at the C-terminus (e.g., through adding a C-terminal Cys).

In a specific aspect of the invention, the glucagon peptide is modified to comprise an alkyl group by direct alkylation of an amine, hydroxyl, or thiol of a side chain of an amino acid of the glucagon peptide. In some embodiments, alkylation is at position 10, 20, 24, or 29. In this regard, the alkylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments of the invention, the direct alkylation of the glucagon peptide occurs through the side chain amine, hydroxyl, or thiol of the amino acid at position 10.

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula II is the amino acid wherein n is 1 (Ser).

In yet other embodiments, the amino acid comprising a side chain thiol is an amino acid of Formula III. In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In one embodiment of the invention, the alkylated glucagon peptide comprises a spacer between the peptide and the alkyl group. In some embodiments, the glucagon peptide is covalently bound to the spacer, which is covalently bound to the alkyl group. In some exemplary embodiments, the glucagon peptide is modified to comprise an alkyl group by alkylation of an amine, hydroxyl, or thiol of a spacer, which spacer is attached to a side chain of an amino acid at position 10, 20, 24, or 29 of the glucagon peptide. The amino acid to which the spacer is attached can be any amino acid (e.g., a singly α-substituted amino acid or an α,α-disubstituted amino acid) comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the glucagon peptide is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser.

When alkylation occurs through a thiol group of spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Kans.).

In some embodiments, the spacer is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate, and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic or hydrophobic bifunctional spacer) in specific embodiments is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a C12 to C18 alkyl group, e.g., C14 alkyl group, C16 alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl is 17 to 28 (e.g., 19 to 26, 19 to 21) atoms.

In accordance with certain foregoing embodiments, the bifunctional spacer can be a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer can be composed of naturally-occurring and/or non-naturally occurring amino acids, including, for example, any of the amino acids taught herein. In some embodiments, the spacer comprises an overall negative charge, e.g., comprises one or two negatively charged amino acids. In some embodiments, the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

Suitable methods of peptide alkylation via amines, hydroxyls, and thiols are known in the art. For example, a Williamson ether synthesis can be used to form an ether linkage between a hydroxyl group of the glucagon peptide and the alkyl group. Also, a nucleophilic substitution reaction of the peptide with an alkyl halide can result in any of an ether, thioether, or amino linkage.

The alkyl group of the alkylated glucagon peptide can be of any size, e.g., any length carbon chain, and can be linear or branched. In some embodiments of the invention, the alkyl group is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments of the invention, the glucagon peptide is modified to comprise an alkyl group by reacting a nucleophilic, long chain alkane with the glucagon peptide, wherein the glucagon peptide comprises a leaving group suitable for nucleophilic substitution. In specific aspects, the nucleophilic group of the long chain alkane comprises an amine, hydroxyl, or thiol group (e.g. octadecylamine, tetradecanol, and hexadecanethiol). The leaving group of the glucagon peptide can be part of a side chain of an amino acid or can be part of the peptide backbone. Suitable leaving groups include, for example, N-hydroxysuccinimide, halogens, and sulfonate esters.

In certain embodiments, the glucagon peptide is modified to comprise an alkyl group by reacting the nucleophilic, long chain alkane with a spacer which is attached to the glucagon peptide, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

With regard to these aspects of the invention, in which a long chain alkane is alkylated by the glucagon peptide or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, alkylation can occur between the glucagon peptide and a cholesterol moiety. For example, the hydroxyl group of cholesterol can displace a leaving group on the long chain alkane to form a cholesterol-glucagon peptide product.

The alkylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon peptide can comprise SEQ ID NO: 1 or a modified amino acid sequence thereof comprising one or more of the amino acid modifications described herein, in which at least one of the amino acids at position 10, 20, 24, and 29 comprise an alkyl group and at least one of the amino acids at position 16, 17, 21, 24, and 29, a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10, optionally via a spacer comprising Cys, Lys, Orn, homo-Cys, or Ac-Phe, and the hydrophilic moiety is incorporated at a Cys residue at position 24.

Alternatively, the alkylated glucagon peptide can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Modifications that Reduce GLP-1 Activity

In certain embodiments, the glucagon peptide, or analog thereof, comprises an amino acid modification which selectively reduces GLP-1 activity. For example, the acylated or alkylated glucagon peptide, or analog thereof, comprises a C-terminal alpha carboxylate group; a substitution of the Thr at position 7 with an amino acid lacking a hydroxyl group, e.g., Abu or Ile; deletion of the amino acid(s) C-terminal to the amino acid at position 27 or 28 (e.g., deletion of the amino acid at position 28, deletion of the amino acid at positions 28 and 29) to yield a peptide 27 or 28 amino acids in length, or a combination thereof.

Conjugates

The present disclosure also encompasses other conjugates in which glucagon peptides of the invention are linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The peptide can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly are reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W. H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Exemplary conjugate moieties that can be linked to any of the glucagon peptides described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide of the present invention and a plasma protein, wherein the plasma protein is selected from the group consisting of albumin, transferin, fibrinogen and globulins. In one embodiment the plasma protein moiety of the conjugate is albumin or transferin. In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in some embodiments, the glucagon peptides are conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005).

Amino acid residues involved in IgE receptor binding are described in Sayers et al. (J Biol Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591) Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

The present disclosure also encompasses glucagon fusion peptides or proteins wherein a second peptide or polypeptide has been fused to a terminus, e.g., the carboxy terminus of the glucagon peptide. Exemplary candidates for C-terminal fusion include SEQ ID NO: 820 (GPSSGAPPPS), SEQ ID NO: 821 (KRNRNNIA) or SEQ ID NO: 822 (KRNR) linked to amino acid 29 of the glucagon peptide.

Stabilization of the Alpha-Helix Structure

Reduction in glucagon activity upon modification of the amino acids at position 1 and/or position 2 of the glucagon peptide can be restored by stabilization of the alpha-helix structure in the C-terminal portion of the glucagon peptide (around amino acids 12-29). The alpha helix structure can be stabilized by, e.g., formation of a covalent or non-covalent intramolecular bridge, substitution and/or insertion of amino acids around positions 12-29 with an alpha helix-stabilizing amino acid (e.g., an α, α-disubstituted amino acid).

In some embodiments, an intramolecular bridge is formed between two amino acid side chains to stabilize the three dimensional structure of the carboxy terminal portion (e.g., amino acids 12-29) of the glucagon peptide. The two amino acid side chains can be linked to one another through non-covalent bonds, e.g., hydrogen-bonding, ionic interactions, such as the formation of salt bridges, or by covalent bonds. When the two amino acid side chains are linked to one another through one or more covalent bonds, the peptide may be considered herein as comprising a covlent intramolecular bridge. When the two amino acid side chains are linked to one another through non-covalent bonds, e.g., hydrogen bonds, ionic interactions, the peptide may be considered herein as comprising a non-covalent intramolecular bridge.

In some embodiments, the intramolecular bridge is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25). More particularly, the side chains of the amino acid pairs 12 and 16, 16 and 20, 20 and 24 or 24 and 28 (amino acid pairs in which i=12, 16, 20, or 24) are linked to one another and thus stabilize the glucagon alpha helix. Alternatively, i can be 17.

In some specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26). In some specific embodiments, j is 17.

In some specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22). In some specific embodiments, k is 12, 13, or 17. In an exemplary embodiment, k is 17.

Examples of amino acid pairings that are capable of covalently bonding to form a six-atom linking bridge include Orn and Asp, Glu and an amino acid of Formula I, wherein n is 2, and homoglutamic acid and an amino acid of Formula I, wherein n is 1, wherein Formula I is:

[Formula I]

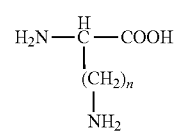

wherein n = 1 to 4

Examples of amino acid pairing that are capable of covalently bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect. Even without covalent linkage, the amino acid pairings described above or similar pairings that one of ordinary skill in the art can envision may also provide added stability to the alpha-helix through non-covalent bonds, for example, through formation of salt bridges or hydrogen-bonding interactions.

The size of a lactam ring can vary depending on the length of the amino acid side chains, and in one embodiment the lactam is formed by linking the side chains of a lysine amino acid to a glutamic acid side chain. Further exemplary embodiments include the following pairings, optionally with a lactam bridge: Glu at position 12 with Lys at position 16;

native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28. Alternatively, the order of the amide bond in the lactam ring can be reversed (e.g., a lactam ring can be formed between the side chains of a Lys12 and a Glu 16 or alternatively between a Glu 12 and a Lys16).

Intramolecular bridges other than a lactam bridge can be used to stabilize the alpha helix of the glucagon peptides. In one embodiment, the intramolecular bridge is a hydrophobic bridge. In this instance, the intramolecular bridge optionally is between the side chains of two amino acids that are part of the hydrophobic face of the alpha helix of the glucagon peptide. For example, one of the amino acids joined by the hydrophobic bridge can be the amino acid at position 10, 14, and 18.

In one specific aspect, olefin metathesis is used to cross-link one or two turns of the alpha helix of the glucagon peptide using an all-hydrocarbon cross-linking system. The glucagon peptide in this instance can comprise α-methylated amino acids bearing olefinic side chains of varying length and configured with either R or S stereochemistry at the i and i+4 or i+7 positions. For example, the olefinic side chain can comprise $(CH_2)n$, wherein n is any integer between 1 to 6. In one embodiment, n is 3 for a cross-link length of 8 atoms. Suitable methods of forming such intramolecular bridges are described in the art. See, for example, Schafmeister et al., *J. Am. Chem. Soc.* 122: 5891-5892 (2000) and Walensky et al., *Science* 305: 1466-1470 (2004). Alternatively, the glucagon peptide can comprise O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In another specific aspect, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α, ω-diaminoalkane tethers, e.g., 1,4-diaminopropane and 1,5-diaminopentane) between two Glu residues at positions i and i+7 are used to stabilize the alpha helix of the glucagon peptide. Such tethers lead to the formation of a bridge 9-atoms or more in length, depending on the length of the diaminoalkane tether. Suitable methods of producing peptides cross-linked with such tethers are described in the art. See, for example, Phelan et al., *J. Am. Chem. Soc.* 119: 455-460 (1997).

In yet another embodiment of the invention, a disulfide bridge is used to cross-link one or two turns of the alpha helix of the glucagon peptide. Alternatively, a modified disulfide bridge in which one or both sulfur atoms are replaced by a methylene group resulting in an isosteric macrocyclization is used to stabilize the alpha helix of the glucagon peptide. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet another embodiment, the alpha helix of the glucagon peptide is stabilized via the binding of metal atom by two His residues or a His and Cys pair positioned at i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the glucagon peptide can alternatively be stabilized through other means of peptide cyclizing, which means are reviewed in Davies, *J. Peptide. Sci.* 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g. suberic acid (octanedioic acid), etc. can introduce a link between two functional groups of an amino acid side chain, such as a free amino, hydroxyl, thiol group, and combinations thereof.

In accordance with one embodiment, the alpha helix of the glucagon peptide is stabilized through the incorporation of hydrophobic amino acids at positions i and i+4. For instance, i can be Tyr and i+4 can be either Val or Leu; i can be Phe and i+4 can be Cys or Met; I can be Cys and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position.

In accordance with other embodiments of the invention, the alpha helix is stabilized through incorporation (either by amino acid substitution or insertion) of one or more alpha helix-stabilizing amino acids at the C-terminal portion of the glucagon peptide (around amino acids 12-29). In a specific embodiment, the alpha helix-stabilizing amino acid is an α, α-disubstitued amino acid, including, but not limited to any of amino iso-butyric acid (Aib), an amino acid disubstituted with the same or a different group selected from methyl, ethyl, propyl, and n-butyl, or with a cyclooctane or cycloheptane (e.g., 1-aminocyclooctane-1-carboxylic acid). In some embodiments, one, two, three, four or more of positions 16, 17, 18, 19, 20, 21, 24 or 29 of the glucagon peptide is substituted with an α, α-disubstituted amino acid. In a specific embodiment, one, two, three or all of positions 16, 20, 21, and 24 are substituted with Aib. For example, the glucagon peptide can comprise a substitution of position 16 with Aib in the absence of an intramolecular bridge, e.g., a non-covalent intramolecular bridge (e.g., a salt bridge) or a covalent intramolecular bridge (e.g., a lactam). Such peptides lacking an intramolecular bridge are advantageously easy to prepare.

In accordance with some embodiments, the glucagon peptide lacking an intramolecular bridge comprises one or more substitutions within amino acid positions 12-29 with an α, α-disubstituted amino acid and an acyl or alkyl group covalently attached to the side chain of an amino acid of the glucagon peptide, e.g., the amino acid at position 10 of the glucagon peptide. In specific embodiments, the acyl or alkyl group is non-native to a naturally occurring amino acid. In certain aspects, the acyl or alkyl group is non-native to the amino acid at position 10. Such acylated or alkylated glucagon peptides lacking an intramolecular bridge exhibit enhanced activity at the GLP-1 and glucagon receptors as compared to the non-acylated counterpart peptides. Further enhancement in activity at the GLP-1 and glucagon receptors can be achieved by the acylated glucagon peptides lacking an intramolecular bridge by incorporating a spacer between the acyl or alkyl group and the side chain of the amino acid at position 10 of the peptide. Acylation and alkylation, with or without incorporating spacers, are further described herein.

In specific embodiments, the acylated or alkylated glucagon peptide, or analog thereof, further comprises a modification which selectively reduces activity at the GLP-1 receptor. For example, the acylated or alkylated glucagon peptide, or analog thereof, comprises one or a combination of: a C-terminal alpha carboxylate, a deletion of the amino acids C-terminal to the amino acid at position 27 or 28 (e.g., deletion of the amino acid at position 29, deletion of the amino acids at positions 28 and 29), a substitution of the Thr at position 7 with an amino acid lacking a hydroxyl group, e.g., Abu or Ile.

Examples of Embodiments

In accordance with one embodiment the native glucagon peptide of SEQ ID NO: 1 is modified by the substitution of the native amino acid at position 6, 10 or 13 with pyridyl-alanine, and optionally substitution at position 28 and/or 29 with a negatively charged amino acid (e.g., aspartic acid or glutamic acid) and further optionally the addition of a negatively charged amino acid (e.g., aspartic acid or glutamic acid) to the carboxy terminus of the peptide. Optionally, in one embodiment the pyridyl-alanine substituted analogs of the present disclosure are further modified by the substitution of the native amino acid at position 29 with a positively charged amino acid (e.g., lysine, arginine or histidine) and optionally the addition of one or two positively charged amino acid (e.g., lysine, arginine or histidine) on the carboxy terminus of the peptide. In accordance with one embodiment a glucagon peptide having improved solubility and stability is provided wherein the analog comprises the amino acid sequence of SEQ ID NO: 966 with the proviso that at least one amino acids at position 6, 10 or 13 is substituted with pyridyl-alanine. In a further embodiment, 28, or 29 is substituted with an acidic amino acid and/or an additional acidic amino acid is added at the carboxy terminus of SEQ ID NO: 966. In one embodiment the acidic amino acids are independently selected from the group consisting of Asp, Glu, cysteic acid and homocysteic acid.

In accordance with one embodiment a glucagon peptide having improved solubility and stability is provided wherein the agonist comprises the amino acid sequence of SEQ ID NO: 964, wherein at least one amino acids at position 6, 10 or 13 is substituted with pyridyl-alanine, and optionally at least one of the amino acids at positions 27, 28 or 29 is substituted with a non-native amino acid residue (i.e. at least one amino acid present at position 27, 28 or 29 of the analog is an acid amino acid different from the amino acid present at the corresponding position in SEQ ID NO: 1). In accordance with one embodiment a glucagon peptide is provided comprising the sequence of SEQ ID NO: 964 with at least one amino acids at position 6, 10 or 13 substituted with pyridyl-alanine and the amino acid at position 28 is asparagine, optionally with the peptide further comprises one to two amino acids, independently selected from the group consisting of Lys, Arg, His, Asp or Glu, added to the carboxy terminus of the glucagon peptide.

In one embodiment a glucagon peptide of SEQ ID NO: 964 is provided wherein at least one amino acid at position 6, 10 or 13 is substituted with pyridyl-alanine and 1 to 6 amino acids, selected from positions 5, 7, 11, 12, 14, 17, 18, 19, 21 or 24 of the analog differ from the corresponding amino acid of SEQ ID NO: 1. In accordance with another embodiment a glucagon peptide of SEQ ID NO: 964 is provided wherein at least one amino acid at position 6, 10 or 13 is substituted with pyridyl-alanine and 1 to 3 amino acids selected from positions 5, 7, 11, 12, 14, 17, 18, 19, 21 or 24 of the analog differ from the corresponding amino acid of SEQ ID NO: 1. In another embodiment, a glucagon peptide of SEQ ID NO: 966 is provided wherein at least one amino acid at position 6, 10 or 13 is substituted with pyridyl-alanine and 1 to 2 amino acids selected from positions 1, 2, 5, 7, 11, 12, 14, 16, 17, 18, 19, 20, 21 or 24 of the analog differ from the corresponding amino acid of SEQ ID NO: 1, and in a further embodiment those one to two differing amino acids represent conservative amino acid substitutions relative to the amino acid present in the native sequence (SEQ ID NO: 1). In one embodiment a glucagon peptide derivative of SEQ ID NO: 11 or SEQ ID NO: 13 is provided wherein the peptide differs from SEQ ID NO: 11 or SEQ ID NO: 13 by having at least one amino acids at position 6, 10 or 13 is substituted with pyridyl-alanine and optionally the glucagon peptide further comprises one, two or three amino acid substitutions at positions selected from positions 2, 5, 7, 11, 12, 14, 16, 17, 18, 19, 20, 21, 24, 27 or 29. In one embodiment the substitutions at positions 2, 5, 7, 11, 12, 14, 16, 17, 18, 19, 20, 27 or 29 are conservative amino acid substitutions.

In one embodiment a glucagon peptide is provided comprising an analog of SEQ ID NO: 1 wherein the analog differs from SEQ ID NO: 1 by having an amino acid other than serine at position 2, at least one amino acids at position 6, 10 or 13 substituted with pyridyl-alanine, and optionally an acidic amino acid substituted for the native amino acid at position 28 or 29 or an acidic amino acid added to the carboxy terminus of the peptide of SEQ ID NO: 1. In one embodiment the acidic amino acid is aspartic acid or glutamic acid.

In accordance with one embodiment the glucagon peptide comprises a sequence that differs from a sequence selected from the group consisting of SEQ ID NO: 9, SEQ ID NO: 12, SEQ ID NO: 13 and SEQ ID NO: 32 by at least one amino acid at position 6, 10 or 13 being substituted with a pyridyl-alanine. In a further embodiment a glucagon peptide is provided comprising a sequence that differs from SEQ ID NO: 9, SEQ ID NO: 12, SEQ ID NO: 13 or SEQ ID NO: 32 by having at least one amino acid at position 6, 10 or 13 substituted with pyridyl-alanine and further comprising one to two amino acids, added to the C-terminus of SEQ ID NO: 9, SEQ ID NO: 12, SEQ ID NO: 13 or SEQ ID NO: 32, wherein the additional amino acids are independently selected from the group consisting of Lys, Arg, His, Asp Glu, cysteic acid or homocysteic acid. In one embodiment the additional amino acids added to the carboxy terminus are selected from the group consisting of Lys, Arg, His, Asp or Glu or in a further embodiment the additional amino acids are Asp or Glu.

The present disclosure also encompasses glucagon peptides wherein a second peptide has been fused to the C-terminus of the glucagon peptide to enhance the stability and solubility of the glucagon peptide. More particularly, the fusion glucagon peptide may comprise a derivative of the sequence NH$_2$-His-Ser-Gln-Gly-Thr-Phe-Thr-Ser-Asp-Tyr-Ser-Lys-Tyr-Leu-Asp-X$_{16}$-Arg-Arg-Ala-Gln-Asp-Phe-Val-Gln-Trp-Leu-X$_{27}$-X$_{28}$-X$_{29}$-R (SEQ ID NO: 942), wherein X$_{16}$ is Thr or Aib, X$_{27}$ is Met, Leu or Nle, X$_{28}$ is Lys, Arg, His, Asp, Glu, cysteic acid or homocysteic acid, and X$_{29}$ is Thr, Lys, Arg, His, Asp, Glu, cysteic acid or homocysteic acid, and the peptide differs form SEQ ID NO: 942 by having at least one amino acid at position 6, 10 or 13 is substituted with pyridyl-alanine and wherein R is an acidic amino acid, a bond or an amino acid sequence of SEQ ID NO: 820 (GPSSGAPPPS), SEQ ID NO: 821 (KRNRNNIA) or SEQ ID NO: 822 (KRNR) linked to the carboxy terminal amino acid of the glucagon peptide. In one embodiment the glucagon peptide is a derivative of a peptide selected from the group consisting of SEQ ID NO: 33, SEQ ID NO: 7 or SEQ ID NO: 8 wherein the derivative further comprises at least one amino acid at position 6, 10 or 13 substituted with pyridyl-alanine and an amino acid sequence of SEQ ID NO: 820 (GPSSGAPPPS), SEQ ID NO: 821 (KRNRNNIA) or SEQ ID NO: 822 (KRNR) linked to the carboxy terminal amino acid of the glucagon peptide. In one embodiment the glucagon peptide comprises SEQ ID NO: 2, SEQ ID NO: 3, SEQ ID NO: 4, SEQ ID NO: 5 and SEQ ID NO: 6 modified by at least one amino acids at position 6, 10 or 13 being substituted with pyridyl-alanine, or an analog thereof, further comprising an amino acid sequence of SEQ ID NO: 820 (GPSSGAPPPS), SEQ ID NO: 821 (KRNRNNIA) or SEQ ID NO: 822 (KRNR) linked to amino acid 29 of the glucagon peptide. In accordance with one embodiment the fusion peptide further comprises a PEG chain linked to an amino acid at position 16, 17, 21, 24, 29, within a C-terminal extension, or at the C-terminal amino acid, wherein the PEG chain is selected from the range of 500 to 40,000 Daltons. In one embodiment the amino acid sequence of SEQ ID NO: 820 (GPSSGAPPPS), SEQ ID NO: 821 (KRNRNNIA) or SEQ ID NO: 822 (KRNR) is bound to amino acid 29 of the glucagon peptide through a peptide bond.

Typically the fusion peptides of the present invention will have a C-terminal amino acid with the standard carboxylic acid group. However, analogs of those sequences wherein the C-terminal amino acid has an amide substituted for the carboxylic acid are also encompassed as embodiments. In accordance with one embodiment the fusion glucagon peptide comprises a sequence selected from the group consisting of SEQ ID NO: 10, SEQ ID NO: 11 and SEQ ID NO: 13, modified by at least one amino acid at position 6, 10 or 13 being substituted with pyridyl-alanine and further comprising an amino acid sequence of SEQ ID NO: 823 (GPSS-GAPPPS-CONH2) linked to amino acid 29 of the glucagon peptide.

In accordance with one embodiment the pegylated glucagon peptide comprises two or more polyethylene chains covalently bound to the glucagon peptide wherein the total molecular weight of the glucagon chains is about 1,000 to about 5,000 Daltons. In one embodiment the pegylated glucagon agonist comprises a peptide of SEQ ID NO: 6, modified by having at least one amino acid at position 6, 10 or 13 substituted with pyridyl-alanine wherein a PEG chain is covalently linked to the amino acid residue at position 21 and at position 24, and wherein the combined molecular weight of the two PEG chains is about 1,000 to about 5,000 Daltons or about 5,000 to about 20,000 Daltons.

The polyethylene glycol chain may be in the form of a straight chain or it may be branched. In accordance with one embodiment the polyethylene glycol chain has an average molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 20,000 to about 40,000 Daltons.

Any of the glucagon peptides described above may be further modified to include a covalent or non-covalent intramolecular bridge or an alpha helix-stabilizing amino acid within the C-terminal portion of the glucagon peptide (amino acid positions 12-29). In accordance with one embodiment, the glucagon peptide comprises any one or more of the modifications discussed above in addition to an amino acid substitution at positions 16, 20, 21, or 24 (or a combination thereof) with an α,α-disubstituted amino acid, e.g., Aib. In accordance with another embodiment, the glucagon peptide comprises any one or more modifications discussed above in addition to an intramolecular bridge, e.g., a lactam, between the side chains of the amino acids at positions 16 and 20 of the glucagon peptide.

In accordance with some embodiments, the glucagon peptide comprises an amino acid at position 3 comprising a side chain of Structure I, II, or III:

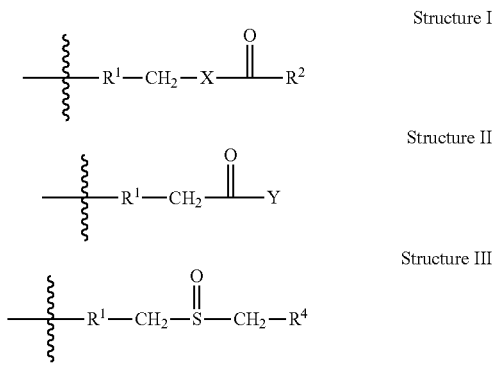

wherein R$^1$ is C$_{0-3}$ alkyl or C$_{0-3}$ heteroalkyl; R$^2$ is NHR$^4$ or C$_{1-3}$ alkyl; R$^3$ is C$_{1-3}$ alkyl; R$^4$ is H or C$_{1-3}$ alkyl; X is NH, O, or S; and Y is NHR$^4$, SR$^3$, or OR$^3$. In some embodiments, X is NH or Y is NHR$^4$. In some embodiments, R$^1$ is C$_{0-2}$ alkyl or C$_1$ heteroalkyl. In some embodiments, R$^2$ is NHR$^4$ or C$_1$ alkyl. In some embodiments, R$^4$ is H or C$^1$ alkyl. In exemplary embodiments, an amino acid comprising a side chain of Structure I is provided where, R$^1$ is CH$_2$—S, X is NH, and R$^2$ is CH$_3$ (acetamidomethyl-cysteine, C(Acm)); R$^1$ is CH$_2$, X is NH, and R$^2$ is CH$_3$ (acetyldiaminobutanoic acid, Dab(Ac)); R$^1$ is C$_0$ alkyl, X is NH, R$^2$ is NHR$^4$, and R$^4$ is H (carbamoyldiaminopropanoic acid, Dap(urea)); or R$^1$ is CH$_2$—CH$_2$, X is NH, and R$^2$ is CH$_3$ (acetylornithine, Orn (Ac)). In exemplary embodiments, an amino acid comprising a side chain of Structure II is provided where, R$^1$ is CH$_2$, Y is NHR$^4$, and R$^4$ is CH$_3$ (methylglutamine, Q(Me)); In exemplary embodiments, an amino acid comprising a side chain of Structure III is provided where, R$^1$ is CH$_2$ and R$^4$ is H (methionine-sulfoxide, M(O)); In specific embodiments, the amino acid at position 3 is substituted with Dab(Ac).

In specific aspects, the analog comprises any of the amino acid modifications described herein, including, but not limited to: a substitution of Asn at position 28 with a charged amino acid; a substitution of Asn at position 28 with a charged amino acid selected from the group consisting of Lys, Arg, His, Asp, Glu, cysteic acid, and homocysteic acid; a substitution at position 28 with Asn, Asp, or Glu; a substitution at position 28 with Asp; a substitution at position 28 with Glu; a substitution of Thr at position 29 with a charged amino acid; a substitution of Thr at position 29 with a charged amino acid selected from the group consisting of Lys, Arg, His, Asp, Glu, cysteic acid, and homocysteic acid; a substitution at position 29 with Asp, Glu, or Lys; a substitution at position 29 with Glu; a insertion of 1-3 charged amino acids after position 29; an insertion after position 29 of Glu or Lys; an insertion after position 29 of Gly-Lys or Lys-Lys; and a combination thereof; an α, α-disubstituted amino acid, such as Aib, at one, two, three, or all of positions 16, 20, 21, and 24.

In certain embodiments, the analog of the glucagon peptide of SEQ ID NO: 1 comprises one or more of the following: at least one amino acid at position 6, 10 or 13 substituted with pyridyl-alanine; substitution of His at position 1 with a non-native amino acid that reduces susceptibility of the glucagon peptide to cleavage by dipeptidyl peptidase IV (DPP-IV), substitution of Ser at position 2 with a non-native amino acid that reduces susceptibility of the glucagon peptide to cleavage by dipeptidyl peptidase IV (DPP-IV), substitution of Thr at position 7 with an amino acid lacking a hydroxyl group, e.g., Abu or Ile; substitution of Tyr at position 10 with Phe or Val; substitution of Lys at position 12 with Arg; substitution of Asp at position 15 with Glu, substitution of Ser at position 16 with Thr or Aib; substitution of Gln at position 20 with Ala or Aib; substitution of Asp at position 21 with Glu; substitution of Gln at position 24 with Ala or Aib; substitution of Met at position 27 with Leu or Nle; deletion of amino acids at positions 27-29; deletion of amino acids at positions 28-29; deletion of the amino acid at positions 29; addition of the amino acid sequence of SEQ ID NO: 820 to the C-terminus, wherein the amino acid at position 29 is Thr or Gly, or a combination thereof.

In certain embodiments, the analog of the glucagon peptide comprising SEQ ID NO: 1 comprises at least one amino acid at position 6, 10 or 13 substituted with pyridyl-alanine; an amino acid comprising a side chain covalently attached, optionally, through a spacer, to an acyl group or an alkyl group, which acyl group or alkyl group is non-native to a naturally-occurring amino acid. The acyl group in some embodiments is a C4 to C30 fatty acyl group. In other embodiments, the alkyl group is a C4 to C30 alkyl. In specific aspects, the acyl group or alkyl group is covalently attached to the side chain of the amino acid at position 10. In some embodiments, the amino acid at position 7 is Ile or Abu.

Use

The glucagon peptides disclosed herein have enhanced biophysical stability and aqueous solubility in solutions of physiological pH, while retaining or demonstrating enhanced bioactivity relative to the native peptide. Accordingly, the glucagon peptides of the present invention are believed to be suitable for any use that has previously been described for the native glucagon peptide. Therefore, the modified glucagon peptides described herein can be used to treat hypoglycemia, to increase blood glucose level, to induce temporary paralysis of the gut for radiological uses, to reduce and maintain body weight, as adjunctive therapy with insulin, or to treat other metabolic diseases that result from low blood levels of glucagon.

The glucagon peptides described herein also are expected to be used to reduce or maintain body weight, or to treat hyperglycemia, or to reduce blood glucose level, or to normalize blood glucose level, and/or to stabilize blood glucose level. "Normalizing" blood level means that the blood glucose level is returned to normal (e.g., lowering blood glucose level if it is higher than normal, or raising blood glucose level if it is lower than normal). "Stabilizing" blood glucose level means reducing the maximal variation in blood glucose level over a period of time, e.g., 8 hours, 16 hours, 24 hours, 2 days, 3 days, 4 days, 5 days, 6 days or 1 week. For example, administration of glucagon peptide causes the blood glucose level over time to be maintained closer to the normal range of glucose values than it would be in the absence of administration of glucagon peptide.

The glucagon peptides of the invention may be administered alone or in combination with other anti-diabetic or anti-obesity agents. Anti-diabetic agents known in the art or under investigation include insulin, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to xenical (Orlistat) or Cetilistat (also known as ATL-962), or GT 389-255.

One aspect of the present disclosure is directed to a pre-formulated aqueous solution of the presently disclosed glucagon peptides for use in treating hypoglycemia. The improved stability and/or solubility of the glucagon peptide compositions described herein allow for the preparation of pre-formulated aqueous solutions of glucagon for rapid administration and treatment of hypoglycemia. Accordingly, in one embodiment a solution comprising a glucagon peptide of the present invention is provided for administration to a patient suffering from hypoglycemia. In one embodiment a solution comprising a pegylated glucagon peptide as disclosed herein is provided for administration to a patient suffering from hypoglycemia, wherein the total molecular weight of the PEG chains linked to the pegylated glucagon peptide is between about 500 to about 5,000 Daltons. The treatment methods in accordance with the present invention, including but not limited to treatment of hypoglycemia, may comprise the steps of administering the presently disclosed glucagon peptides to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the glucagon composition is prepackaged in a syringe.

In another embodiment, the composition is prepackaged in an inhaler or other aerosolized drug deliver device. Advantageously, the aqueous stable glucagon peptides disclosed herein exhibit superior stability and solubility in aqueous buffers in the broadest pH range used for pharmacological purposes, relative to native glucagon. The use of the stabilized glucagon peptides disclosed herein allows for the preparation and storage of glucagon solutions at physiological pH for long periods of time.

Glucagon peptides that have been modified to be covalently bound to a PEG chain having a molecular weight of greater than 10,000 Daltons can be administered in conjunction with insulin to buffer the actions of insulin and help to maintain stable blood glucose levels in diabetics. The modified glucagon peptides of the present disclosure can be co-administered with insulin as a single composition, simultaneously administered as separate solutions, or alternatively, the insulin and the modified glucagon peptide can be administered at different time relative to one another. In one embodiment the composition comprising insulin and the composition comprising the modified glucagon peptide are administered within 12 hours of one another. The exact ratio of the modified glucagon peptide relative to the administered insulin will be dependent in part on determining the glucagon levels of the patient, and can be determined through routine experimentation.

In accordance with one embodiment a composition is provided comprising insulin and a modified glucagon peptide selected from the group consisting of SEQ ID NO: 2, SEQ ID NO: 3, SEQ ID NO: 4, SEQ ID NO: 5 and glucagon agonist analogs thereof, wherein the modified glucagon peptide further comprises at least one amino acid at position 6, 10 or 13 substituted with pyridyl-alanine, and optionally a polyethylene glycol chain covalently bound to an amino acid side chain at position 16, 17, 21, 24, 29, within a C-terminal extension, or at the C-terminal amino acid. In one embodiment the composition is an aqueous solution comprising insulin and the glucagon peptide. In embodiments wherein the glucagon peptide comprises the sequence of SEQ ID NO: 11 or SEQ ID NO: 13, the peptide may further comprise a polyethylene glycol chain covalently bound to an amino acid side chain at position 16, 17, 21, 24, 29, within a C-terminal extension, or at the C-terminal amino acid. In one embodiment the molecular weight of the PEG chain of the modified glucagon peptide is greater than 10,000 Daltons.

In accordance with one embodiment the modified glucagon peptides disclosed herein are used to induce temporary paralysis of the intestinal tract. This method has utility for radiological purposes and comprises the step of administering an effective amount of a pharmaceutical composition comprising a pegylated glucagon peptide, a glucagon peptide comprising a c-terminal extension or a dimer of such peptides. In one embodiment the glucagon peptide comprises a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 wherein the peptide is modified to comprise at least one amino acid at position 6, 10 or 13 substituted with pyridyl-alanine. In one embodiment the glucagon peptide further comprises a PEG chain, of about 1,000 to 40,000 Daltons is covalently bound to an amino acid residue at position 21, 24 or 29, within a C-terminal extension, or at the C-terminal amino acid.

In a further embodiment the composition used to induce temporary paralysis of the intestinal tract comprises a first modified glucagon peptide and a second modified glucagon peptide, wherein the first modified peptide comprises a sequence selected from the group consisting of SEQ ID NO: 10, SEQ ID NO: 11 and SEQ ID NO: 13, optionally linked to a PEG chain of about 500 to about 5,000 Daltons, and the second peptide comprises a covalently linked PEG chain of about 10,000 to about 40,000 Daltons. In this embodiment the PEG chain of each peptide is covalently bound to an amino acid residue at either position 21, 24 or 29, within a C-terminal extension, or at the C-terminal amino acid, of the respective peptide, and independent of one another.

Oxyntomodulin, a naturally occurring digestive hormone found in the small intestine, has been reported to cause weight loss when administered to rats or humans (see Diabetes 2005; 54:2390-2395). Oxyntomodulin is a 37 amino acid peptide that contains the 29 amino acid sequence of glucagon (i.e. SEQ ID NO: 1) followed by an 8 amino acid carboxy terminal extension of SEQ ID NO: 821 (KRNRNNIA). Accordingly, applicants believe that the bioactivity of oxyntomodulin can be retained (i.e. appetite suppression and induced weight loss/weight maintenance), while improving the solubility and stability of the compound and improving the pharmacokinetics, by substituting the glucagon peptide portion of oxyntomodulin with the modified glucagon peptides disclosed herein. In addition applicants also believe that a truncated oxyntomodulin molecule comprising a glucagon peptide of the invention, having the terminal four amino acids of oxyntomodulin removed, will also be effective in suppressing appetite and inducing weight loss/weight maintenance.

Accordingly, the present invention also encompasses the modified glucagon peptides of the present invention that have a carboxy terminal extension of SEQ ID NO: 821 (KRNRNNIA) or SEQ ID NO: 822. In accordance with one embodiment a glucagon peptide of SEQ ID NO: 33, modified to have at least one amino acid at position 6, 10 or 13 substituted with pyridyl-alanine and further comprising the amino acid sequence of SEQ ID NO: 821 (KRNRNNIA) or SEQ ID NO: 822 linked to amino acid 29 of the glucagon peptide, is administered to individuals to induce weight loss or prevent weight gain. In accordance with one embodiment a glucagon peptide of SEQ ID NO: 11 or SEQ ID NO: 13, modified to have at least one amino acid at position 6, 10 or 13 substituted with pyridyl-alanine and further comprising the amino acid sequence of SEQ ID NO: 821 (KRNRNNIA) or SEQ ID NO: 822 linked to amino acid 29 of the glucagon peptide, is administered to individuals to induce weight loss or prevent weight gain. In another embodiment a method of reducing weight gain or inducing weight loss in an individual comprises administering an effective amount of a composition comprising a glucagon peptide selected from the group consisting of SEQ ID NO: 2, SEQ ID NO: 3, SEQ ID NO: 4 or SEQ ID NO: 5, wherein at least one amino acid at position 6, 10 or 13 is substituted with pyridyl-alanine and amino acid 29 of the glucagon peptide is bound to a second peptide through a peptide bond, and said second peptide comprises the sequence of SEQ ID NO: 824 (KRNRNNIA) or SEQ ID NO: 825, and wherein a PEG chain of about 1,000 to 40,000 Daltons is covalently bound to an amino acid residue at position 21 and/or 24.

Exendin-4 is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivy of glucagon. In one embodiment the terminal ten amino acids of Exendin-4 (i.e. the sequence of SEQ ID NO: 820 (GPSSGAPPPS)) are linked to the carboxy terminus of a glucagon peptide of the present disclosure. In specific aspects, the sequence of SEQ ID NO: 820, modified to comprise at least one amino acid at position 6, 10 or 13 being substituted with pyridyl-alanine, is linked to the C-terminus of the glucagon peptide and the amino acid at position 29 is either Thr or Gly. These fusion proteins are anticipated to have pharmacological activity for suppressing appetite and inducing weight loss/weight maintenance. In one embodiment the terminal amino acid of the SEQ ID NO: 820 extension comprises an amide group in place of the carboxy group (i.e., SEQ ID NO: 823) and this sequence is linked to the carboxy terminus of a glucagon peptide of the present disclosure.

In one embodiment a method of reducing weight gain or inducing weight loss in an individual comprises administering an effective amount of a composition comprising a glucagon peptide of SEQ ID NO: 33 wherein at least one amino acid at position 6, 10 or 13 is substituted with pyridyl-alanine and amino acid 29 of the glucagon peptide is bound to a second peptide through a peptide bond, and said second peptide comprises the sequence of SEQ ID NO: 820 (GPSSGAPPPS) or SEQ ID NO: 823. In one embodiment the glucagon peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 wherein at least one amino acid at position 6, 10 or 13 is substituted with pyridyl-alanine and optionally amino acid 29 of the glucagon peptide is bound to a second peptide through a peptide bond, wherein said second peptide comprises the sequence of SEQ ID NO: 820 (GPSSGAPPPS) or SEQ ID NO: 823.

In another embodiment a composition is administered to a patient to suppress appetite, prevent weight gain and/or induce weight loss by the administration of a pharmaceutical composition comprising a first pegylated glucagon peptide and a second pegylated glucagon peptide, wherein the first and second peptide are fusion peptides comprising a c-terminal peptide extension comprising SEQ ID NO: 820 (GPSSGAPPPS) or SEQ ID NO: 823. The first pegylated glycogen peptide comprising a covalently linked PEG of about 500 to about 10,000 Daltons and the second pegylated glucagon peptide comprising a covalently linked PEG chain of about 10,000 to about 40,000 Daltons.

The present disclosure also encompasses multimers of the modified glucagon peptides disclosed herein. Two or more of the modified glucagon peptides can be linked together using standard linking agents and procedures known to those skilled in the art. For example, dimers can be formed between two modified glucagon peptides through the use of bifunctional thiol crosslinkers and bi-functional amine crosslinkers, particularly for the glucagon peptides that have been substituted with cysteine, lysine ornithine, homocysteine or acetyl phenylalanine residues (e.g. SEQ ID NO: 4 and SEQ ID NO: 5). The dimer can be a homodimer or alternatively can be a heterodimer. In one embodiment the dimer comprises a homodimer of a glucagon peptide wherein the glucagon peptide portion comprises an agonist analog of SEQ ID NO: 11 and an amino acid sequence of SEQ ID NO: 820 (GPSSGAPPPS), SEQ ID NO: 821 (KRNRNNIA) or SEQ ID NO: 822 (KRNR) linked to amino acid 29 of the glucagon peptide. In another embodiment the dimer comprises a homodimer of a glucagon peptide of SEQ ID NO: 11, wherein the glucagon peptide further comprises a polyethylene glycol chain covalently bound to position 21, 24, 29, within a C-terminal extension, or at the C-terminal amino acid of the glucagon peptide.

In accordance with one embodiment a pharmaceutical composition is provided wherein the composition comprises a glucagon peptide of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

The pharmaceutical formulations disclosed herein may be designed to be short-acting, fast-releasing, long-acting, or sustained-releasing as described below. The pharmaceutical formulations may also be formulated for immediate release, controlled release or for slow release. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise one or more buffering agents to achieve a physiological compatible pH. The buffering agents may include any compounds capable of buffering at the desired pH such as, for example, phosphate buffers (e.g. PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g. at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

In one embodiment the pharmaceutical composition comprises a 1 mg/ml concentration of the glucagon peptide and 10-50 mM Triethanolamine at pH 7.0-8.5, or 6-9, or 7-9. In one embodiment the pharmaceutical composition comprises a 1 mg/ml concentration of the glucagon peptide and 20 mM Triethanolamine at pH 8.5.

The modified glucagon peptides of the present invention can be provided in accordance with one embodiment as part of a kit. In one embodiment a kit for administering a glucagon peptide to a patient in need thereof is provided wherein the kit comprises any of the glucagon peptides of the invention in aqueous solution. In one embodiment the kit is provided with a device for administering the glucagon composition to a patient, e.g. syringe needle, pen device, jet injector or other needle-free injector. The kit may alternatively or in addition include one or more of a variety of containers, e.g., vials, tubes, bottles, single or multi-chambered pre-filled syringes, cartridges, infusion pumps (external or implantable), jet injectors, pre-filled pen devices and the like, optionally containing the glucagon peptide in a lyophilized form or in aqueous solution. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the sterile glucagon composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXEMPLIFIED EMBODIMENTS

Embodiment 1

An enhanced soluble glucagon peptide, said peptide comprising an amino acid sequence of HSQGT FTSDY SKYLD SRRAQ DFVQW LMNT (SEQ ID NO: 1), wherein 1, 2, or 3 of positions 6, 10 or 13 have been substituted with pyridyl-alanine or histidine, optionally comprising up to 10 further amino acid modifications.

Embodiment 2

The peptide according to embodiment 1, wherein 1, 2, or 3 of positions 6, 10 or 13 have been substituted with pyridyl-alanine.

Embodiment 3

The peptide according to any one of embodiments 1-2, wherein 2 or 3 of positions 6, 10 or 13 have been substituted with pyridyl-alanine.

Embodiment 4

The peptide according to any one of the preceding embodiments, wherein positions 6, 10 and 13 have been substituted with pyridyl-alanine.

Embodiment 5

The peptide according to any one of the preceding embodiments wherein the peptide comprises up to 9 further amino acid modifications.

Embodiment 6

The peptide according to any one of the preceding embodiments wherein the peptide comprises up to 8 further amino acid modifications.

Embodiment 7

The peptide according to any one of the preceding embodiments wherein the peptide comprises up to 7 further amino acid modifications.

Embodiment 8

The peptide according to any one of the preceding embodiments wherein the peptide comprises up to 6 further amino acid modifications.

Embodiment 9

The peptide according to any one of the preceding embodiments wherein the peptide comprises up to 5 further amino acid modifications.

Embodiment 10

The peptide according to any one of the preceding embodiments wherein the peptide comprises up to 4 further amino acid modifications.

Embodiment 11

The peptide according to any one of the preceding embodiments wherein the peptide comprises up to 3 further amino acid modifications.

Embodiment 12

The peptide according to any one of the preceding embodiments wherein the peptide comprises up to 2 further amino acid modifications.

Embodiment 13

The peptide according to any one of the preceding embodiments wherein the peptide comprises up to 1 further amino acid modification.

Embodiment 14

The peptide according to any one of the preceding embodiments wherein the peptide comprises d-Gln at position 20.

Embodiment 15

The peptide according to any one of the preceding embodiments wherein the peptide comprises d-Asp at position 21.

Embodiment 16

The peptide according to any one of embodiments 1-12, 14-15 wherein the peptide comprises Asp at position 28 and Glu at position 29.

Embodiment 17

The peptide according to any one of the preceding embodiments wherein the peptide comprises pyridyl-alanine or histidine at position 6.

Embodiment 18

The peptide according to any one of the preceding embodiments wherein the peptide comprises pyridyl-alanine or histidine at position 10.

Embodiment 19

The peptide according to any one of the preceding embodiments wherein the peptide comprises pyridyl-alanine or histidine at position 13.

Embodiment 20

The peptide according to any one of the preceding embodiments wherein the peptide comprises pyridyl-alanine or histidine at positions 6 and 10.

Embodiment 21

The peptide according to any one of the preceding embodiments wherein the peptide comprises pyridyl-alanine or histidine at positions 6 and 13.

Embodiment 22

The peptide according to any one of the preceding embodiments wherein the peptide comprises pyridyl-alanine or histidine at positions 10 and 13.

Embodiment 23

The peptide according to any one of the preceding embodiments wherein the peptide comprises pyridyl-alanine or histidine at positions 6, 10, and 13.

Embodiment 24

The peptide according to any one of the preceding embodiments wherein the peptide comprises pyridyl-alanine at position 6.

Embodiment 25

The peptide according to any one of the preceding embodiments wherein the peptide comprises pyridyl-alanine at position 10.

Embodiment 26

The peptide according to any one of the preceding embodiments wherein the peptide comprises pyridyl-alanine at position 13.

Embodiment 27

The peptide according to any one of the preceding embodiments wherein the peptide comprises pyridyl-alanine at positions 6 and 10.

Embodiment 28

The peptide according to any one of the preceding embodiments wherein the peptide comprises pyridyl-alanine at positions 6 and 13.

Embodiment 29

The peptide according to any one of the preceding embodiments wherein the peptide comprises pyridyl-alanine at positions 10 and 13.

Embodiment 30

The peptide according to any one of the preceding embodiments wherein the peptide comprises pyridyl-alanine at positions 6, 10, and 13.

Embodiment 31

The peptide according to any one of the preceding embodiments wherein the pyridyl-alanine is selected from the group consisting of 3-(3-Pyridyl)-L-alanine and 3-(4-Pyridyl)-L-alanine).

Embodiment 32

The peptide according to any one of the preceding embodiments wherein the pyridyl-alanine is 3-(3-Pyridyl)-L-alanine.

Embodiment 33

The peptide according to any one of embodiments 1-31 wherein the pyridyl-alanine is 3-(4-Pyridyl)-L-alanine).

Embodiment 34

The peptide according to any one of the preceding embodiments wherein the peptide comprises Aib at position 16.

Embodiment 35

The peptide according to any one of the preceding embodiments comprising a sequence (SEQ ID NO: 982)
HSQGT X$_6$TSDX$_{10}$ SKX$_{13}$LD X$_{16}$RRAQ DFVQW LMNT wherein
X$_6$ is selected from the group consisting of 3-(3-Pyridyl)-L-alanine, 3-(4-Pyridyl)-L-alanine, and Phe;
X$_{10}$ is selected from the group consisting of 3-(3-Pyridyl)-L-alanine, 3-(4-Pyridyl)-L-alanine, and Tyr;
X$_{13}$ is selected from the group consisting of 3-(3-Pyridyl)-L-alanine, 3-(4-Pyridyl)-L-alanine, and Tyr;
X$_{16}$ is Aib,
optionally comprising up to 5 further amino acid modifications,
provided that at least one of X$_6$, X$_{10}$ or X$_{13}$ is 3-(3-Pyridyl)-L-alanine or 3-(4-Pyridyl)-L-alanine.

Embodiment 36

The peptide according to embodiment 35 comprising up to 4 further amino acid modifications.

Embodiment 37

The peptide according to any one of embodiments 35-36 comprising up to 3 further amino acid modifications.

Embodiment 38

The peptide according to any one of embodiments 35-37 comprising up to 2 further amino acid modifications.

Embodiment 39

The peptide according to any one of embodiments 35-38 comprising up to 1 further amino acid modification.

Embodiment 40

The peptide according to any one of embodiments 35-39 wherein
X$_6$ is 3-(3-Pyridyl)-L-alanine;
X$_{10}$ is Tyr;
X$_{13}$ is Tyr; and
X$_{16}$ is Aib.

Embodiment 41

The peptide according to embodiment 40 further comprising d-Gln at position 20.

Embodiment 42

The peptide according to embodiment 40 further comprising d-Asp at position 21.

Embodiment 43

The peptide according to embodiment 40 further comprising Asp at position 28 and Glu at position 29.

Embodiment 44

The peptide according to embodiment 40 comprising the sequence according to SEQ ID NO: 944.

Embodiment 45

The peptide according to any one of embodiments 35-39 wherein
X$_6$ is Phe;
X$_{10}$ is 3-(3-Pyridyl)-L-alanine;
X$_{13}$ is Tyr; and
X$_{16}$ is Aib.

Embodiment 46

The peptide according to embodiment 45 further comprising d-Gln at position 20.

Embodiment 47

The peptide according to embodiment 45 further comprising d-Asp at position 21.

Embodiment 48

The peptide according to embodiment 45 further comprising Asp at position 28 and Glu at position 29.

Embodiment 49

The peptide according to embodiment 45 comprising the sequence according to SEQ ID NO: 945.

Embodiment 50

The peptide according to any one of embodiments 35-39 wherein
X$_6$ is Phe;
X$_{10}$ is Tyr;
X$_{13}$ is 3-(3-Pyridyl)-L-alanine; and
X$_{16}$ is Aib.

Embodiment 51

The peptide according to embodiment 50 further comprising d-Gln at position 20.

Embodiment 52

The peptide according to embodiment 50 further comprising d-Asp at position 21.

Embodiment 53

The peptide according to embodiment 50 further comprising Asp at position 28 and Glu at position 29.

Embodiment 54

The peptide according to embodiment 50 comprising the sequence according to SEQ ID NO: 946.

Embodiment 55

The peptide according to any one of embodiments 35-39 wherein
$X_6$ is Phe;
$X_{10}$ is Tyr;
$X_{13}$ is 3-(4-Pyridyl)-L-alanine; and
$X_{16}$ is Aib.

Embodiment 56

The peptide according to embodiment 55 further comprising d-Gln at position 20.

Embodiment 57

The peptide according to embodiment 55 further comprising d-Asp at position 21.

Embodiment 58

The peptide according to embodiment 55 further comprising Asp at position 28 and Glu at position 29.

Embodiment 59

The peptide according to embodiment 55 comprising the sequence according to SEQ ID NO: 947.

Embodiment 60

The peptide according to any one of embodiments 35-39 wherein
$X_6$ is Phe;
$X_{10}$ is 3-(3-Pyridyl)-L-alanine;
$X_{13}$ is 3-(3-Pyridyl)-L-alanine; and
$X_{16}$ is Aib.

Embodiment 61

The peptide according to embodiment 60 further comprising d-Gln at position 20.

Embodiment 62

The peptide according to embodiment 60 further comprising d-Asp at position 21.

Embodiment 63

The peptide according to embodiment 60 further comprising Asp at position 28 and Glu at position 29.

Embodiment 64

The peptide according to embodiment 60 comprising the sequence according to SEQ ID NO: 948.

Embodiment 65

The peptide according to any one of embodiments 35-39 wherein
$X_6$ is Phe;
$X_{10}$ is 3-(4-Pyridyl)-L-alanine;
$X_{13}$ is 3-(4-Pyridyl)-L-alanine; and
$X_{16}$ is Aib.

Embodiment 66

The peptide according to embodiment 65 further comprising d-Gln at position 20.

Embodiment 67

The peptide according to embodiment 65 further comprising d-Asp at position 21.

Embodiment 68

The peptide according to embodiment 65 further comprising Asp at position 28 and Glu at position 29.

Embodiment 69

The peptide according to embodiment 65 comprising the sequence according to SEQ ID NO: 949.

Embodiment 70

The peptide according to any one of embodiments 35-39 wherein
$X_6$ is 3-(3-Pyridyl)-L-alanine;
$X_{10}$ is 3-(3-Pyridyl)-L-alanine;
$X_{13}$ is 3-(3-Pyridyl)-L-alanine; and
$X_{16}$ is Aib.

Embodiment 71

The peptide according to embodiment 70 further comprising d-Gln at position 20.

Embodiment 72

The peptide according to embodiment 70 further comprising d-Asp at position 21.

Embodiment 73

The peptide according to embodiment 70 further comprising Asp at position 28 and Glu at position 29.

Embodiment 74

The peptide according to embodiment 70 comprising the sequence according to SEQ ID NO: 950.

Embodiment 75

The peptide according to any one of embodiments 35-39 wherein
$X_6$ is 3-(4-Pyridyl)-L-alanine;
$X_{10}$ is 3-(4-Pyridyl)-L-alanine;
$X_{13}$ is 3-(4-Pyridyl)-L-alanine; and
$X_{16}$ is Aib.

Embodiment 76

The peptide according to embodiment 75 further comprising d-Gln at position 20.

Embodiment 77

The peptide according to embodiment 75 further comprising d-Asp at position 21.

Embodiment 78

The peptide according to embodiment 75 further comprising Asp at position 28 and Glu at position 29.

Embodiment 79

The peptide according to embodiment 75 comprising the sequence according to SEQ ID NO: 951.

Embodiment 80

The peptide according to any one of embodiments 35-39 wherein
$X_6$ is 3-(4-Pyridyl)-L-alanine;
$X_{10}$ is Tyr;
$X_{13}$ is Tyr; and
$X_{16}$ is Aib.

Embodiment 81

The peptide according to embodiment 80 further comprising d-Gln at position 20.

Embodiment 82

The peptide according to embodiment 80 further comprising d-Asp at position 21.

Embodiment 83

The peptide according to embodiment 80 further comprising Asp at position 28 and Glu at position 29.

Embodiment 84

The peptide according to any one of embodiments 35-39 wherein
$X_6$ is Phe;
$X_{10}$ is 3-(4-Pyridyl)-L-alanine;
$X_{13}$ is Tyr; and
$X_{16}$ is Aib.

Embodiment 85

The peptide according to embodiment 84 further comprising d-Gln at position 20.

Embodiment 86

The peptide according to embodiment 84 further comprising d-Asp at position 21.

Embodiment 87

The peptide according to embodiment 84 further comprising Asp at position 28 and Glu at position 29.

Embodiment 88

The peptide according to any of the preceding embodiments wherein the peptide further comprises a C-terminal extension of SEQ ID NO: 820 (GPSSGAPPPS), SEQ ID NO: 821 (KRNRNNIA), or SEQ ID NO: 822 (KRNR) linked to the amino acid at position 29 via a peptide bond.

Embodiment 89

The peptide according to any one of the preceding embodiments wherein the peptide is covalently linked to hydrophilic moiety.

Embodiment 90

The peptide according to embodiment 89 wherein the hydrophilic moiety is poly ethylene glycol (PEG).

Embodiment 91

The peptide according to any one of the preceding embodiments wherein the peptide is covalently linked to an acyl or an alkyl group.

Embodiment 92

The peptide according to embodiment 91 wherein the acyl group or the alkyl group is attached to a side chain of an amino acid through a spacer.

Embodiment 93

The peptide according to any one of embodiments 91-92 wherein the acyl group or alkyl group comprises a carboxylate at the free end of the acyl or the alkyl group.

Embodiment 94

The peptide according to any one of the preceding embodiments for use as a medicament.

Embodiment 95

The peptide according to any one of the preceding embodiments for use in the treatment of hypoglycemia.

Embodiment 96

The peptide according to any one of the preceding embodiments wherein the peptide is co-administered with insulin.

Embodiment 97

A pharmaceutical composition comprising the peptide according to any one of the preceding embodiments and pharmaceutically acceptable excipients.

Example 1

General Synthesis Protocol

Glucagon analogs were synthesized using HBTU-activated "Fast Boc" single coupling starting from 0.2 mmole of Boc Thr(OBzl)Pam resin on a modified Applied Biosystem 430 A peptide synthesizer. Boc amino acids and HBTU were obtained from Midwest Biotech (Fishers, Ind.). Side chain protecting groups used were: Arg(Tos), Asn(Xan), Asp(O-cHex), Cys(pMeBzl), His(Bom), Lys(2Cl-Z), Ser(OBzl), Thr(OBzl), Tyr(2Br-Z), and Trp(CHO). The side-chain protecting group on the N-terminal His was Boc.

Each completed peptidyl resin was treated with a solution of 20% piperdine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-Maleimido)

Typically, the glucagon Cys analog is dissolved in phosphate buffered saline (5-10 mg/ml) and 0.01M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated analogs.

Example 2

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (31-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following: % Specific Binding= ((Bound-NSB)/(Total bound-NSB))×100. $IC_{50}$ values were determined by using Origin software (OriginLab, Northampton, Mass.).

Example 3

Functional Assay-cAMP Synthesis

The ability of glucagon analogs to induce cAMP was measured in a firefly luciferase-based reporter assay. HEK293 cells co-transfected with either glucagon- or GLP-1 receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). The luminescent light output indicates activation of the luciferase reporter gene, which in turn is a measure of the activation of the receptor. Effective 50% concentrations ("$EC_{50}$") were calculated by using Origin software (OriginLab, Northampton, Mass. $EC_{50}$ is the concentration of the peptide that produces 50% of the peptide's maximum activation response at the indicated receptor. A relatively lower $EC_{50}$ indicates that a peptide is relatively more potent at that receptor, while a higher EC50 indicates that a peptide is less potent.

Example 4

Synthesis of Glucagon Lactams 285 mg (0.2 mmole) methoxybenzhydrylamine resin (Midwest Biotech) was added to a 60 mL reaction vessels and the following sequence was assembled on a modified Applied Biosystems 430A peptide synthesizer using Boc DEPBT-activated single couplings.

The following side chain protecting groups were used: Arg(Tos), Asp(OcHx), Asn(Xan), Glu(OFm), His(BOM), Lys(Fmoc), Ser(Bzl), Thr(Bzl), Trp(CHO), Tyr(Br-Z). As an example, Lys(Cl-Z) was used to protect the native Lys at position 12 if lactams were constructed from 16-20, 20-24, or 24-28. The completed peptidyl resin was treated with 20% piperidine/dimethylformamide for one hour with rotation to remove the Trp formyl group as well as the Fmoc and OFm protection from Lys12 and Glu16. Upon confirmation of removal by a positive ninhydrin test, the resin was washed with dimethylformamide, followed by dichloromethane and than again with dimethylformamide. The resin was treated with 520 mg (1 mmole) Benzotriazole-1-yl-oxy-tris-pyrrolidino-phosphonium hexafluorophosphate (PyB OP) in dimethylformamide and diisopropylethylamine (DIEA). The reaction proceeded for 8-10 hours and the cyclization was confirmed by a negative ninhydrin reaction. The resin was washed with dimethylformamide, followed by dichloromethane and subsequently treated with trifluoroacetic acid for 10 minutes. The removal of the Boc group was confirmed by a positive ninhydrin reaction. The resin was washed with dimethylformamide and dichloromethane and dried before being transferred to a hydrofluoric acid (HF) reaction vessel. 500 µL p-cresol was added along with a magnetic stir bar. The vessel was attached to the HF apparatus (Peninsula Labs), cooled in a dry ice/methanol bath, evacuated, and approximately 10 mL of liquid hydrofluoric acid was condensed into the vessel. The reaction was stirred for 1 hour in an ice bath and the HF was subsequently removed in vacuo. The residue was suspended in ethyl ether; the solids were filtered, washed with ether, and the peptide was solubilized with 150 mL 20% acetonitrile/1% acetic acid.

An analytical HPLC analysis of the crude solubilized peptide was conducted under the following conditions [4.6× 30 mm Xterra C8, 1.50 mL/min, 220 nm, A buffer 0.1% TFA/10% ACN, B buffer 0.1% TFA/100% ACN, gradient 5-95% B over 15 minutes]. The extract was diluted twofold with water and loaded onto a 2.2×25 cm Vydac C4 preparative reverse phase column and eluted using an acetonitrile gradient on a Waters HPLC system (A buffer of 0.1% TFA/10% ACN, B buffer of 0.1% TFA/10% CAN and a gradient of 0-100% B over 120 minutes at a flow of 15.00 ml/min. HPLC analysis of the purified peptide demonstrated greater than 95% purity and electrospray ionization mass spectral analysis confirmed a mass of 3506 Da for the 12-16 lactam. Lactams from 16-20, 20-24, and 24-28 were prepared similarly.

Example 5

Preparation of Acylated and/or PEGylated Peptides

Acylated and/or PEGylated peptides are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., Int. J. Peptide Protein Res. 40: 180-193 (1992). For acylated peptides, the target amino acid residue to be acylated (e.g., position ten) is substituted with an N ε-FMOC lysine residue. Treatment of the completed N-terminally BOC protected peptide with 20% piperidine in DMF for 30 minutes removes FMOC/formyl groups. Coupling to the free ε-amino Lys residue is achieved by coupling a ten-fold molar excess of either an FMOC-protected spacer amino acid (ex. FMOC-(N-BOC)-Tryptophan-OH) or acyl chain (ex. C17-COOH) and PyBOP or DEPBT coupling reagent in DMF/DIEA. Subsequent removal of the spacer amino acid's FMOC group is followed by repetition of coupling with an acyl chain. Final treatment with 100% TFA results in removal of any side chain protecting groups and the N-terminal BOC group. Peptide resins are neutralized with 5% DIEA/DMF, are dried, and then are cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column is used for the purification. Acylated peptide analogs generally complete elution by a buffer ratio of 20:80. Portions are pooled together and checked for purity on an analytical RP-HPLC. Pure fractions are lyophilized yielding white, solid peptides.

If a peptide comprises a lactam bridge and target residues to be acylated, acylation is carried out as described above upon addition of that amino acid to the peptide backbone.

For peptide pegylation, 40 kDa methoxy poly(ethylene glycol) maleimido-propionamide (Chirotech Technology Ltd.) is reacted with a molar equivalent of peptide in 7M Urea, 50 mM Tris-HCl uffer using the minimal amount of solvent needed to dissolve both peptide and PEG into a clear solution (generally less than 2 mL for a reaction using 2-3 mg peptide). Vigorous stirring at room temperature commences for 4-6 hours and the reaction is analyzed by analytical RP-HPLC. PEGylated products appear distinctly from the starting material with decreased retention times. Purification is performed on a Vydac C4 column with conditions similar to those used for the initial peptide purification. Elution typically occurs around buffer ratios of 50:50. Fractions of pure PEGylated peptide are collected and lyophilized.

Example 6

Enhanced Soluble Glucagon Peptides

Native Glucagon 1 is a 29 amino acid pancreatic hormone whose primary physiological role is the mobilization of hepatic glucose achieved through stimulation of glycogenolysis, gluconeogenesis and suppression of glycogen synthesis. Intact glucagon response, an essential component of glycemic control in healthy individuals is often impaired in diabetic patients. This deficiency can present a particularly acute risk for insulin dependent (Type 1) diabetics who encounter hypoglycemia in the course of insulin therapy. In these instances patients may require emergency intervention in the form of a subcutaneous administration of glucagon. Due to the tendency of native glucagon to undergo chemical degradation and form insoluble fibrils, it is supplied as a lyophilized powder which use necessitates reconstitution in a sterile, acidic diluent immediately prior to its administration. The inconvenience and time interval required for its preparation and administration poses additional risk. The adverse biophysical properties of native glucagon also hinder its use number of exploratory settings including mini-dosing protocols and in conjunction with insulin co-administered via a bi-hormonal pump.

The incorporation of 3-pyridyl-alanine (3-Pal) has been previously noted to improve solubility characteristics of proteins including for example, increasing the solubility of a series of CGRP antagonist peptides while maintaining their potency (Yan, et al., J. P. Discovery of potent, cyclic calcitonin gene-related peptide receptor antagonists. *J. Pept. Sci.* 2011, 17, 383-386). Our approach in the present study involved a systematic evaluation of single and multiple 3-Pyridyl-alanine (3-Pal) and 4-Pyridyl-alanine (4-Pal) substitutions at position 6,10 and 13 of glucagon (See Table 1).

Experimental Procedures

Chemistry.

Glucagon peptides comprising pyridyl-alanine were prepared by automated (CSBio model CS336X) Fmoc/tBu solid-phase methodology starting with pre-loaded Fmoc-Thr (tBu)-Wang resin (Aapptec, Louisvile, Ky.) and HCTU/DIPEA activation. The side chain protecting group scheme consisted of Arg(Pbf); Asp(OtBu); Asn(Trt); Gln(Trt); His (Trt); Lys(Boc); Ser(tBu); Thr(tBu); Tyr(tBu); and Trp(Boc). Abbreviations: Fmoc=fluorenylmethyloxycarbonyl, Pbf=2, 2,4,6,7-pentamethyldihydrobenzofuran-5-sulfonyl, OtBu=tert-butyl ester, Trt=trityl, Boc=tert-butyloxycarbonyl, and tBu=tert-butyl ether, HCTU=2-(6-Chloro-1H-benzotriazole-1-yl)-1,1,3,3-tetramethylaminium hexafluorophosphate, DIPEA=N,N-diisopropylethylamine).

Fmoc-(3-pyridyl)-L-alanine and Fmoc-(4-pyridyl)-L-alanine were coupled in the course of automated assembly. All regular residue were purchased from Midwest Biotech (Fisher, Ind.), 3- and 4-pyridyl-L-alanines were obtained from Aapptec (Louisville, Ky.), HCTU from Peptide International (Louisville, Ky.), DIPEA from Sigma-Aldrich (St. Louis, Mo.). Peptides were cleaved from the resin and deprotected by treatment with TFA containing 2.5% Tis (triisopropylsilane), 2.5% water, 1.5% methanol, 2.5% phenol, 0.5% DODT [2,2'-(Ethylenedioxy)-diethenethio] and 0.5% of Me$_2$S (dimethyl sulfide). Peptides were purified by preparative RP-HPLC on an Amberchrom-XT20 (21.2×250 mm, DOW) and/or Kinetex C8 (AXIA packed, 21.2×250 mm, 5 µm, Phenomenex) column with 0.05% TFA/H$_2$O and 0.05% TFA/CH$_3$CN as elution buffers. Native glucagon (Eli Lilly and Co., Indianapolis, Ind.) was re-purified under the above conditions ensure identical counter-ions content.

Purified peptides were analyzed and characterized by LC-MS (1260 Infinity-6120 Quadrupole LCMS, Agilent) on Kinetex C8 (4.6×75 mm, 2.6 µm, Phenomenex) with 0.05% TFA/H$_2$O and 0.05% TFA/CH$_3$CN as eluents employing 5% B to 70% B in 15 min gradient with 2.5 min delay. Peptide's concentration was assessed based on UV absorption at $\lambda$=280 nm measured on a NanoDrop 1000 spectrophotometer (Thermo Scientific, Wilmington, Del.). Extinction coefficients at $\lambda$=280 nm were calculated using on-line Peptide Property Calculator (Innovagen, PepCalc.com).

Solubility Assay.

1 or 5 mg of pre-lyophilized peptide in 2 mL Eppendorf tube was treated with 200-400 uL of phosphate buffer (PBS: 50 mM sodium phosphate, 150 mM of sodium chloride, pH7.4). Samples were then vortexed and sonicated for 10 min then equilibrated at RT for 1H, and then centrifuged at 10 krpms for 10 min Concentration of the peptides in obtained supernatant was determined by measuring UV absorbance at $\lambda$=280 nm. From a highly concentrated stock solution of analogues 7-10, dilution to 10, 5, and 1 mg/mL aliquots were made while evaluating any appearance of precipitate. Based on calculated concentration, samples with the peptide pellet were then further diluted with phosphate buffer to ~4-5 mg/mL, vortexed, sonicated for 5 min and then equilibrated for 1 h, centrifuged and concentration of the stock was assessed in similar manner Undisturbed aliquots were then equilibrated at 4° C. for ~20 h, centrifuged again and concentration of the peptides was re-evaluated. Concentration in aliquots was reassessed as previously with UV absorbance. Change in peptide concentration was evaluated after 48 h and 7 days of storage at 4° C.

Thioflavin T (ThT) Spectroscopic Assay

Principle:

Thioflavin T (ThT) is a benzothiazole salt obtained by the methylation of dehydrothiotoluidine with methanol in the presence of hydrochloric acid. ThT is used as a dye to visualize and quantify the presence or fibrilization of misfolded protein aggregates, or amyloid, both in vitro and in vivo (e.g.,plaques composed of amyloid beta found in the brains of Alzheimer's disease patients; plaques of PrP fibrils found in brains of CGD patients).

The Thioflavin T (ThT) Assay measures changes of in fluorescence intensity of ThT upon binding to amyloid fibrils. The enhanced fluorescence can be observed by fluorescence microscopy or by fluorescent spectroscopy. The spectroscopic assay is commonly used to monitor fibrilization over time, but the assay is not strictly quantitative and differences in binding have been observed for samples after lyophilization.

Thioflavin-T Fluorescence Assay Protocol:

1. Prepare a ThT stock solution by adding 8 mg ThT to 10 mL phosphate buffer (10 mM phosphate, 150 mM NaCl, pH 7.0) and filter through a 0.2 µm syringe filter. This stock solution should be stored in the dark and is stable for about one week.

2. Dilute the stock solution into the phosphate buffer (1 mL ThT stock to 50 mL buffer) on the day of analysis to generate the working solution.

3. Measure the fluorescence intensity of 1 mL working solution by excitation at 440 nm (slitwidth 5 nm) and emission 482 nm (slitwidth 10 nm), averaging over 60 s.

4. Add an aliquot of untreated protein solution (5-10 µL) to the cuvette, stir for 1 min, and measure the intensity over 60 s. This serves as the control sample.

5. Repeat steps 3-4 with 5-10 µL of the aggregated protein solution. A measured intensity above the control sample is indicative of amyloid fibrils.

Aggregation.

Lyophilized peptides were dissolved in appropriate buffer at concentration ~8-9 mg/mL (1-5 in 0.1N hydrochloric acid; 7, 9 and 11 in 50 mM Sodium Phosphate, 150 mM of sodium chloride, pH7.4). Exact concentration was calculated based on UV absorbance at $\lambda$=280 nm and all samples were dissolved further down to equal concentration of 5 mg/mL. Then all were incubated at 37° C. for 48H without agitation followed by 48H at 40° C. with agitation of the magnetic stir bar at 300 rmps. Fibrillation was measured according to modified Thioflavin-T fluorescence assay protocol. 8 mg of Thioflavin-T (ThT) was dissolved in 10 mL of phosphate buffer (50 mM Sodium Phosphate, 150 mM of sodium chloride, pH7.4). Solution was filtered through 0.22 µm syringe filter and stored at 4° C. in dark. Prior to experiment the 0.3 mL of ThT stock solution was further diluted in 15 mL of the phosphate buffer. 5 µL of investigated peptide solution at 5 mg/mL was added to 400 µL of working solution of ThT in phosphate buffer. Solution was incubated for 20 to 30 min. Then fluorescence intensity was measured on Perkin-Elmer LS50B Luminescence Spectrometer (Perkin-Elmer, Waltham, Mass.) with following experimental parameters: 350 µL of peptide-ThT solution in sub-micro quartz cuvette [path length=10 mm; 12.5 mm×12.5 mm×45 mm; window 2 mm×8 mm; Z=15 mm] (Sterna Cells, Atascadero, Calif.) excitation $\lambda$=450 nm (slitwidth 5 nm); emission $\lambda$=482 nm (slitwidth 10 nm) integration 10 sec. Signal averaged from 4 consecutive points. The standard S1 (virgin solution of insulin in phosphate buffer at 1 mg/mL; 25 µL in 400 µL ThT working solution) and S2 (previously aggregated solution of insulin ~1 mg/mL; 25 µL in 400 µL ThT working solution) was checked alongside investigated glucagon peptides (See FIG. 2).

Stability.

Figure 3:
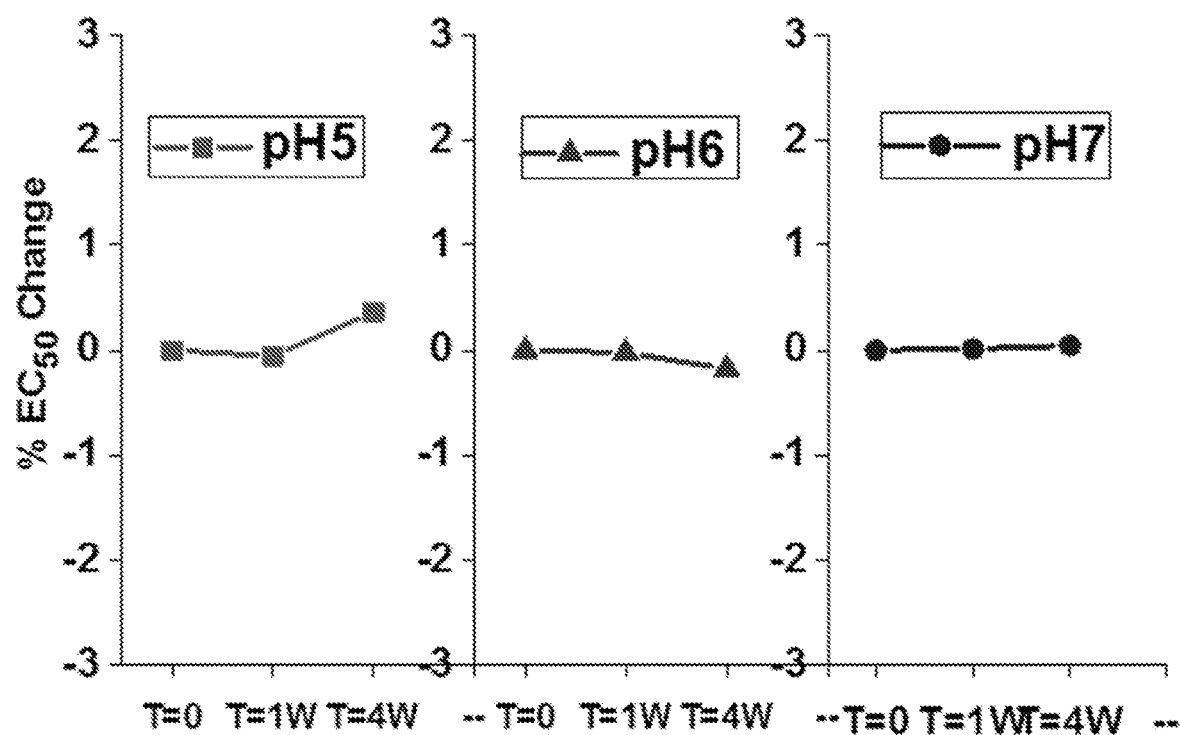
FIG. 3 Durability of biological response and chemical stability of analog 9 was measured through in vitro potency at pH 5, 6 and 7 over a 4 weeks period.

2.6 mg of the analog 9 was dissolved in 0.5 mL of phosphate buffer (50 mM Sodium Phosphate, 150 mM of sodium chloride) pH adjusted to 5, 6 and 7. Samples were vortexed and fully dissolved peptide solution was filtered over 0.22 µm syringe filter into sterilized Eppendorf tube. Concentration was assessed as previously described. Final ~800 µL of 2.0 mg/mL solution was made in sterilized 2 mL glass vial equipped with sterilized magnetic stir bar. Reference sample at T=0 was withdrawn and stored at −45° C., rest of the solutions were capped, sealed with paraffin film and incubated at 37° C.; agitated at 200 rpms. Test samples were withdrawn at 1 and 4 week time point. From withdrawn aliquots LC-MS analyze was run as described previously and samples in DMEM buffer for the bioassay were prepared. Glucagon Receptor-mediated cAMP Accumulation Assay was performed as previously described (see Example 3). Stability over 4 weeks are shown in FIG. 3.

In vivo RAT.

Male Wistar rats (Harlan, Ind.; BW 504±4 g) were housed on a 12:12 h light-dark cycle (8 am-8 pm lights on) at 22° C. and constant humidity with free access to standard chow (Teklad LM-485) and water, except as noted. The food was removed at the onset of the light phase, 3 hours prior the intraperitoneal administration of the compounds. The blood glucose level was determined at the intervals indicated using a handheld glucometer (Freestyle, Abbot). All studies were approved by and performed according to the guidelines of the Institutional Animal Care and Use Committee of the University of Cincinnati. The statistical analysis of the results obtained in the in vivo experiments was performed using Prism 6.0h (GraphPad Software, Calif.) applying One-way ANOVA followed by Dunnett's tests, using the insulin group as control. P values lower than 0.05 were considered significant ( P<0.01; * P<0.001). The results are presented as means±SEM of eight replicates per group. In all in vivo experiments, 50 mM sodium phosphate with 150 mM sodium chloride pH 7.4 buffer was used as a vehicle. See FIG. 4A-4D.

Pig Study.

Male diabetic Yucatan miniature swine (4 animals/group) were fed and administered NPH insulin at 8:00 AM and at 12 h prior to the initiation of the study, then fasted until the completion of the final blood glucose measurements. Insulin NPH doses were adjusted based on glucose levels and the animals were randomized to achieve balanced glucose levels across groups. On the day of the study the animals were administered a subcutaneous injection 0.5 U/kg of insulin detemir at the 0 time point and 10 nmoles/kg of either analog 9 or native glucagon 1 at the 240 minute timepoint. Blood glucose was measured at −5, 0 (Pre-Dose), 30, 60, 120, 240, 245, 250, 260, 280, 300, 330, 360 and 480 minutes using a handheld glucometer. The same instrument was used for all animals and two readings were taken per time point to insure consistency. The statistical analysis of the results obtained in the in vivo experiments was performed using Prism 6.0h (GraphPad Software, Calif.) applying regular two-way ANOVA followed by Sidak multiple comparison test between the two treatments. P values lower than 0.05 were considered significant ( P<0.01; * P<0.001). The results are presented as means±SEM of four replicates per group. See FIG. 5.

Results

The novel glucagon peptides of Table 1 were synthesized by automated Fmoc/tBu solid-phase peptide synthesis and are summarized in Table 1. Our initial selection criteria emphasized aqueous solubility at pH 7.0 and in vitro potency as assessed by a luciferase based glucagon assay (see Table 2). The starting point of our structure-activity study was [Aib$^{16}$]Glc(1-29) 2, an analog which has been demonstrated as possessing enhanced biophysical stability as well as resistance to aspartimide formation at Asp$^{15}$-Ser$^{16}$ by virtue of the Aib$^{16}$ substituent. Successive replacement of Phe$^6$, Tyr$^{10}$ and Tyr$^{13}$ correlated with (additive effect on solubility) increasing solubility in both the 3-Pal and 4-Pal substituted analogs: single substitution increased solubility to >1 mg/ml, while double or triple substitution increased it to over 10 mg/ml. This was attributed to the decreased hydrophobic character of the peptides and was also reflected in the trend toward earlier HPLC elution time (Table 1).

TABLE 1

Glucagon analogs.

| Cmp | Sequence | Rt [min] | Th. MW | Exp. MW [H+] | LCMS ions [m/z] |
|---|---|---|---|---|---|
| 1 | HSQGTFTSDYSKYLDSRRAQDFVQWLMNT (SEQ ID NO: 1) | 11.462 | 3482.8 | 3483.2 | 871.5; 1161.7; 1742.2 |
| 2 | HSQGTFTSDYSKYLDZRRAQDFVQWLMNT (SEQ ID NO: 943) | 11.824 | 3480.8 | 3481.0 | 870.9; 1161.0; 1741.2 |
| 3 | HSQGTXTSDYSKYLDZRRAQDFVQWLMNT (SEQ ID NO: 944) | 11.471 | 3481.8 | 3482.2 | 871.4; 1161.1; 1741.8 |
| 4 | HSQGTFTSDXSKYLDZRRAQDFVQWLMNT (SEQ ID NO: 945) | 11.432 | 3465.8 | 3465.9 | 867.0; 1156.0; 1733.8 |
| 5 | HSQGTFTSDYSKXLDZRRAQDFVQWLMNT (SEQ ID NO: 946) | 11.490 | 3465.8 | 3465.9 | 867.1; 1155.8; 1733.3 |
| 6 | HSQGTFTSDYSKULDZRRAQDFVQWLMNT (SEQ ID NO: 947) | 11.402 | 3465.8 | 3466.2 | 867.3; 1155.9; 1733.9 |
| 7 | HSQGTFTSDXSKXLDZRRAQDFVQWLMNT (SEQ ID NO: 948) | 11.074 | 3450.8 | 3450.7 | 863.4; 1151.0; 1725.8 |
| 8 | HSQGTFTSDUSKULDZRRAQDFVQWLMNT (SEQ ID NO: 949) | 11.077 | 3450.8 | 3451.2 | 863.6; 1151.0; 1726.1 |
| 9 | HSQGTXTSDXSKXLDZRRAQDFVQWLMNT (SEQ ID NO: 950) | 10.874 | 3451.7 | 3452.6 | 863.7; 1151.5; 1727.2 |
| 10 | HSQGTUTSDUSKULDZRRAQDFVQWLMNT (SEQ ID NO: 951) | 10.813 | 3451.7 | 3452.2 | 863.7; 1151.3; 1726.9 |
| 11 | HSQGTXTSDXSKXLDZRRAQDXVQWLMNT (SEQ ID NO: 952) | 8.935 | 3452.7 | 3453.3 | 864.0; 1151.7; 1727.4 |

Z = Aib; X = 3-Pal; U = 4-Pal

TABLE 2

Solubility and bioactivity of Glucagon analogs.

| Compound | Solubility [mg/mL] | EC$_{50}$ [nM] (SDV) | n | % bioactivity of GCG |
|---|---|---|---|---|
| 1 | <1 | 0.0212 (0.0137) | 28 | |
| 2 | <1 | 0.0399 (0.0113) | 10 | 51 |
| 3 | >1 | 0.0170 (0.0019) | 5 | 119 |
| 4 | >1 | 0.0268 (0.0031) | 3 | 76 |
| 5 | >1 | 0.0379 (0.0173) | 3 | 54 |
| 6 | >1 | 0.0339 (0.0143) | 3 | 60 |
| 7 | >10 | 0.0359 (0.0193) | 7 | 57 |
| 8 | >10 | 0.0309 (0.0101) | 3 | 66 |
| 9 | >10 | 0.0714 (0.0528) | 24 | 28 |
| 10 | >10 | 0.0843 (0.0334) | 3 | 24 |
| 11 | >10 | 2.3250 (1.976) | 7 | 1 |

Figure 2:
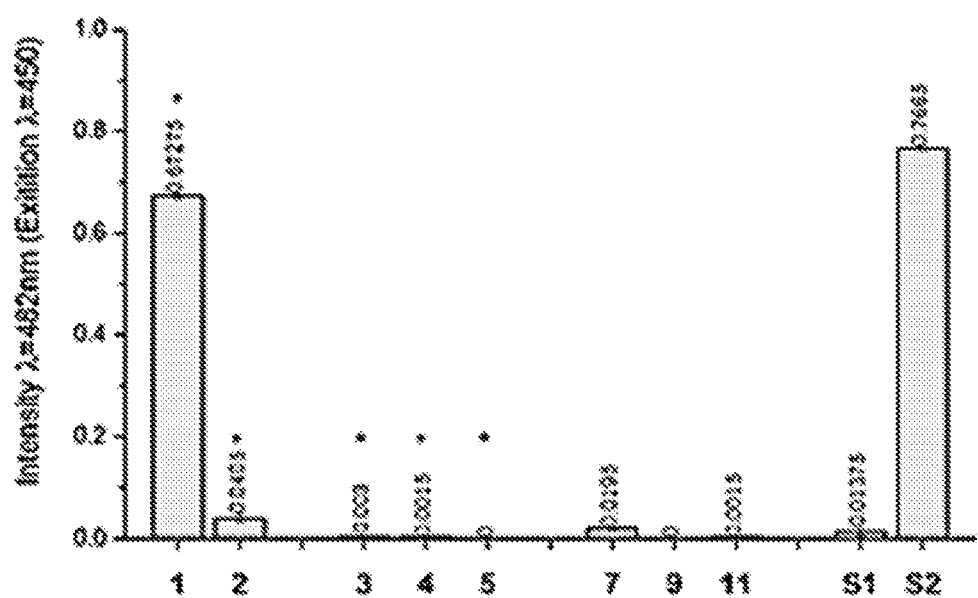
FIG. 2 is a bar graph showing the resistance/stability of the glucagon peptides of Table 1 to fibrillation. Analog 9 (SEQ ID NO: 950) proved resistant to fibrillation as measured by the thioflavin-T fluorescence assay as disclosed in Example 6 using native glucagon (1) and insulin as positive controls (S1 and S2).
Figure 4B:
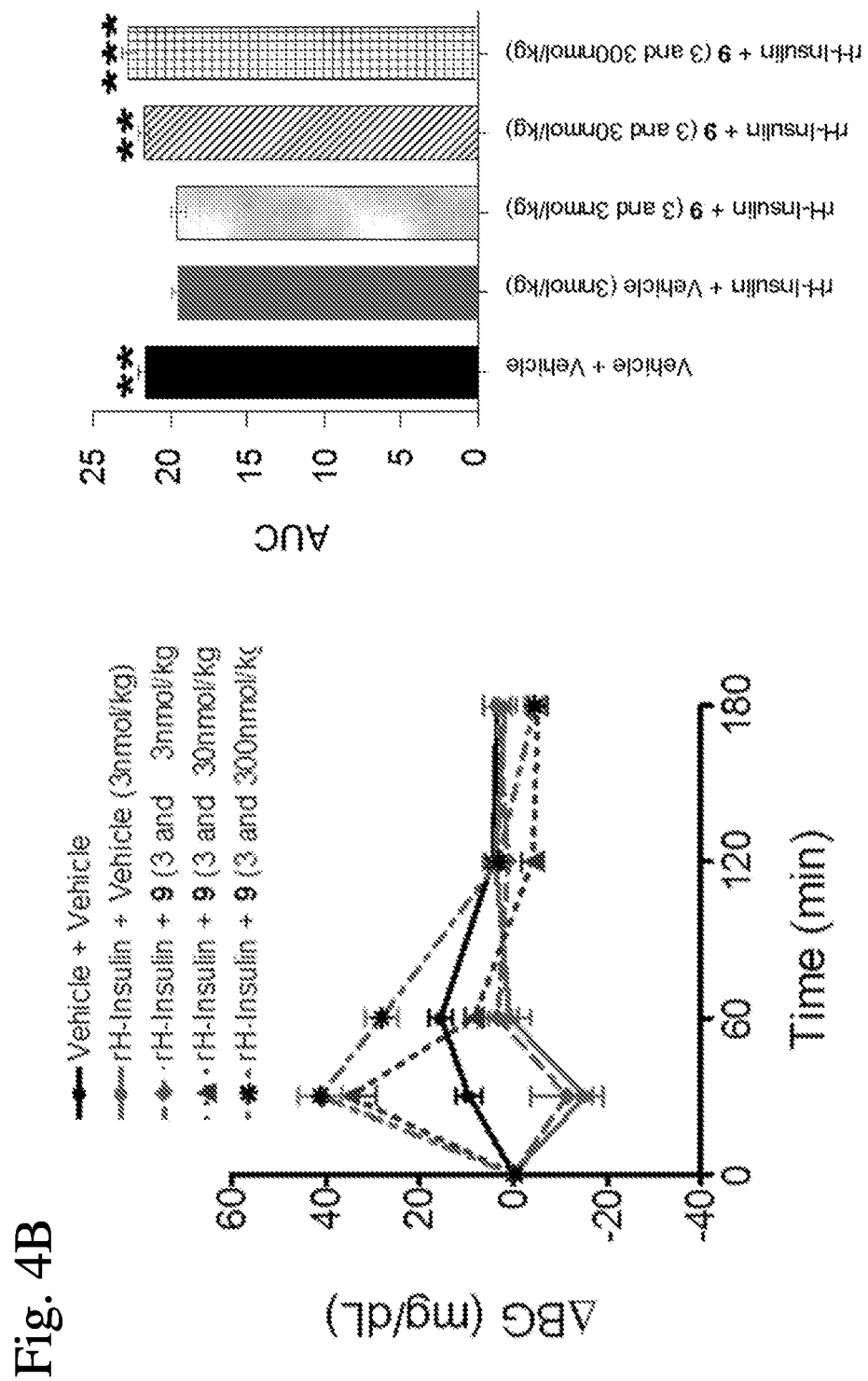
Figure 5:
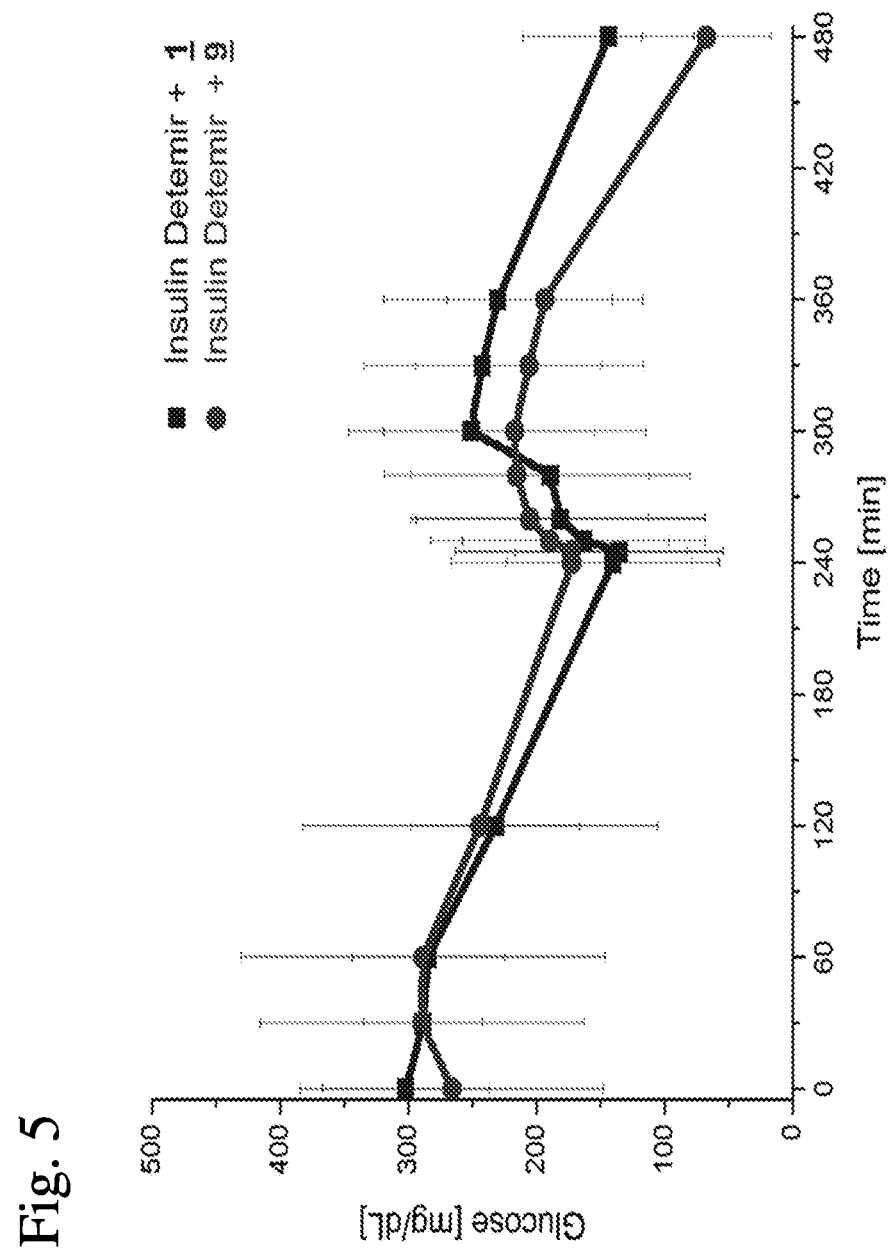
FIG. 5 is a graph presenting data demonstrating the ability of analog 9 to reverse insulin induced hypoglycemia in diabetic pigs. Diabetic pigs (4/group) were treated with insulin detemir (Levemir) a long acting insulin. At the 4-hour time point the animals were challenged with a dose of either analog 9 or native glucagon (1).

A luciferase-based glucagon assay was used to assess the in vitro efficacy, which was maintained in the case of the mono, di and even tri-substituted analogs in the 3-Pal and 4-Pal series, with only the tetra substituted analog 11 exhibiting lower potency (see Table 2). The fully potent and highly soluble (>10 mg/ml) analogs 7 and 9 were subjected more rigorous solubility and formulation studies which examined PBS solubility at 4° C. for 48 hrs and 7 day intervals relative to their initial solubility. Analog 9 maintained full solubility under all conditions while analog 7 exhibited reduced solubility after 7 days. Analog 9 also proved resistant to fibrillation as measured by the thioflavin-T fluorescence method using native glucagon and insulin as positive controls (FIG. 2). Durability of biological response and chemical stability was measured through in vitro potency at pH 5, 6 and 7 over a 4 weeks period (FIG. 3). The definitive evaluation of analog 9's pharmacological performance was obtained through pilot in vivo studies in rats and pigs. The first study involved lean rats which were administered escalating doses of native glucagon (FIG. 4A) or analog 9 (FIG. 4B) with a fixed dose of insulin. The same protocol was repeated comparing analog 9 with native glucagon in the same animal cohort (FIG. 4C). The "stand-alone" hyperglycemic effect of analog 9 in the absence of exogenous insulin is shown in FIG. 4D, again using native glucagon as comparator. A final validation was provided by the ability of analog 9 to reverse insulin induced hypoglycemia in diabetic pigs (FIG. 5). In this experiment diabetic pigs (4/group) were treated with insulin detemir (Levemir) a long acting insulin. At the 4-hour timepoint the animals were challenged with a dose of either analog 9 or native glucagon 1. In summary, analog 9 represents one embodiment of a glucagon analog having the requisite biophysical, chemical, pharmacological properties to be a ready-to-use glucagon therapeutic.

Example 7

Glucagon Analogs Comprising D-Amino Acid Substitutions

Figure 6A:
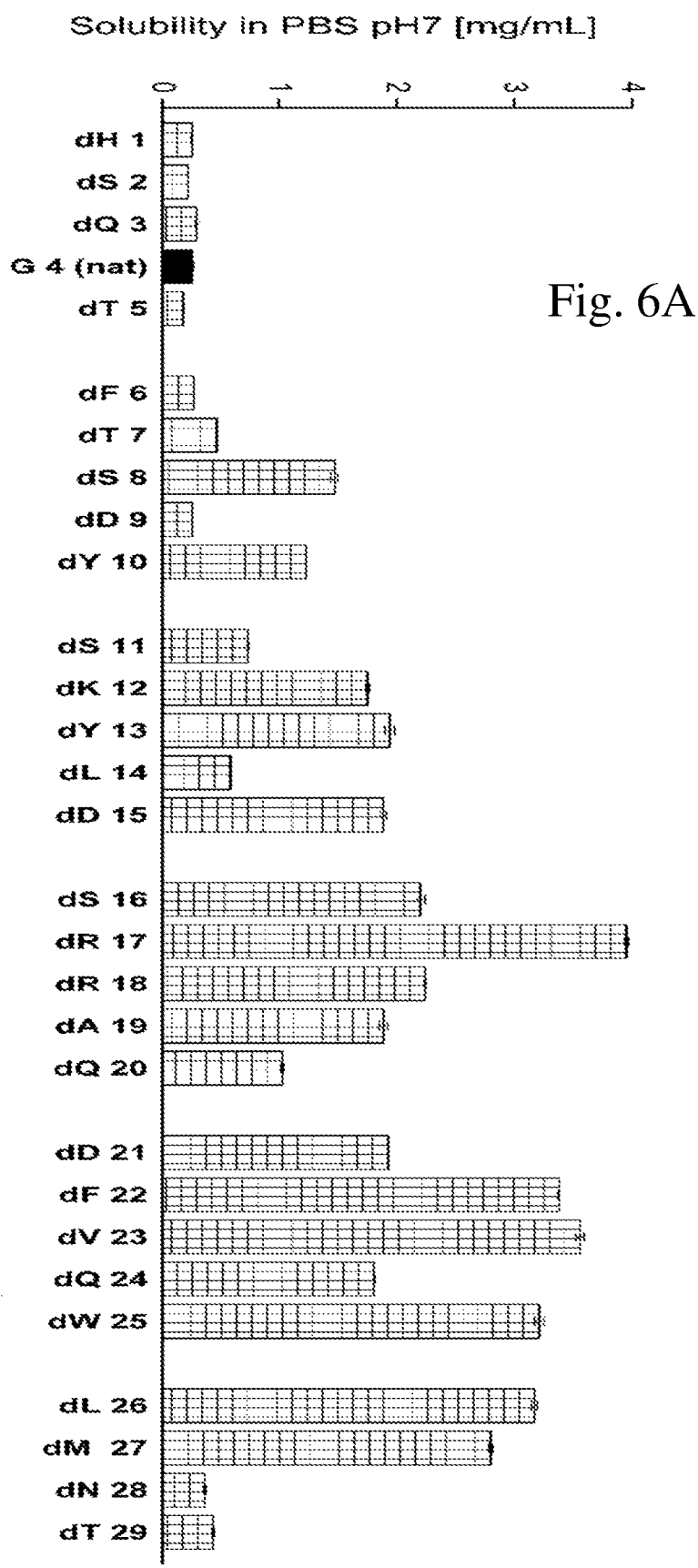
FIGS. 6A-6C are bar graphs demonstrating the activity of a series of glucagon peptides, each comprising a single substitution of a native amino acid with its corresponding D-isomer.
Figure 6B:
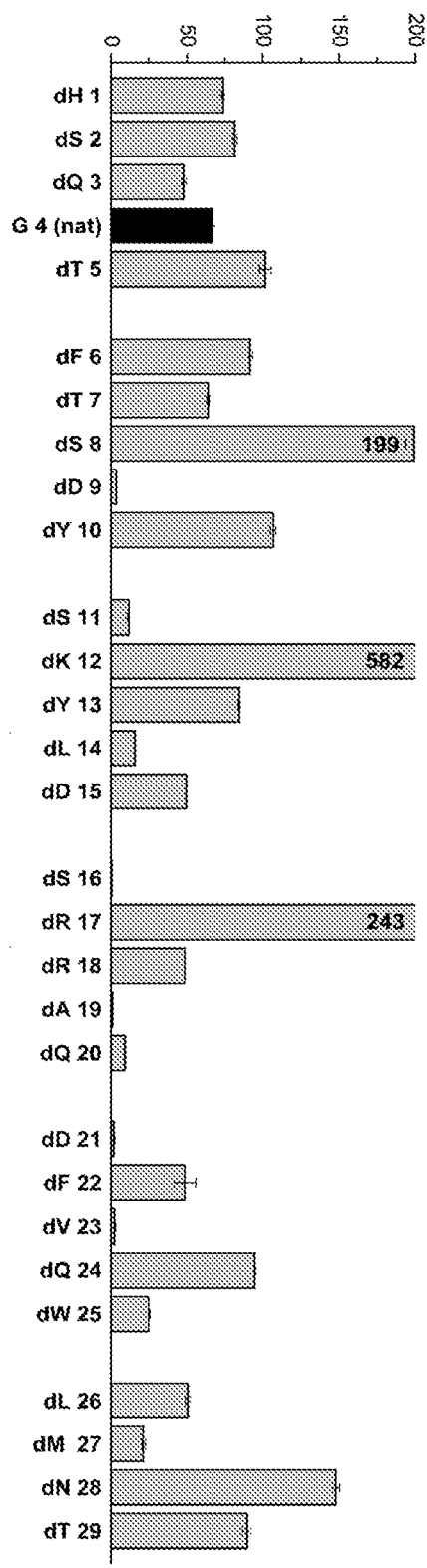
Figure 6C:
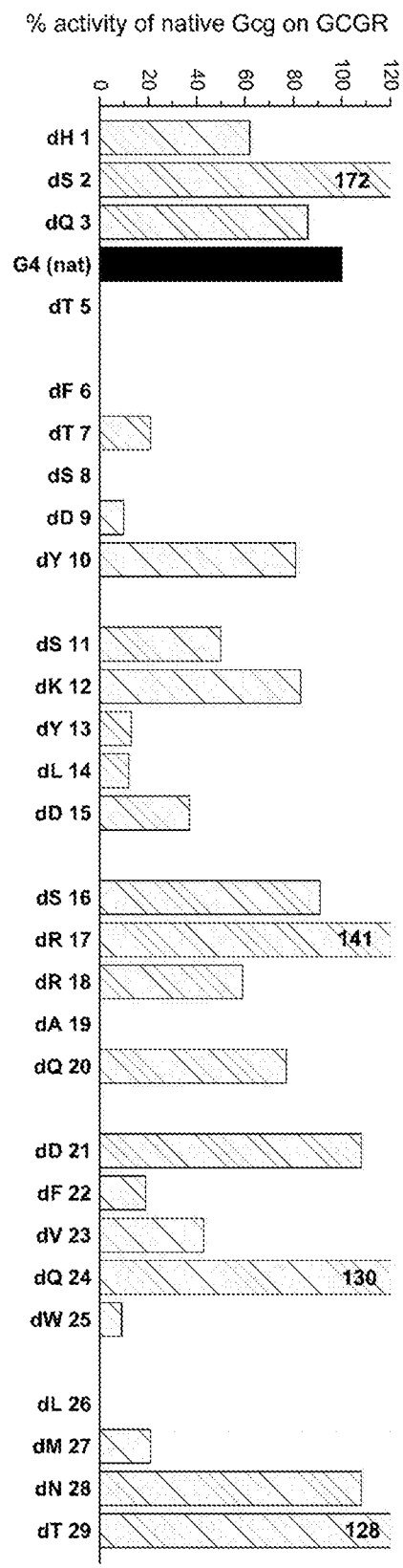

To investigate the impact of D-amino acid substitutions on the solubility of glucagon, a series of glucagon analogs were prepared having a single modification, where the native amino acid at each position of the native glucagon sequence was systematically substituted with the corresponding D-amino acid. The 29 analogs were then each tested for solubility, stability (resistance to fibrillation) and activity at the glucagon receptor. FIG. 6A demonstrates the solubility of each analog, in PBS at pH 7 and room temperature. FIG. 6B provides data regarding the aggregation/fibrillation of each modified glucagon analog (as measured by the thioflavin-T fluorescence assay as disclosed in Example 6). FIG. 6C provides data regarding the activity of each modified glucagon analog using the assay as disclosed in Example 3.

Table 3 provides the activity at the glucagon and GLP-1 receptors of various glucagon analogs comprising substitutions of D-amino acids in combination with pyridyl-alanine to improve glucagon solubility.

TABLE 3

| Peptide | Sequence | hGcgR EC$_{50}$ (pM) | hGLP-1R EC$_{50}$ (pM) |
|---|---|---|---|
| SEQ ID NO: 1 | Native | 63 | >10000 |
| SEQ ID NO: 974 | Aib16, q20 | 49 | 4428 |
| SEQ ID NO: 971 | 3-Pal10, Aib16, q20 | 86 | >10000 |
| SEQ ID NO: 980 | Aib16, q20, D28 | 33 | 7480 |
| SEQ ID NO: 981 | Aib16, q20, D28, E29 | 18 | >10000 |

Figures 7A, 7B:
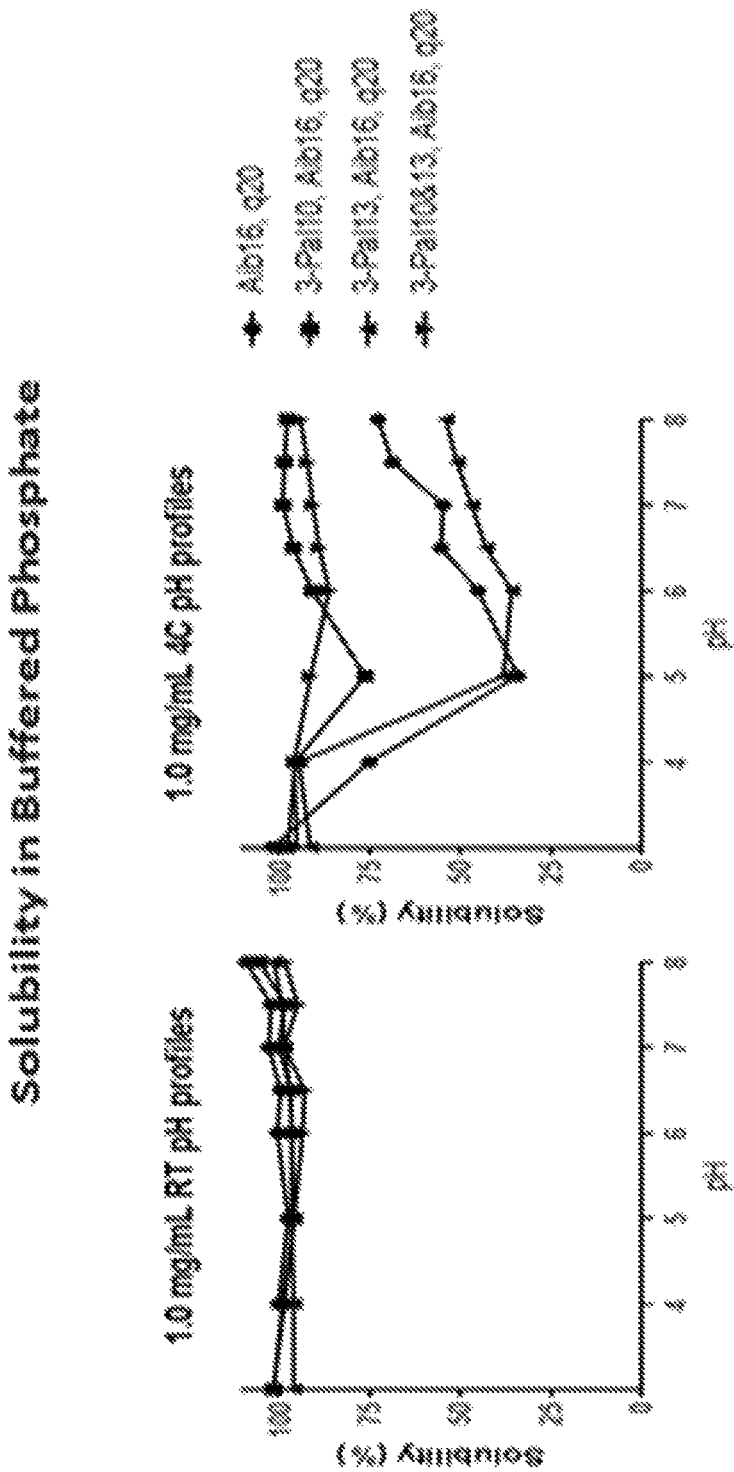
FIGS. 7A & 7B are graphs demonstrating the solubility of glucagon peptides at different pH ranging from pH 4-8 at either room temperature (FIG. 7A) or at 4° C.

FIGS. 7A & 7B are graphs demonstrating the solubility of additional glucagon analogs at different pH, ranging from pH 4-8 at either room temperature (FIG. 7A) or at 4° C. (FIG. 7B). All compounds include a substitution of Aib at position 16 and either a D-amino acid substitution at position 20 and optionally 3-Pal at position 10 and/or 13. Each of these compounds were found to be resistant to fibrillation as measured by the thioflavin-T fluorescence (FIG. 8).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10683334B2). An electronic copy of the "Sequence Listing" will also be available from the USPTO upon request and payment of the fee set forth in 37 CFR 1.19(b)(3).

The invention claimed is:

1. A glucagon peptide having enhanced solubility relative to native glucagon, said glucagon peptide comprising a pyridyl-alanine amino acid substitution at 2 or 3 of positions 6, 10 or 13 relative to the native sequence of glucagon (SEQ ID NO: 1).

2. The glucagon peptide of claim 1 wherein said glucagon peptide comprises a pyridyl-alanine amino acid substitution at positions 10 and 13.

3. The glucagon peptide of claim 1 wherein said glucagon peptide comprises a pyridyl-alanine amino acid substitution at positions 6, 10 and 13.

4. The glucagon peptide of claim 1 wherein each of said pyridyl-alanine amino acids are independently selected from the group consisting of 3-(3-Pyridyl)-L-alanine and 3-(4-Pyridyl)-L-alanine.

5. The glucagon peptide of claim 4 wherein each of the pyridyl-alanine amino acids are 3 (4 Pyridyl)-L-alanine.

6. The glucagon peptide of claim 5 wherein the glucagon peptide comprises Aib at position 16.

7. The glucagon peptide of claim 1 wherein the glucagon peptide comprises the sequence of
a) HSQGTX$_6$TSDX$_{10}$SKX$_{13}$LDX$_{16}$RRAX$_{20}$DFVQWLMX$_{28}$X$_{29}$ (SEQ ID NO: 960) wherein
X$_6$ is a pyridyl-alanine amino acid selected from the group consisting of 3-(3-Pyridyl)-L-alanine and 3-(4-Pyridyl)-L-alanine;
X$_{10}$ is a pyridyl-alanine amino acid selected from the group consisting of 3-(3-Pyridyl)-L-alanine and 3-(4-Pyridyl)-L-alanine;
X$_{13}$ is a pyridyl-alanine amino acid selected from the group consisting of 3-(3-Pyridyl)-L-alanine and 3-(4-Pyridyl)-L-alanine;
X$_{16}$ is Aib;
X$_{20}$ is dGln;
X$_{28}$ is Asn, Asp or Lys; and
X$_{29}$ is Gly, Asp, or Glu; or
b) the sequence of X$_1$X$_2$QGTX$_6$TSDX$_{10}$SKX$_{13}$LX$_{15}$X$_{16}$RRAX$_{20}$DFVX$_{24}$WLMX$_{28}$T (SEQ ID NO: 964)
wherein
X$_1$ is selected from the group consisting of His, D-His, N-methyl-His, alpha-methyl-His, imidazole acetic acid, des-amino-His, hydroxyl-His, acetyl-His, homo-His, and alpha, alpha-dimethyl imidiazole acetic acid (DMIA);
X$_2$ is selected from the group consisting of Ser, D-Ser, Ala, D-Ala, Gly, N-methyl-Ser, Aib, Val, and α-amino-N-butyric acid;
X$_6$ is Phe or pyridyl-alanine;
X$_{10}$ is selected from the group consisting of Tyr, Lys and pyridyl-alanine;
X$_{13}$ is Tyr or pyridyl-alanine;
X$_{15}$ is Asp, Glu, cysteic acid, homoglutamic acid or homocysteic acid;
X$_{16}$ is Glu, Lys, Asp, Ser, glutamine, homoglutamic acid, homocysteic acid, Thr or Aib;
X$_{20}$ is dGln, Gln or Lys;
X$_{24}$ is Gln or Glu;
X$_{28}$ is Asn, Asp or Lys;
with the proviso that for said glucagon peptide at least two of X6, X10 and X13 are pyridyl-alanine.

8. The glucagon peptide of claim 1 wherein the glucagon peptide comprises the sequence HX$_2$QGTX$_6$TSDX$_{10}$SKX$_{13}$LDX$_{16}$RRAQDFVQWLMNT (SEQ ID NO: 965) wherein
X$_2$ is selected from the group consisting of Ser, D-Ser, Ala, D-Ala, Gly, N-methyl-Ser, Aib, Val, and α-amino-N-butyric acid;
X$_6$ is Phe or pyridyl-alanine;
X$_{10}$ is selected from the group consisting of Tyr, Lys and pyridyl-alanine;
X$_{13}$ is Tyr or pyridyl-alanine;
X$_{16}$ is Glu or Aib, with the proviso that at least two of X$_6$, X$_{10}$ and X$_{13}$ are pyridyl-alanine.

9. The glucagon peptide of claim 8 wherein X$_{10}$ is pyridyl-alanine.

10. The glucagon peptide of claim 9 wherein X$_2$ is Aib.

11. The glucagon peptide of claim 1 wherein the glucagon peptide comprises the sequence HSQGTFTSDX$_{10}$SKX$_{13}$LDX$_{16}$RRAX$_{20}$DFVQWLMNT (SEQ ID NO: 969) wherein
X$_{10}$ is 3-(3-Pyridyl)-L-alanine or 3-(4-Pyridyl)-L-alanine;
X$_{13}$ is 3-(3-Pyridyl)-L-alanine or 3-(4-Pyridyl)-L-alanine;
X$_{16}$ is Aib; and
X$_{20}$ is dGln.

12. The glucagon peptide of claim 1 wherein the glucagon peptide comprises a sequence selected from the group consisting of SEQ ID NO: 948, SEQ ID NO: 949, SEQ ID NO: 950 and SEQ ID NO: 951.

13. The glucagon peptide of claim 1 wherein the glucagon peptide comprises the sequence HSQGTX$_6$TSDX$_{10}$SKX$_{13}$LDX$_{16}$RRAQDFVQWLMNT (SEQ ID NO: 950), wherein
X$_6$ is 3-(3-Pyridyl)-L-alanine;
X$_{10}$ is 3-(3-Pyridyl)-L-alanine;
X$_{13}$ is 3-(3-Pyridyl)-L-alanine; and
X$_{16}$ is Aib.

14. The glucagon peptide of claim 1, wherein the glucagon peptide is covalently linked to a non-native acyl or alkyl group.

15. A glucagon peptide having enhanced solubility relative to native glucagon, said glucagon peptide comprising a sequence selected from the group consisting of
X$_1$X$_2$QGTFTSDX$_{10}$SKX$_{13}$LDSRRAQDFVQWLMNT (SEQ ID NO: 962); or
X$_1$X$_2$QGTX$_6$TSDX$_{10}$SKX$_{13}$LDSRRAQDFVQWLMNT (SEQ ID NO: 963);
wherein
X$_1$ is selected from the group consisting of His, D-His, N-methyl-His, alpha-methyl-His, imidazole acetic acid, des-amino-His, hydroxyl-His, acetyl-His, homo-His, and alpha, alpha-dimethyl imidiazole acetic acid (DMIA);
X$_2$ is selected from the group consisting of Ser, D-Ser, Ala, D-Ala, Gly, N-methyl-Ser, Aib, Val, and α-amino-N-butyric acid;
X$_6$ is pyridyl-alanine;
X$_{10}$ is pyridyl-alanine; and
X$_{13}$ is pyridyl-alanine.

16. The glucagon peptide of claim 15 wherein
X$_1$ is His, D-His, or alpha, alpha-dimethyl imidiazole acetic acid (DMIA);
X$_2$ is Ser or Aib; and
said pyridyl-alanine at each of X$_6$, X$_{10}$, and X$_{13}$ is 3-(3-Pyridyl)-L-alanine.

17. A pharmaceutical composition comprising a glucagon peptide of claim 1, and a pharmaceutically acceptable carrier.

18. A method of treating hypoglycemia by increasing blood glucose levels in a patient in need thereof, comprising administering to the patient a pharmaceutical composition of claim 17 in an amount effective to treat hypoglycemia in the patient.

19. The method of claim 18 wherein the glucagon peptide is co-administered with insulin.

\* \* \* \* \*